US010775397B2

(12) United States Patent
Tajima

(10) Patent No.: US 10,775,397 B2
(45) Date of Patent: Sep. 15, 2020

(54) LINEAR MOVEMENT TYPE REACTION TREATMENT APPARATUS AND METHOD THEREOF

(71) Applicant: Universal Bio Research Co., Ltd., Chiba (JP)

(72) Inventor: Hideji Tajima, Matsudo (JP)

(73) Assignee: Universal Bio Research Co., Ltd. (JP)

( * ) Notice: Subject to any disclaimer, the term of this patent is extended or adjusted under 35 U.S.C. 154(b) by 0 days.

(21) Appl. No.: 14/443,256

(22) PCT Filed: Nov. 18, 2013

(86) PCT No.: PCT/JP2013/081082
§ 371 (c)(1),
(2) Date: May 15, 2015

(87) PCT Pub. No.: WO2014/077400
PCT Pub. Date: May 22, 2014

(65) Prior Publication Data
US 2015/0309059 A1    Oct. 29, 2015

(30) Foreign Application Priority Data

Nov. 16, 2012 (JP) ................................ 2012-252731

(51) Int. Cl.
*G01N 35/00* (2006.01)
*G01N 21/64* (2006.01)
*B01L 7/00* (2006.01)
*G01N 35/10* (2006.01)
(Continued)

(52) U.S. Cl.
CPC ............ *G01N 35/0098* (2013.01); *B01L 7/52* (2013.01); *C12N 15/1013* (2013.01);
(Continued)

(58) Field of Classification Search
None
See application file for complete search history.

(56) References Cited

U.S. PATENT DOCUMENTS 4,592,227 A * 6/1986 Poncept ................ G01N 15/05
141/113
5,702,950 A    12/1997 Tajima
(Continued)

FOREIGN PATENT DOCUMENTS

JP        2000-035428       2/2000
WO    WO2012114562 A1 *    8/2011

OTHER PUBLICATIONS

English Translation of International Preliminary Report on Patentability Chapter II dated Jun. 24, 2015 re International Application No. PCT/JP2013/081082.
(Continued)

*Primary Examiner* — Paul S Hyun
(74) *Attorney, Agent, or Firm* — Andrus Intellectual Property Law, LLP

(57) ABSTRACT

An apparatus and related method to reliably prevent cross-contamination and to decrease working time or space involved with reaction treatment. The apparatus includes: a container group having one or more reaction containers and two or more liquid storage portions arranged in a linear shape; a dispensing head to which one or more dispensing tips insertable into the container group are detachably attached, the dispensing head being relatively movable with respect to the container group in a linear direction; a magnetic portion provided in the dispensing head and capable of: applying a magnetic field into each dispensing tip so that the magnetic particles are adsorbed to an inner wall of the dispensing tip, and removing the magnetic field so that the magnetic particles are resuspended in a solution; and an ultrasonic vibration device which applies ultrasonic vibration to a sample storage portion including at least one of the liquid storage portions.

17 Claims, 15 Drawing Sheets

(51) Int. Cl.
*C12N 15/10* (2006.01)
*B01L 3/00* (2006.01)
*G01N 35/04* (2006.01)

(52) U.S. Cl.
CPC ..... *G01N 21/6428* (2013.01); *G01N 21/6452* (2013.01); *G01N 35/00732* (2013.01); *G01N 35/10* (2013.01); *B01L 3/5082* (2013.01); *B01L 2200/0647* (2013.01); *B01L 2300/044* (2013.01); *B01L 2300/0861* (2013.01); *B01L 2300/1822* (2013.01); *B01L 2400/0439* (2013.01); *G01N 35/1002* (2013.01); *G01N 35/1065* (2013.01); *G01N 2021/6439* (2013.01); *G01N 2035/00376* (2013.01); *G01N 2035/0412* (2013.01); *G01N 2035/1053* (2013.01)

(56) References Cited

U.S. PATENT DOCUMENTS

| | | | |
|---|---|---|---|
| 5,779,985 | A | 7/1998 | Sucholeiki |
| 5,895,631 | A | 4/1999 | Tajima |
| 6,455,325 | B1 | 9/2002 | Tajima |
| 8,163,183 | B2 | 4/2012 | Tajima |
| D684,273 | S | 1/2013 | Tajima |
| 9,481,906 | B2 | 11/2016 | Tajima |
| 2001/0012612 | A1* | 8/2001 | Petersen ............ B01L 3/502 435/5 |
| 2003/0066915 | A1 | 4/2003 | Taylor |
| 2006/0281094 | A1 | 12/2006 | Squirrell et al. |
| 2010/0137165 | A1 | 6/2010 | Tajima |
| 2014/0048540 | A1 | 2/2014 | Tajima |

OTHER PUBLICATIONS

Written Opinion of the International Search Authority dated May 16, 2015 re International Application No. PCT/JP2013/081082.
English Translation of International Search Report dated May 22, 2014 re International Application No. PCT/JP2013/081082.
Supplementary European Search Report for EP2921861, EPO, Jun. 27, 2016 (3 pages).
European Search Opinion for EP2921861, EPO, Jul. 6, 2016 (7 pages).

* cited by examiner (a)

(b)

A260 RATIO OF COLLECTION SOLUTION AFTER NUCLEIC ACID PURIFICATION (UNPROCESSED STATE IS SET TO 1)

LINEAR MOVEMENT TYPE REACTION TREATMENT APPARATUS AND METHOD THEREOF

CROSS REFERENCE

This application is a United States national phase application of co-pending international patent application number PCT/JP2013/081082, filed Nov. 18, 2013, which claims priority to Japanese patent application number 2012-252731, filed Nov. 16, 2012, the entire disclosures of which are hereby incorporated herein by reference.

TECHNICAL FIELD

The present invention relates to a linear movement type reaction treatment apparatus and a method thereof.

BACKGROUND ART

Hitherto, in treatment for a biological material such as DNA using magnetic particles, pre-treatment is performed first in a manner such that liquid storage portions are prepared as many as the number of treatment steps and a solution such as a reagent solution necessary for treatment is arranged while being dispensed from a reagent container every treatment. After the arrangement for the solution is completed, a solution stored in each liquid storage portion is suctioned or suctioned after being repeatedly suctioned and ejected using a dispensing device, a magnetic field is applied to magnetic particles so as to separate and adsorb the magnetic particles to an inner wall of a dispensing tip, a remaining solution is ejected to each liquid storage portion, and the dispensing tip is moved to the next liquid storage portion while the magnetic particles are adsorbed to the inner wall. Then, the same process is repeated as many as the number of treatment steps (Patent Literatures 1 and 2).

In this way, in the related art, an empty liquid storage portion needs to be prepared as many as the number of treatment steps other than a reagent container storing a reagent in advance, and a reagent needs to be dispensed and arranged as pre-treatment. For this reason, when the number of steps or reagents used for the treatment is large, the field of the dispensing tip is widened. Accordingly, the movement distance or the working space of the dispensing tip increases or the dispensing tip passes along a complex path. As a result, there is a concern that a movement mechanism or control becomes complex. Further, there is a problem in that the working efficiency in space may be degraded.

Further, in the treatment of the related art, the treatment is started in a manner such that a different dispensing tip is attached to the nozzle of the dispensing device again after pre-treatment of dispensing a reagent necessary for the treatment into each of the liquid storage portions prepared as many as the number of steps. For this reason, it takes treatment time as a whole. As a result, a problem also arises in that the working efficiency in time may be degraded.

Particularly, when a biological tissue such as bacteria, a solid material such as coughed-up sputum, excreta, and food, a high-viscosity material, or a plant is inspected as a sample, it takes a time for pre-treatment to promote a reaction with a reagent caused by the homogenization, the suspension, or the extraction of a target material into a solution, for example, in an inspection or treatment for bacteria having a rigid shell like staphylococcus such as a tubercle bacillus or a pneumococcus. For this reason, the working efficiency in time is degraded or an enough reaction between the target material and the reagent may not be performed. As a result, a problem arises in that the reaction treatment may not be performed with high reliability and efficiency.

Further, in a case where amplification treatment and an optical measurement for the extracted DNA are performed, a reaction container is optically measured by an optical measurement unit when a separated/extracted target material is manually transferred and introduced into the reaction container along with a reaction solution, the reaction container is manually sealed, and a reaction is caused by using a reaction temperature control device in the related art.

In this way, when the steps are manually performed, a user feels a big burden. Further, when the steps are performed in combination of a dispensing device, a centrifugal separation device, a magnetic device, a temperature controller, a reaction container sealing device, and an optical measurement device, the number of the devices in use increases. Thus, there is a concern that the working area may be widened. Particularly, when each nucleic acid extracted from a plurality of samples (specimens) is handled, amplification treatment is needed, and a trouble further increases. Further, there is a concern that the working area may be widened further.

CITATION LIST

Patent Literature

Patent Literature 1: JP 8-62224 A
Patent Literature 2: JP 8-320274 A
Patent Literature 3: WO 96/29602 A1

SUMMARY OF INVENTION

Technical Problem

Therefore, the invention is made to solve the above-described problems, and a first object thereof is to provide a linear movement type reaction treatment apparatus and a method thereof realizing high efficiency in space by decreasing the number of containers or liquid storage portions used for reaction treatment or a working space while reliably preventing cross-contamination.

A second object is to provide a linear movement type reaction treatment apparatus and a method thereof realizing high efficiency in time by decreasing pre-treatment time and improving the reactivity for an inspection target so as to shorten a working time for reaction treatment as a whole.

A third object is to provide a linear movement type reaction treatment apparatus and a method thereof suitable for automation and capable of improving treatment reliability as a whole by realizing automation with high reliability in pre-treatment.

A fourth object is to provide a linear movement type reaction treatment apparatus and a method thereof capable of preventing an increase in apparatus size or a complex apparatus structure and decreasing manufacturing cost by simplifying an optical system structure and measuring a plurality of reaction containers using a small number of measurement units.

A fifth object is to provide a linear movement type reaction treatment apparatus and a method thereof capable of performing highly reliable treatment and reliably preventing the intrusion of external foreign substance into a plurality of reaction containers, the contamination caused by a solution leaked from the plurality of reaction containers, and the mixture of light by automatically and simultaneously performing an optical measurement for the plurality of reaction containers causing a reaction of an amplification of nucleic acid and treatment involved with the optical measurement.

Solution to Problem

In a first invention, a linear movement type reaction treatment apparatus includes: a container group in which one or two or more reaction containers and two or more liquid storage portions are arranged in at least one linear shape; a dispensing head to which one or two or more dispensing tips suctioning and ejecting a liquid through a front end insertable into the reaction containers and the liquid storage portions are detachably attached and which is relatively movable between the dispensing tip and the container group in a linear arrangement direction; a magnetic portion which is provided in the dispensing head and is capable of separating magnetic particles contained in a solution inside each dispensing tip by applying a magnetic field into each dispensing tip so that the magnetic particles are adsorbed to an inner wall of the dispensing tip and of separating the adsorbed magnetic particles by removing the magnetic field therefrom so that the magnetic particles are resuspended in the solution; and an ultrasonic vibration device which applies an ultrasonic vibration to a sample storage portion, as the sample storage portion, at least one of the liquid storage portions are selected.

Here, the "dispensing head" is provided with one or two or more nozzles that suction and eject a gas in the case of a cylinder type, and an attachment opening portion provided at the upper portion of the dispensing tip is fitted to the nozzle. Thus, the dispensing tip is used in an attachable/detachable manner. Since the dispensing head and the container group have a "relative relation", the dispensing head or the container group may move or both the dispensing head and the container group may move. The linear movement type reaction treatment apparatus is provided with a dispensing head movement mechanism or a container group movement mechanism as a "linear movement mechanism" that moves the dispensing head with respect to the container group in at least the linear arrangement direction. However, the movement between the dispensing tip and the container group needs to include the vertical movement in addition to the movement in the linear arrangement direction. The dispensing head movement mechanism or the container group movement mechanism may be used for the movement of the dispensing tip in the linear arrangement direction. However, there is a case where the vertical movement of the dispensing tip is performed by the dispensing head movement mechanism or the container group movement mechanism or a case where the vertical movement of the dispensing tip is performed by the "vertical movement mechanism" for the dispensing tip provided separately from the dispensing head movement mechanism or the container group movement mechanism. In a case where various mechanisms are provided in the dispensing head, the dispensing head or the container group moves only in the linear arrangement direction in the latter case. Accordingly, it is possible to decrease a load applied to the dispensing head, the container group, and the movement mechanism, to extend the apparatus lifetime, and to simplify the apparatus structure.

The "reaction container" is a container that causes a reaction, and the "liquid storage portion" is a container capable of storing a solution. A state where "two or more targets are arranged in a linear shape" indicates a state where the positions (for example, geometric center positions) of the graphic function exhibition points (the points into which the front ends of the dispensing tips are insertable) projected onto a reference plane (normally a horizontal plane in the case of the container) provided with a target is disposed as one line on the plane as the function exhibition portions (for example, the opening portion or the storable space in which the container or the storage portion is involved with the dispensing tip or the nozzle of the dispensing head when the target is the container or the storage portion) of the target disposed on the plane. The linear direction corresponds to the "linear arrangement direction".

The "container group" includes, for example, a micro plate in which a well as various storage portions including the liquid storage portion is disposed in a matrix shape or a column (row) shape or a cartridge-shaped container in which a well as a plurality of storage portions is disposed in a column shape.

The capacity of the "reaction container" is, for example, about 10 μL to 10 mL. Accordingly, the amount of the solution is smaller than the capacity, and becomes about 1 μL to 1000 μL. Thus, the capacity of the dispensing tip needs to be equal to or larger than the capacity of the reaction container. For example, the capacity becomes about 10 μL to 10 mL. The reaction container is formed of, for example, an organic material such as polypropylene, polyester, polyethylene, and acrylic or an inorganic material such as ceramics and metal.

It is desirable to control the temperature inside the reaction container by a temperature controller.

The "temperature controller" includes a temperature source that increases or decreases the temperature inside the reaction container storing a solution as a target for the temperature control based on an external signal or the like. As the temperature source, for example, a peltier device, a heater, a cooler, or the like is provided in a block-shaped member. It is desirable to use, for example, a thermal cycler using a peltier device as the temperature controller when PCR treatment or the like is performed. That is, a temperature control block which increases a temperature by a peltier device is provided in the container group or the stage as the temperature source, and is provided so as to contact or be adjacent to a part (for example, the lower wall portion) or the entirety of the reaction container for the temperature control. Further, isothermal amplification temperature control may be performed according to a LAMP method.

The "temperature control" indicates control of maintaining a solution or a container as a target at one or two or more predetermined temperatures for a predetermined time in accordance with a predetermined procedure a predetermined number of times. The instruction to the temperature controller is performed in a manner such that a corresponding signal is transmitted based on the program.

The "predetermined temperature" indicates a target temperature at which a solution as a target reaches. For example, in a case where nucleic acid of DNA contained in a solution or oligonucleotide as a fragment of nucleic acid is amplified in accordance with a PCR method, a predetermined temperature to be set is, for example, a temperature for a temperature cycle performed by a PCR method, that is, a temperature necessary for each of the elongation, the hybridization, the annealing, and the degeneration of DNA, a temperature of about 94° C., a temperature from 50° C. to 60° C., and a temperature of about 72° C. Meanwhile, a uniform temperature is set to, for example, 55° C. or the like in accordance with a SPIA method (trademark).

Further, in a case where a predetermined high temperature changes to a predetermined low temperature, the predetermined temperature includes, for example, a transition promotion temperature which is lower than these predetermined temperatures and is a cooling target temperature of the temperature controller. Alternatively, in a case where a predetermined low temperature changes to a predetermined high temperature, the predetermined temperature includes a transition promotion temperature which is higher than these predetermined temperatures. In this way, the predetermined temperature includes a transition promotion temperature in which a transition time is shortened so that one cycle time falls within a predetermined cycle time. The "predetermined time" is a time necessary to maintain each temperature, and is dependent on the type of amplification method, the amount of a solution or a reagent used in a PCR method, and the shape, the material, the size, and the thickness of a nozzle. However, the total treatment time in one cycle is, for example, several seconds to several tens of seconds. Further, the total treatment time in the PCR method is, for example, several minutes to several tens of minutes. Furthermore, the transition time is also included in the predetermined time.

The "magnetic particles" indicates a particle having magnetism, and the size thereof is, for example, about 1 nm to several tens of μm. The size, the mass, the material, the structure (a coating of various coating materials on a surface and a single domain), the property (the paramagnetism, the superparamagnetism, the ferromagnetism, ferrimagnetism, and the magnitude of the magnetic force), and the like may be set in accordance with the treatment object. The material is formed of ferrihydrite, hydrate iron oxide, iron oxide, mixed iron oxide, iron, $\gamma\text{-Fe}_2\text{O}_3$, $\text{Fe}_3\text{O}_4$, or the like. The magnetic particles may be obtained by coating the material by a specific coating material. Examples of the coating material include an organic material which causes various functional groups, an ionic material which causes an ion, a surface stabilization material (aliphatic di, polycarboxyl acid, and substitution product and derivative thereof) which prevents aggregation or sedimentation caused by a magnetic field, a specific combination material (ligand or receptor), and a medicinal active material. Alternatively, the magnetic particles may be formed in a manner such that a magnetic body is attached to, incorporated into, or combined with a non-magnetic carrier, for example, an inorganic material such as silica, glass, ceramics, and metal or an organic material such as cellulose, agarose-gel, rubber, and nylon so as to magnetize these materials.

The "ligand" indicates a molecule that is combined by a specific receptor, and includes, for example, a genetic material such as nucleic acid and a biological material such as protein, sugar, sugar chain, and peptide. For example, the ligand indicates agonist and antagonist for a cell membrane receptor, poison (toxin and venom), virus epitope, hormone, hormone receptor, peptide, enzyme, enzyme substrate, lectin, sugar, oligonucleotide, polynucleotide, oligosaccharide, or antibody. The ligand may be a natural material or an artificial material. The "receptor" indicates a material having associativity with respect to the ligand and includes, for example, a genetic material such as nucleic acid and a biological material such as protein, sugar, sugar chain, and peptide. More specific combinations of the receptor and the ligand include, for example, a combination of nucleic acid and complementary nucleic acid, a combination of maltose protein and maltose, a combination of enzyme and substrate, various combinations of antigen and antibody (for example, a combination of biotin and avidin, a combination of biotin and streptavidin), a combination of IgG and protein A, and a combination of ATP protein and ATP.

The "dispensing tip" includes, for example, a wide tube portion, a narrow tube portion, and a connection portion which is used for the connection between the wide tube portion and the narrow tube portion. Here, it is desirable that the wide tube portion be provided with an attachment opening portion into which the lower end of the nozzle is inserted so that the wide tube portion is attached to the nozzle and the narrow tube portion be provided with a front end opening portion through which a solution flows by the suction and the ejection of the gas using the suction/ejection mechanism. The dispensing tip and the nozzle are formed of, for example, an organic material such as resin like polypropylene, polystyrene, polyester, and acrylic and an inorganic material such as glass, metal like ceramics and stainless steel, metal compound, and semiconductor.

In order to apply an "ultrasonic vibration to (the target)", the ultrasonic vibrator of the ultrasonic vibration device may be assembled in the target or directly or indirectly contact the target. As the indirect contact, for example, there is a case where the target contacts the ultrasonic vibrator through the horn contacting the ultrasonic vibrator. Further, it is desirable that the contact position be, for example, the bottom position of the sample storage portion when the target is the "sample storage portion". In addition, for example, there is a case where the contact position may be the side wall or the entire outer surface of the sample storage portion.

The frequency of the "ultrasonic wave" appropriate for the use is set in response to the target, but is, for example, the range of 1 kHz to 1000 kHz and desirably the range of several kHz to several hundreds of KHz. The ultrasonic vibration execution time is set in response to the target, but is several seconds to several hours. Further, the amplitude of the ultrasonic wave is about several μm to several tens of μm.

In order to separate and extract the target material from the sample suspension, at least one liquid storage portion stores the magnetic particle suspension capable of adsorbing the target material. Furthermore, it is desirable that the dispensing tip storage portion, the punching tip storage portion, the scattering prevention lid storage portion, the hermetic lid storage portion, and the measurement end are arranged in the linear arrangement direction in the container group although the arrangement will be described later.

In a second invention, there is provided a linear movement type reaction treatment apparatus including: a container group in which one or two or more reaction containers and two or more liquid storage portions capable of storing a solution are arranged in at least one linear shape; a dispensing head to which one or two or more dispensing tips suctioning and ejecting a liquid through a front end insertable into the reaction containers and the liquid storage portions are detachably attached and which is relatively movable between the dispensing tip and the container group in a linear arrangement direction; and a magnetic portion which is provided in the dispensing head and is capable of separating magnetic particles contained in a solution inside each dispensing tip by applying a magnetic field into each dispensing tip so that the magnetic particles are adsorbed to an inner wall of the dispensing tip and of separating the adsorbed magnetic particles by removing the magnetic field therefrom so that the magnetic particles are resuspended in the solution, wherein the container group includes two or more exclusive regions which correspond to two or more sets of dispensing tips respectively so that one set of dispensing tips enters and the other sets of dispensing tips do not enter, wherein at least one reaction container, one or two or more liquid storage portions storing a magnetic particle suspension and a solution necessary for treatment, and one or two or more tip storage portions storing one or two or more dispensing tips in an attachable manner are arranged in a linear shape in each exclusive region, wherein each set of the dispensing tips is provided so that the dispensing tips move all together in the linear arrangement direction within the exclusive region and the front ends thereof are insertable into any of the reaction container, the liquid storage portion, and the tip storage portion all together in each exclusive region, and wherein the ultrasonic vibration device applies an ultrasonic vibration to a sample storage portion, as the sample storage portion at least one of the liquid storage portions are selected in each exclusive region.

It is desirable that the ultrasonic vibration device apply an ultrasonic vibration to the sample storage portion as at least one sample storage portion in each exclusive region. As the ultrasonic vibration device, there is a case where an ultrasonic vibrator is provided in each exclusive region or a case where one or two or more common ultrasonic vibrators are used to apply an ultrasonic vibration to the sample storage portion in each exclusive region.

It is desirable to dispose exclusive regions so that the linear arrangement directions are parallel and reaction containers, liquid storage portions, and tip storage portions are disposed at the same position coordinate and the same order in the linear arrangement direction, among the exclusive regions. In this case, when a plurality of exclusive dispensing tips corresponding to the exclusive regions are arranged on the dispensing head in the linear arrangement direction of the dispensing head intersecting the linear arrangement direction inside the exclusive regions, the dispensing tips may be provided so as to be insertable into the same kinds of storage portions all together.

When the "exclusive region" is set in control so that one set of dispensing tips enters and the other sets of dispensing tips do not enter and two or more exclusive regions corresponding to the corresponding sets are allocated to the corresponding samples, the cross-contamination between the samples may be reliably prevented. Further, when the exclusive regions are isolated from each other by a partition wall having a predetermined height and higher than the position of the opening portion of each storage portion, the cross-contamination may be further reliably prevented.

In a third invention, there is provided the linear movement type reaction treatment apparatus, wherein the dispensing head is provided with a crossing head which is relatively movable so as to cross the entire exclusive regions and is equipped with one or two or more dispensing tips suctioning and ejecting a liquid through front ends insertable into the reaction container or the liquid storage portion of each exclusive region, and wherein the container group is provided with a common region which is provided outside the exclusive regions and is provided so that the dispensing tips attached to the crossing head are insertable, and includes at least one liquid storage portion into which the front ends are insertable.

A crossing movement unit is provided which is relatively movable between the container group and the main dispensing tip attached so that the crossing head crosses the entire exclusive regions.

Furthermore, since the crossing head is provided in the dispensing head, the crossing head may move in the linear arrangement direction, and the configuration of the movement mechanism may be simplified.

It is desirable that the common region be provided with the tip storage portion which stores one or two or more dispensing tips detachably attached to the crossing head so that the dispensing tip is attachable to the crossing head. Further, it is desirable that a liquid storage portion be provided as one or two or more reagent storage portions which store a result not involved with a sample produced or refined in each exclusive region or a solution such as various reagents not involved with a sample to be supplied to the reaction container or the liquid storage portion of each exclusive region by the crossing head while the dispensing tip is detachably attached to the dispensing head.

Here, a solution such as a reagent to be stored in the reagent storage portion indicates a reagent which is commonly used for the samples, and also indicates a solution that needs to be supplied immediately. For example, in a case where a reagent set to a certain temperature is supplied, a case where a reagent which is formed by a biological material easily changing to be degraded and is not prepacked is supplied, or a case where a product, a produced material, and an extracted material which are produced by treatment are refined, stored, or maintained at a certain temperature, a reagent is stored in a common region different from the exclusive regions and is transferred by using the "crossing head". As the former "reagent or the like", the solution indicates, for example, enzyme of which the temperature needs to be managed, primer or probe which is used for labeling, or water or buffer which is used massively, for example, in the case of the real-time PCR.

In a fourth invention, there is provided the linear movement type reaction treatment apparatus, wherein at least a part of the liquid storage portion is a prepacked storage portion which stores a magnetic particle suspension or a solution necessary for treatment in advance and is sealed by a punchable film, and wherein a punching tip that punches the film is storable in the tip storage portion so as to be attachable to the dispensing head.

A solution which is stored in the prepacked storage portion in the liquid storage portion is different in accordance with the treatment object. For example, in the case where the treatment object is to separate and extract nucleic acid, the solution indicates various separation/extraction solutions, and a dissolving solution which degrades or dissolves protein forming a cellular wall contained in the sample so as to disperse the protein or discharge the fragment thereof to the outside of bacteria or cell, a buffer solution which causes the magnetic particles to easily capture nucleic acid or the fragment thereof, a cleaning solution which removes impurities or residues not captured by the magnetic particles, and a dissociating solution which dissociates nucleic acid captured by the magnetic particles or the fragment of the nucleic acid from the magnetic particles are respectively stored in the prepacked storage portions. Furthermore, it is desirable that each storage portion promote a reaction by repeating the suction/ejection of the mixed solution in which the magnetic particles are suspended.

Further, for example, in a case where the treatment object is to amplify nucleic acid, the solution indicates various amplification solutions. For example, in a case where amplification is performed according to the PCR method, the solution indicates a template DNA solution for an amplification target, a primer solution, a DNA polymerase solution, a nucleotide solution, or a reaction buffer solution. Further, in a case where amplification is performed according to a SPIA method, the solution indicates a DNA/RNA chimera primer solution, a DNA polymerase solution, or a RNaseH solution.

The punching tip is used, for example, while the attachment opening portion provided at the upper portion of the punching tip is attached to the front end of the nozzle used to suction and eject a gas in the dispensing head.

In a fifth invention, there is provided the linear movement type reaction treatment apparatus, wherein the ultrasonic vibration device includes a sample storage portion support base which supports one or two or more sample storage portions in a vibratile manner.

The "sample storage portion support base" contacts the ultrasonic vibrator only through the sample storage portion to be supported, and does not directly or indirectly contact the ultrasonic vibrator without using the sample storage portion. It is desirable to provide the sample storage portion support base so that the sample storage portions are supported at the same position coordinate in the linear arrangement direction in the exclusive regions across the exclusive region when the sample storage portions are individually supported.

In a sixth invention, there is provided the linear movement type reaction treatment apparatus, wherein the sample storage portion includes a scattering prevention lid that closes an opening portion thereof, and the scattering prevention lid is provided with a punchable film.

Here, the punchable film is punched by, for example, the punching tip attached to the dispensing head.

In a seventh invention, there is provided the linear movement type reaction treatment apparatus, wherein at least one scattering prevention lid which is arranged together with the reaction container and the liquid storage portion in a linear shape, and is attached to the opening portion of the sample storage portion by fitting is provided, wherein an upper portion of the scattering prevention lid is formed so as to be attachable to the dispensing head, wherein the scattering prevention lid is attached to the opening portion of the sample storage portion and is detached from the dispensing head so as to be able to close the opening portion.

It is desirable to dispose the scattering prevention lids at the same position coordinate in the linear arrangement direction among the exclusive regions.

It is desirable to provide the scattering prevention lid so that the lower portion thereof is attachable to the opening portion of the sample storage portion by fitting and the upper portion thereof is attachable by fitting to the nozzle which suctions and ejects a gas and is provided in the dispensing head. The scattering prevention lid is detached by using, for example, the detachment mechanism from the dispensing head of the dispensing tip. The detachment mechanism of the dispensing tip is configured as, for example, the vertical movement mechanism of the dispensing tip.

In an eighth invention, there is provided the linear movement type reaction treatment apparatus wherein the dispensing head includes a light guiding trestle that includes two or more link portions which are directly or indirectly linkable to the reaction container and are provided with one or two or more flexible light guiding portions optically connected to the inside of the linked reaction container, a connection end array body that includes an arrangement surface which supports two or more connection ends provided with the rear ends of the light guiding portions having the front ends provided in the link portion along a predetermined path, a measurement unit that is provided so as to be adjacent to or contact the arrangement surface, includes one or two or more measurement ends sequentially and optically connectable to the connection ends along the predetermined path, and is able to receive light based on an optical state inside the reaction container by the optical connection of the connection ends and the measurement ends, and a light guiding-converting mechanism that relatively moves the connection end array body so as to optically connect the connection ends arranged in the connection end array body and the measurement ends.

Here, the "optical state" indicates a light emission state, a coloring state, a discoloring state, or an optical modulation state. The light based on the optical state indicates light which is generated by emitting or discoloring the light, reflected or transmitted light which is generated by the coloring or discoloring, or scattered light. For example, there is an optical state which is generated inside a reaction container while a DNA amplification product is generated when a real-time PCR method or a SPIA (Single Primer Isothermal Amplification) method of amplifying a ratio in nucleic acid amount is used in a test of obtaining qualitative called the analysis of a gene expression amount when a reaction of amplifying nucleic acid (DNA, RNA, or the like) or the fragment (oligonucleotide or nucleotide) thereof is performed.

In the SPIA method, a linear DNA amplification method caused by an isothermal reaction using DNA/RNA chimera primer, DNA polymerase, and RNaseH is used.

Further, in the real-time PCR method, an intercalation method, a hybridization method, and a LUX method are generally known as a method that uses a fluorescence the reagent containing a fluorescent material. The "intercalation method" is a method of measuring a DNA amount by using a characteristic in which a fluorescent material such as SYBR (trademark) GREEN I and ethidium bromide is elongated to enter a double-stranded DNA and emits fluorescence by the irradiation of the excitation light. Accordingly, the amplification solution contains at least a fluorescent material and a quencher for suppressing the emission of fluorescent material. The "hybridization method" is a method of detecting only a target PCR product by using a DNA probe signed by the fluorescent material in addition to the PCR primer. That is, when a DNA probe labeled by fluorescence is hybridized with a target PCR product, the hybridized DNA (amount) is detected. The "LUX method" uses a characteristic in which a fluorescence signal of a fluorescent material labeled by oligonucleic acid is influenced by the shape (the arrangement or single or double chains) of the oligonucleic acid. In the actual real-time PCR, the real-time PCR is performed by using PCR primer (LUX primer) labeled by one kind of fluorescent materials and PCR primer which is not labeled. The LUX primer is designed so that a fluorescent material is labeled in the vicinity of 3'end and a hairpin structure is formed between 3'end and 5'end. When the LUX primer has the hairpin structure, the extinction effect is enhanced, and hence the fluorescence signal increases. When a signal increase amount is measured, the PCR product amount may be measured.

The "link portion" is a member that is directly linked to the reaction container or is indirectly liked thereto through the hermetic lid in a separable manner. The link portion is provided with the front end of the light guiding portion which is optically connected to the inside of the reaction container and is able to guide the light based on the optical state inside the reaction container. Here, the "link to the reaction container" indicates a state where the link portion is connected to the reaction container so as to be adjacent to or is connected to the opening portion, the outer wall, the outer bottom portion, the hermetic lid, or the case of the reaction container. Here, the "adjacent state" indicates a state where the link portion is connected to the light guiding portion so that the optical connection therebetween is possible without any contact therebetween. Further, the "connection state" includes a contact state, a close contact state, an adhesion state, a fitting state, and an attachment state, and indicates a state where the link portion is connected to the light guiding portion in at least the contact state so that the optical connection therebetween is possible. By this linking operation, the light guiding portion provided in the link portion is optically connected to the inside of the reaction container. The link portion indicates, for example, a plate-shaped portion of the light guiding trestle, and the front end of the light guiding portion is a hole punched in the plate-shaped portion, a light transmitting portion such as an optical fiber, or an optical system component such as a lens. Alternatively, the link portion indicates, for example, a cylindrical member that protrudes from the light guiding trestle, and the front end of the light guiding portion is a hollow portion provided in the cylindrical member, a light transmitting portion such as an optical fiber, or an optical system component such as a lens. The flexible light guiding portion indicates, for example, an optical fiber or an optical fiber bundle. In a case where fluorescence is measured, two or more light guiding portions are provided, one of them is used to emit light, and the other of them is used to receive light. Furthermore, in a case where the link portion is directly linked to the opening portion of the reaction container, the inside of the reaction container is sealed by using mineral oil or the like. In this case, it is desirable to form the link portion so that the link portion directly seals the reaction container. Further, in the case of the link to a portion other than the opening portion, the reaction container or the link portion needs to have a light transmitting property.

The "predetermined path" indicates a flat or curved path in which the measurement end and the connection end array body move relatively so that the measurement end may scan all connection ends arranged thereon. Also, a path connecting all connection ends is formed by single or multiple lines (also including a zigzag line and a closed line), a curve (also including a spiral line and a closed curve), or a combination thereof. Desirably, single or multiple paths are lines which are continuous and do not have a cusp or a corner or smooth curves which have a curvature that may be traced by the measurement end.

The link portion and the connection end are provided so as to correspond to each other. For example, there is a case where one link portion corresponds to one connection end, a case where a plurality of link portions corresponds to one connection end, or a case where one link portion corresponds to a plurality of connection ends. In this configuration, the light guiding portion may be branched or merged halfway or a light guiding portion bundle including a plurality of light guiding portions may be branched or merged.

It is desirable to set the predetermined path so that a scanning operation may be smoothly performed based on the number, the shape, the arrangement, and the size of the measurement end of the measurement unit. For example, in the movement of the connection end with respect to the measurement end, a predetermined path is desirable which does not have a sudden change in direction. For example, a linear path is desirable which does not have an obtuse or straight change in direction with respect to the movement direction.

The arrangement pattern of the link portion is, for example, a matrix shape, a columnar shape, or a row shape. Then, the arrangement pattern of the connection end may have a circular shape, a closed curve shape, a columnar shape, or a matrix shape having a small number of columns or rows, for example, in the case of the same arrangement as the above-described arrangement, a similar arrangement only different in size from the above-described arrangement, or a different arrangement pattern. The predetermined path is set so as to pass by all arranged connection ends.

Further, it is desirable that the connection ends be integrally arranged with respect to the arrangement of the link portions. In the case of the "integration", the predetermined path (or the arrangement pattern of the connection end) is formed in an area surrounding the arrangement pattern of the link portions of the light guiding trestle or an area or a gap smaller than the adjacent link portions, and the entire scan distance is desirably formed as short as possible. Accordingly, when the speed is uniform, the treatment may be performed in a short time compared to the case where the measurement end directly scans the link portion.

The integration degree is set, for example, so that the relative movement or scanning operation between the connection end array body and the measurement unit may be used to completely receive the light from the entire reaction containers within the stable light receiving time. Here, the "stable light receiving time" indicates a time in which the optical state inside the reaction container is maintained stably. For example, in the case of a TaqMan probe of a hybridization method, a LUX method, or an intercalation method of the real-time PCR, the stable light receiving time corresponds to the time of the elongation time of each cycle of the PCR. Furthermore, in a case where a FRET probe in a hybridization method is used, the stable light receiving time corresponds to an annealing time.

Accordingly, since the invention may be applied to a light emitting body having a short stable light receiving time, the versatility is high.

When the time taken for one cycle is, for example, several tens of seconds to several minutes, the stable light receiving time becomes, for example, about several seconds to ten seconds. Here, in the early cycle of the PCR reaction, the fluorescence detection amount becomes a detection limit or less. Further, in the late cycle of the PCR reaction, the fluorescence detection amount becomes a plateau state. Thus, in order to ensure the quantitativity in a strict meaning, the fluorescence detection amount becomes within the amplification curve in which an exponential PCR amplification may be observed. In the invention, the stable light receiving time is used for the movement time of the measurement end between the reaction containers. Then, the relative movement necessary for receiving light from each reaction container is performed within the stable light receiving time. Accordingly, it is possible to receive light from the plurality of reaction containers without using a complex optical system component and increasing the size of the apparatus. That is, one measurement unit or measurement units sufficiently smaller than the number of the reaction containers may be used for the treatment.

A "state where the connection ends and the measurement ends are sequentially and optically connected" indicate a state where the connection end and the measurement end are optically connected to each other while facing each other at a close distance. Since the connection moment corresponds to the maximum value of the optical amount that is received by the measurement unit, the measurement control unit specifies a measurement data by calculating a maximum value of the optical amount.

The "measurement unit" is used to measure, for example, fluorescence or chemoluminescence. In the former case, a filter is used to emit one or two or more kinds of excitation light and to receive fluorescence having one or two or more kinds of wavelengths. These kinds of light may be guided by using the optical fiber.

The "measurement end" includes at least a light entrance opening provided in the measurement unit so as to receive light, and includes a light emitting opening for emitting light in the case of the measurement of fluorescence. These openings may be provided in different measurement ends. Further, the light entrance opening or the light emitting opening is optically connected to a light emitting source or a light receiving portion configured as a photoelectric element. At that time, the opening may be connected thereto through a light receiving and guiding portion or a light emitting and guiding portion. Further, it is desirable to provide the connection end array body, the measurement end, and the measurement unit at a position far from the attachment trestle or the reaction container not subjected to the heating control or the temperature control so that a direct contact state or an adjacent state does not occur.

Furthermore, the linear movement type reaction treatment apparatus further includes a "measurement control unit" although not described in the specification. The "measurement control unit" is used to control the measurement unit and the light guiding-converting mechanism and includes a computer (CPU) provided in the linear movement type reaction treatment apparatus and a program driving the computer. For example, a measurement control is performed in a manner such that a signal is transmitted to each of the control units driving the movement mechanisms via a DA converter.

It is desirable that a trestle movement mechanism to be described below use at least a part of the dispensing head movement mechanism. Further, it is desirable that the vertical movement mechanism (for example, the nozzle Z-axis movement mechanism) for the dispensing tip moving the dispensing tip in the Z-axis direction and the trestle movement mechanism (as the vertical movement mechanism of the trestle) be movable independently in the Z-axis direction.

In a ninth invention, there is provided the linear movement type reaction treatment apparatus, wherein the measurement unit is provided so that the inside of the measurement unit excluding the measurement ends is not movable with respect to at least the reaction container and the light guiding trestle including the link portion connected thereto when light is received by the measurement unit.

Accordingly, there is a case where the connection end array body moves with respect to the measurement end or the measurement end moves with respect to the connection end array body. The measurement unit body may be provided so as to be movable with respect to the reaction container or the light guiding trestle until the light guiding trestle is linked to the reaction container. In the former case, for example, the measurement unit body moves along with the light guiding trestle or the movement in a partial direction. Then, in the latter case, the measurement unit body moves along with the reaction container or is fixed to the stage along with the reaction container. Furthermore, the measurement end also includes the light guiding portion which is located outside the measurement unit body and extends to the measurement end.

In a tenth invention, there is provided the linear movement type reaction treatment apparatus including a trestle movement mechanism that moves the light guiding trestle with respect to the container group so that the link portion is directly or indirectly linked to two or more reaction containers all together.

The trestle movement mechanism may press or shake the hermetic lid attached to the opening portion of the reaction container so as to coat the opening portion when the light guiding trestle is movable with respect to the container group in the up and down direction. That is, it is desirable that the measurement control unit be indirectly linked to the link portion through the hermetic lid so as to coat the opening portion of the reaction container and be controlled to press or shake the hermetic lid. Here, the reaction container may be reliably sealed by the pressing operation. Further, the sealing state between the hermetic lid and the opening portion of the reaction container may be promptly and easily released to be opened by the shaking operation. Accordingly, the treatment may be performed with high efficiency and reliability.

Furthermore, in a case where the link portion is linked to the reaction container so as to be adjacent to the reaction container while not being directly or indirectly connected to the opening portion of the reaction container by fitting or the like, it is possible to sequentially and smoothly repeat the linking operation and the separation operation between the link portion and the reaction container by the horizontal movement without the relative movement in the up and down direction.

Further, it is possible to provide the linear movement type reaction treatment apparatus in which two or more link portions provided in the light guiding trestle are arranged in the link portion array body movable in the horizontal direction with respect to the light guiding trestle while being directly or indirectly linkable to two or more reaction containers all together and the link portions are linkable to the reaction containers more than the reaction containers linkable all together by the link portion array body without the movement of the light guiding trestle by the movement of the link portion array body with respect to the light guiding trestle. In this case, it is desirable to perform the linking operation between the link portion and the reaction container within two or more shielding areas isolated by two or more partition walls or two or more grooves provided for the link portion in the light guiding trestle and extending in the horizontal movement direction of the link portion array body so that the link portion is insertable thereinto. Accordingly, it is possible to reliably prevent the mixture of the light from the other reaction container.

In this case, the link portion may be easily and rapidly linked to the reaction container just by the horizontal movement instead of the movement of the light guiding trestle in the up and down direction. Accordingly, when the speed of the link portion array body is set so that the light is received within the stable light receiving time by including the horizontal movement of the link portion array body, it is possible to simultaneously receive and measure the light for a plurality of reaction containers by one set of measurement units.

In an eleventh invention, there is provided the linear movement type reaction treatment apparatus, wherein the measurement unit includes a plurality of kinds of specific wavelength measurement units that includes one or two or more measurement ends optically connectable to the connection ends and is able to receive light of a specific wavelength or a specific wavelength band, and a measurement end array portion that arranges the plurality of measurement ends so that the measurement ends are optically connectable to the connection ends in the predetermined path.

Here, in a case where fluorescence is measured, the measurement unit or each specific wavelength measurement unit is provided with a light receiving portion and a light emitting source that emits corresponding excitation light. The measurement end is provided with a light emitting opening connected to the light emitting source and a light receiving end connected to the light receiving portion. Here, the light emitting opening and the light receiving opening are provided in the same measurement end or separate measurement ends. The measurement end is provided with, for example, a light guiding portion such as a hollow portion, an optical system component like a lens, or an optical fiber.

The "arrangement" is performed in an integral or series manner. The "integral arrangement" indicates a state where the measurement ends are fixed without any freedom of movement. The "series arrangement" indicates a state where the measurement ends are arranged with a certain degree of freedom like a chain. The "arrangement" may be a case where the measurement ends are arranged in a scan direction of a predetermined path or a direction perpendicular to the scan direction. In the latter case, a plurality of paths is arranged in parallel as the predetermined path.

According to the invention, the light emitting materials, the coloring materials, the discoloring materials, or the light changing materials are used. Thus, when amplification treatment is performed on a plurality of kinds of amplification targets at the same condition by one reaction container, it is possible to perform a multiple real-time PCR or a multiple PCR amplification on a plurality of kinds of amplification targets by using the primer labeled by a plurality of kinds of light emitting materials.

Since the "light of the specific wavelength or the specific wavelength band" is used, the range of the wavelength is red, yellow, green, blue, or violet in the case of, for example, visible light.

In a twelfth invention, there is provided the linear movement type reaction treatment apparatus, wherein at least the reaction container and the liquid storage portion are arranged in a linear shape inside each exclusive region, wherein a translucent hermetic lid which is attached to the opening portion of at least one reaction container and seals the reaction container is provided, wherein an upper portion of the hermetic lid is formed so as to be attachable to the dispensing head, and wherein the hermetic lid is attachable to the opening portion of the reaction container by the detachment of the hermetic lid.

Here, the "hermetic lid" includes a flexible film-shaped or membrane-shaped member other than the plate-shaped or block-shaped non-flexible member. The "attachment" includes fitting, threading, friction, sticking, attaching, and adhering. In this case, the detachable attachment state is desirable.

Further, it is desirable to press or shake the link portion or the nozzle with respect to the hermetic lid coating the opening portion of the reaction container when the link portion of the light guiding trestle is linked to the opening portion of the reaction container.

It is desirable that the link portion be provided so as to protrude toward the downside of the light guiding trestle. In this case, it is desirable that the link portion have, for example, a bar shape, a cylindrical shape, or a conical shape and the lower end of the member be contactable with respect to the hermetic lid.

One hermetic lid coats the opening portions of one or two or more reaction containers. The hermetic lid moves while being attached to, for example, the nozzle to be described later, and coats the opening portion of the reaction container by using the tip attachment/detachment mechanism. For that reason, the upper portion of the hermetic lid is provided with one or two or more attachment recesses attachable to one or two or more nozzles. One or two or more link portions may be linked to the reaction container while being inserted into the recess (which is also the link recess) by the movement of the light guiding trestle in the up and down direction.

A dedicated hermetic lid carrying mechanism may be provided without moving the hermetic lid by the nozzle. As the hermetic lid carrying mechanism, the linear movement type reaction treatment apparatus includes, for example, a hermetic lid carrying body that includes one or two or more gripping portions which are arranged in a carrying body in response to the arrangement of the reaction containers and grip the coating plate so that an attachment portion is exposed to the downside while being attachable to the reaction container. Here, the hermetic lid includes a carrying body which is movable with respect to the container group, a coating plate which coats each opening portion of the reaction container, and an attachment portion which protrudes downward from a portion other than the center portion of the coating plate allowing the transmittance of the light and is used to attach the coating plate to the reaction container. Further, when the hermetic lid carrying body is interlocked with the light guiding trestle, the structure of the apparatus may be simplified, and hence an increase in the size of the apparatus may be prevented.

In this case, since there is no need to provide a nozzle attachment recess at the upper portion of the hermetic lid, the link portion may be easily linked only by the horizontal movement between the opening portions of the reaction containers above the hermetic lid without using the movement of the light guiding trestle in the up and down direction. In this case, when the link portion may be moved in the horizontal direction within the stable light receiving time, it is possible to simultaneously receive and measure light from a plurality of reaction containers. Furthermore, it is desirable to provide the hermetic lid at the same coordinate position among the exclusive regions in the linear arrangement direction.

In a thirteenth invention, there is provided the linear movement type reaction treatment apparatus, wherein the light guiding trestle is provided with a heating unit capable of heating the hermetic lid.

For example, the measurement control unit controls the heating unit so that the hermetic lid is heated after the trestle movement mechanism is controlled so that the optical link portion is indirectly linked to two or more reaction containers all together after the hermetic lid is attached to the link portion all together. The "heating unit" has, for example, a heating function of heating a target to a set temperature based on the magnitude of applied current or an on/off control.

Here, the heating of the hermetic lid using the heating unit is performed in order to prevent the condensation during the temperature control of the reaction container sealed by the hermetic lid.

In a fourteenth invention, there is provided the linear movement type reaction treatment apparatus further including: a temperature controller that includes a temperature source provided so as to contact or be adjacent to a lower wall portion of the reaction container; and a heating unit that is provided so as to contact or be adjacent to an upper wall portion of the reaction container located above the lower wall portion of the reaction container and includes a heating source heating the upper wall portion.

Here, the "lower wall portion" indicates a wall portion including a bottom portion and surrounding a portion capable of previously storing a part (for example, 1% to 90%) of the entire capacity of the reaction container or a part of the wall portion. The lower wall portion indicates, for example, a wall portion of a portion capable of storing a predetermined amount of a solution. For example, in the case of the reaction container including a wide opening tube and a narrow opening tube linked to the link portion, the lower wall portion is provided in the narrow opening tube. The "upper wall portion" indicates a container portion surrounding the remaining capacity of the lower container portion storing a predetermined amount of a solution among the total capacity of the reaction container or a part of the container portion. It is desirable that the "upper wall portion" be generally provided at the upper portion of the reaction container with a gap with respect to the lower wall portion. The upper wall portion is close to the opening portion, the hermetic lid, or the link portion in relation to the lower wall portion. For example, in the case of the container including the wide opening tube and the narrow opening tube, the upper wall portion is provided in the wall portion of the wide opening tube when the link portion is linked to the wide opening tube by fitting. The upper wall portion is, for example, a portion corresponding to a stripe shape along the circumference of the container wall.

The measurement control unit controls the heating unit so as to prevent the direct or indirect condensation of the link portion after the trestle movement mechanism is controlled so that the link portion is directly or indirectly linked to the reaction container all together. The "indirect link" indicates a case where the link portion is linked to the reaction container through the hermetic lid or the outer wall of the reaction container. The "control of the heating unit" is performed in response to the "temperature control" in order to prevent the condensation. For example, the heating temperature is controlled at a temperature sufficiently lower than a certain temperature set by the temperature control by a certain temperature degree (a temperature exceeding a dew point of steam necessary for preventing condensation) to several tens of temperature degrees (a temperature sufficiently lower than a melting point of a material of the reaction container). For example, the temperature is controlled so as to be higher than a temperature range from 1° C. to 60° C. and desirably about 5° C. For example, in a case where the amplification is PCR, the target is heated to a temperature higher than 94° C. by several temperature degrees so that the target is heated to, for example, 100° C. Further, in the case of an isothermal temperature, the target is heated to a temperature higher than 55° C. by several temperature degrees so that the target is heated to, for example, a temperature range from about 60° C. to 70° C. when a predetermined temperature is about 55° C.

When the heating unit directly heats the reaction container instead of the link portion or the sealing portion, a thermal influence on the optical system component provided in the link portion or the measurement end near the link portion is suppressed or removed, and degradation in an optical system component such as a prism, an optical fiber, various lenses like an uneven lens, a ball lens, a non-spherical lens, a drum lens, and a refraction index rod lens, a mirror, and a waveguide is prevented, thereby improving the reliability of an image obtained by the optical system component. When various lenses such as a ball lens and a non-spherical lens are used as the optical system component in the link portion, it is possible to reliably collect the light which is generated inside the reaction container and is emitted toward the opening portion and to cause the light to enter a light guiding portion such as an optical fiber so that the light is guided by the light guiding portion.

Here, the reaction container, the temperature controller which includes the temperature source provided so as to contact or be adjacent to the lower wall portion of the reaction container and controls the temperature inside the reaction container, and the heating unit which includes the heating source provided so as to contact or be adjacent to the upper wall portion and heating the upper wall portion constitute the reaction container control system.

In that case, the reaction container includes a wide opening tube and a narrow opening tube which is provided at the lower portion of the wide opening tube so as to communicate with the wide opening tube and is narrower than the wide opening tube. Here, it is desirable that the wide opening tube be fittable to the front end of the link portion, the narrow opening tube store a solution, the lower wall portion be provided in the narrow opening tube, and the upper wall portion be provided in the wide opening tube. Further, it is desirable that the contact surface between the upper wall portion of the reaction container heated by the heating unit or the hermetic lid contacting the upper wall portion and the link portion be set as small as possible. Accordingly, it is possible to reduce or remove an influence of the link portion on the optical system component due to the heating unit.

Furthermore, in the linear movement type reaction treatment apparatus, each link portion is provided with the front end of the light guiding portion bundle including a plurality of light guiding portions, the rear end of the light guiding portion bundle of a part of the light guiding portion bundle is provided in the first connection end of the connection end array body, a part or the entirety of the remaining light guiding portion bundle is provided in the second connection end of the connection end array body, the predetermined path includes the first path and the second path, and in accordance with the movement of the connection end array body, the first measurement end provided in the measurement unit relatively moves along the first path including the first connection end and the second measurement end relatively moves along the second path including the second connection end.

Accordingly, since it is possible to simultaneously emit and receive excitation light for the reaction container or receive a plurality of kinds of wavelength or light of a plurality of wavelength bands by the connection of the plurality of measurement ends of one or a plurality of measurement units, it is possible to treat multiple fluorescence.

Further, in the linear movement type reaction treatment apparatus, the first measurement end is optically connected to the light receiving portion of the measurement unit, the second measurement end is connected to the light emitting source of the measurement unit, the front end corresponding to the first connection end and the front end corresponding to the second connection end are arranged in a mixed state, the first measurement end is connectable to the first connection end, and the second measurement end is connectable to the second connection end.

Here, as the "mixture of the front ends", it is desirable that two kinds or more of light guiding portions be disposed in a mixed state so that the front ends thereof are homogenized.

Accordingly, it is possible to reliably measure the intensity in response to the fluorescence amount by emitting the excitation light into the reaction container without any unevenness during the measurement of fluorescence.

In a fifteenth invention, there is provided the linear movement type reaction treatment apparatus, wherein a sample information item used to identify or manage a sample and an inspection information item used to represent an inspection content are visually displayed in each exclusive region, and wherein the crossing head is provided with a digital camera which obtains an image data by capturing a content displayed in each exclusive region including the sample information item and the inspection information item.

Here, the "sample information item" indicates an information item which is necessary to identify or manage the sample. As the information item for identifying the sample, for example, a sample attribute of a patient, an animal, a food material, soil, and sewage as a sample target may be exemplified. For example, the sample attribute indicates a name, an age, a sex, and an ID number of a patient. Further, the information item for identifying the sample is a food material sale place, a soil sampling place, a sampling time, or the like. Alternatively, the information item for identifying the sample is the attribute of an extracted sample. For example, the attribute of the extracted sample indicates a blood, urine, excrement, and a body liquid of a patient, a type of a cell, a type of a food material, a type of soil, or a type of sewage. Alternatively, the information item for managing the sample is, for example, a sample collector, a sample collection date, a person who is in charge of the test of the sample, or a sample test date.

The "inspection information item" indicates an information item representing the content of the inspection for the sample. For example, an inspection item may be exemplified. The inspection item indicates, for example, various genetic information items (for example, SNPs, base arrangement determination), a genetic diagnosis, the other protein information item, a type of a reagent used for the inspection, a reagent manufacturing lot number, a reagent detection amount curve, a type or a structure of an inspection tool, or a type of a biological material fixed to a carrier. These information items are marked as handwriting, printing, a barcode, or a QR (trademark) code (matrix 2D code). The image data is analyzed, and is output while being converted into the analysis data corresponding to the code data.

In a sixteenth invention, there is provided the linear movement type reaction treatment apparatus, wherein the ultrasonic vibration device includes an ultrasonic vibration unit that includes an ultrasonic vibrator and a horn resonated by the vibration and a vibration unit movement mechanism that is relatively movable between the ultrasonic vibration unit and the sample storage portion, and wherein the ultrasonic vibration device applies the ultrasonic vibration by pressing the sample storage portion using the horn.

The plurality of sample storage portions may be provided inside the container group arranged as one linear column or may be provided in the container group disposed in each exclusive region. It is desirable to include the forward/backward movement mechanism that moves the horn toward the outside of the ultrasonic vibration unit in a forward/backward movement manner in addition to the vibration unit movement mechanism. Furthermore, it is desirable that the horn or the sample storage portion is elastically biased in the outward direction. In a case where the plurality of sample storage portions is disposed at the same position coordinate in the linear arrangement direction among the exclusive regions, the movement direction of the ultrasonic vibration unit is set so that the ultrasonic vibration unit is movable in a direction perpendicular to the linear arrangement direction so as to cross the entire exclusive regions.

In a seventeenth invention, there is provided a linear movement type reaction treatment method including: arranging at least one reaction container and two or more liquid storage portions as a container group in at least one linear shape; detachably attaching one or two or more dispensing tips to a dispensing head; moving the dispensing head in the linear arrangement direction with respect to the container group; storing a sample suspension in a sample storage portion as at least one sample storage portion of the liquid storage portion by using the dispensing tip; applying an ultrasonic vibration to the sample storage portion; and transferring each sample suspension in the linear arrangement direction to the next liquid storage portion disposed in a linear shape or the reaction container by using the dispensing tip.

When the sample suspension needs to be stored in the sample storage portion, for example, the sample suspension is suctioned from a separate container storing a parent specimen by the dispensing head, is transferred, and is ejected into the sample storage portion while the front end thereof is inserted into the sample storage portion. Furthermore, it is desirable that the dispensing head be provided with the magnetic portion and a part of the liquid storage portion store the magnetic particle suspension when the target material is separated and extracted. Further, it is desirable that the container group be provided with the common region and the crossing head enter the common region so that the front end of the dispensing tip is inserted into at least one liquid storage portion provided in the common region.

In an eighteenth invention, there is provided a linear movement type reaction treatment method including: providing two or more exclusive regions corresponding to two or more sets of dispensing tips respectively so that one set of dispensing tips enter and the other sets of dispensing tips do not enter in a container group; arranging at least one reaction container, two or more liquid storage portions storing a magnetic particle suspension and a solution necessary for treatment, and one or two or more tip storage portions storing one or two or more dispensing tips in an attachable manner in a linear shape in each exclusive region; detachably attaching each set of dispensing tips to the dispensing head; relatively moving the dispensing head in the linear arrangement direction inside each exclusive region all together and inserting the front end of the dispensing tip into any of the reaction container, the liquid storage portion, and the tip storage portion of each exclusive region all together so as to suction or eject a solution through the front end thereof; and applying an ultrasonic vibration to a sample storage portion, as the sample storage portion at least one of the liquid storage portions are selected in each exclusive region. Accordingly, a sample suspension is ejected from the front end of the dispensing tip into the sample storage portion so as to be stored therein before an ultrasonic vibration is applied to the sample storage portion.

In a nineteenth invention, there is provided the linear movement type reaction treatment method further including: providing a common region including at least one liquid storage portion and one or two or more tip storage portions storing one or two or more dispensing tips in an attachable manner in the container group outside the exclusive region; detachably attaching one or two or more dispensing tips provided in the common region to a crossing head provided in the dispensing head and movable with respect to the liquid storage portion of the common region and the reaction container or the liquid storage portion of each exclusive region; causing the crossing head to enter the entire exclusive regions and the common region; and inserting the front end into the reaction container or the liquid storage portion of the exclusive region or the liquid storage portion of the common region so as to suction or eject a solution through the front end.

In a twentieth invention, there is provided the linear movement type reaction treatment method including: transferring each scattering prevention lid stored in a position in the linear arrangement direction while each scattering prevention lid is attached to the dispensing head, after storing each sample suspension in each sample storage portion; attaching the scattering prevention lid to the opening portion of the sample storage portion so as to close the opening portion; and applying an ultrasonic vibration to each sample storage portion, after detaching the scattering prevention lid from the dispensing head.

Accordingly, the scattering prevention lid is disposed in the linear arrangement direction along with the sample storage portion, the reaction container, and the liquid storage portion.

Furthermore, the punching tip which is stored at a position in the linear arrangement direction is attached to the dispensing head after an ultrasonic vibration is applied to the sample storage portion. Then, the scattering prevention lid is punched, the punching tip is detached, and the dispensing tip is attached to the dispensing head so as to suction the crushed sample and eject the sample to the liquid storage portion. Accordingly, for example, the target material is captured by the magnetic particles, the magnetic particle suspension is suctioned by the dispensing tip, and then the magnetic particle suspension is ejected to the next liquid storage portion in the linear arrangement direction while the dispensing tip moves to the next liquid storage portion.

In a twenty-first invention, there is provided the linear movement type reaction treatment method including: extracting a target material from the sample suspension stored in each sample storage portion to which the ultrasonic vibration is applied; moving the target material in the linear arrangement direction and storing the target material in two or more reaction containers provided in the container group; moving a light guiding trestle including two or more link portions provided with front ends of one or two or more flexible light guiding portions with respect to each reaction container; directly or indirectly linking the reaction containers to the link portion all together so as to optically connect the inside of the linked reaction container to the light guiding portion; performing temperature control inside the reaction container; guiding light from the reaction container to a connection end array body including an arrangement surface supporting two or more connection ends provided with the rear ends of the light guiding portions having the front ends provided in the link portion in a predetermined path, and sequentially and optically connecting the connection ends to one or two or more measurement ends provided in a measurement unit provided so as to be adjacent to or contact the arrangement surface in the predetermined path by the relative movement thereof, so that light based on an optical state inside the reaction container is received by the measurement unit.

In a twenty-second invention, there is provided the linear movement type reaction treatment method, wherein the measurement unit includes a plurality of kinds of specific wavelength measurement units capable of receiving light of a specific wavelength or a specific wavelength band, wherein each specific wavelength measurement unit includes at least one measurement end sequentially and optically connectable to each connection end in the predetermined path, wherein the plurality of measurement ends is arranged by a measurement end array portion, and the measurement ends are sequentially and optically connected to the connection ends in the path, and wherein each specific wavelength measurement unit receives light of a specific wavelength or a specific wavelength band based on the optical state inside the reaction container.

Furthermore, in the linear movement type reaction treatment method, it is desirable that two or more translucent hermetic lids which are arranged in the container group and are fittable to the opening portions of the reaction containers be attached to the reaction containers all together and the light guiding trestle be moved with respect to the hermetic lid of the reaction container.

Further, in the linear movement type reaction treatment method, it is desirable to press or shake the hermetic lid coating the opening portion of the reaction container.

Accordingly, it is possible to reliably seal the reaction container by performing control of pressing the hermetic lid coating the opening portion of the reaction container. Further, it is possible to immediately and easily release the sealing state between the opening portion of the reaction container and the hermetic lid so as to be opened by shaking the hermetic lid. Accordingly, it is possible to obtain high treatment efficiency and reliability.

Further, when the opening portion of the reaction container is directly or indirectly linked to the link portion so as to control the temperature inside the reaction container, the direct or indirect condensation of the link portion may be prevented by heating the upper wall portion of the reaction container located at the upper portion in relation to the lower wall portion in response to the temperature control of the temperature controller including the temperature source provided so as to contact or be adjacent to the lower wall portion of the reaction container by the use of the heating source of the heating unit provided so as to contact or be adjacent to the upper wall portion.

In a twenty-third invention, there is provided a linear movement type reaction treatment method including: detachably attaching a dispensing tip to a dispensing head; relatively moving the dispensing head and a container group in a linear arrangement direction so as to separate a target material using a magnetic particle suspension having magnetic particles suspended to capture at least a target material, a sample suspension stored in a sample storage portion to which an ultrasonic vibration is applied, and a separation/extraction solution of a target material arranged in a linear shape in the container group; introducing the separated target material and a reaction solution used for a reaction into a plurality of reaction contains located in the linear arrangement direction of the container group; moving a light guiding trestle provided in the dispensing head and including two or more link portions provided with front ends of one or two or more light guiding portions with respect to a reaction container along with the dispensing head; directly or indirectly linking the reaction containers to the link portion all together so as to optically connect the inside of the linked reaction container to the light guiding portion; performing temperature control inside the reaction container; and guiding light from the reaction container to a connection end array body supporting two or more connection ends provided with the rear ends of the light guiding portions having the front ends provided in the link portion and provided so as to correspond to each link portion in a predetermined path, and sequentially and optically connecting the connection ends to one or two or more measurement ends provided in a measurement unit provided so as to be adjacent to or contact the arrangement surface by the relative movement thereof, so that light based on an optical state inside the reaction container in accordance with the sequential optical connection in the predetermined path is received by the measurement unit.

In a twenty-fourth invention, there is provided the linear movement type reaction treatment method, wherein in the applying of the ultrasonic vibration to the sample storage portion, the ultrasonic vibration unit including the ultrasonic vibrator and the horn resonated by the vibration is moved with respect to the sample storage portion so as to apply the ultrasonic vibration to the sample storage portion by pressing the sample storage portion using the horn. It is desirable that the horn move forward in the outward direction from the ultrasonic vibration unit approaching the sample storage portion and press the sample storage portion. The "approach" indicates, for example, a state where the front end of the horn approaches the bottom portion or the side surface of the sample storage portion within the horn arrival distance. Furthermore, it is desirable that the horn or the sample storage portion be supported so as to be elastically biased in the outward direction. When the horn is elastically biased in the outward direction, it is desirable that the sample storage portion be supported so as not to be movable in the outward direction (the same applies to the sixteenth invention).

Advantageous Effects of Invention

According to the first, seventeenth, eighteenth, or twenty-third invention, the reaction container, the liquid storage portion, and the sample storage portion used for the treatment are arranged in a linear shape. Accordingly, since the treatment including the pre-treatment may be performed consistently just by the movement of the dispensing head in the linear arrangement direction, the movement path of the dispensing tip is simplified, and the control is easy. Further, since the movement distance is the shortest, the treatment including the pre-treatment may be immediately and efficiently performed. Further, the burden of the user may be reduced. In addition, since the movement path is simplified, the cross-contamination may be reliably prevented by separating the movement paths of the corresponding samples. Since an ultrasonic vibration is applied to the sample, the extraction of the target material obtained from the sample and the homogenization and the suspension of the sample may be promoted. Then, since the reaction is promoted, the treatment may be immediately and efficiently performed. Further, the reliability of the treatment may be improved.

According to the second or eighteenth invention, the exclusive region is set as two or more exclusive regions so that one set of dispensing tip enters and the other sets of dispensing tips do not enter. Further, the reaction container and the like are arranged in a linear shape, and the movement of each set of the dispensing tips is limited as the movement in the linear arrangement direction by control. Accordingly, it is possible to reliably prevent the cross-contamination among the exclusive region. Further, since a separation unit including a unit necessary for the pre-treatment is provided in each exclusive region, the treatment may be consistently performed within each exclusive region, and hence the cross-contamination may be further reliably prevented.

According to the third or nineteenth invention, since the crossing head is provided so as to cross the entire exclusive regions in a relatively movable manner, this configuration is suitable for a case where a common reagent which is not suitably prepacked in the liquid storage portion of the plurality of exclusive regions and corresponds to, for example, a reagent to be heated or cooled necessarily or a reagent to be degraded in time easily is stored and supplied to the liquid storage portion or a case where a product, a produced material, or a result obtained in each exclusive region is stored and kept in a region separated from the exclusive region.

According to the fourth invention, since at least a part of the liquid storage portions is used as the prepacked storage portion sealed by the punchable film and storing a magnetic particle suspension or a solution necessary for the treatment in advance, there is no need to dispense the solution or the magnetic particle suspension to an empty liquid storage portion during treatment. Furthermore, since the punching tip located at a position in the linear arrangement direction is attached to the dispensing head for the punching operation and the dispensing tip is attached to the dispensing head after the detachment of the punching tip, it is possible to immediately perform treatment with high precision.

According to the fifth invention, since the sample storage portion support base is provided so as to support the sample storage portion in a vibratile manner, it is possible to prevent the propagation of the ultrasonic vibration to a portion other than the sample storage portion to be subjected to the ultrasonic vibration, and hence to efficiently apply the ultrasonic vibration to the sample storage portion.

According to the sixth or twentieth invention, since the sample is stored in the sample storage portion and the opening portion thereof is closed by the scattering prevention lid, it is possible to prevent the sample from being scattered in a vibration state, and hence to prevent the contamination of the sample in a portion other than the sample storage portion. Since the lid is punched and the sample therein is taken out by being suctioned with the dispensing tip after the vibration is applied to the sample, there is no need to open the lid by the user. Thus, it is possible to reduce a burden of the user and to prevent the contamination to the user. Further, since there is no need to attach the lid in a detachable state, the lid may be stably and safely attached so that the lid is not separated due to the vibration or the like.

According to the seventh invention, the scattering prevention lid for sealing the sample storage portion is attached to the sample storage portion by fitting, and the upper portion of the scattering prevention lid is attachable to the dispensing head. Further, the scattering prevention lid is disposed in the linear arrangement direction along with the reaction container or the liquid storage portion. Accordingly, since the dispensing head moves in combination with the movement in the linear arrangement direction, the sample storage portion may be easily sealed by the scattering prevention lid.

According to eighth or twenty-first invention, since the link portion is optically connected to the inside of the reaction container by the linking operation of the link portion provided in the light guiding trestle with respect to the plurality of reaction containers, a signal based on the optical state inside the reaction container is transmitted to the connection end of the arrangement surface of the connection end array body through the plurality of reaction containers, the light guiding trestle, and the light guiding portion, and the connection ends arranged along the predetermined path on the arrangement surface of the connection end array body are sequentially and optically connected to the measurement ends of the measurement units. Accordingly, since it is possible to prevent the leakage of light or the attenuation of light caused by the scattering of the light between the measurement end and the liquid surface and to arrange the connection ends again so that the connection with respect to the measurement end is reliably, immediately, and smoothly performed compared to the case where the measurement end is directly scanned with respect to the opening portion of the reaction container, it is possible to realize the highly reliable measurement and the measurement for the optical state inside the reaction container in a more efficient and immediate manner.

That configuration may be realized by the integration in which the entire connection end arrangement area or the distance between the adjacent connection ends is set to be smaller than the like portion arrangement area or the adjacent distance thereof, the linearization of the predetermined path compared to the arrangement of the link portion, or the smooth movement of the measurement end in accordance with an increase in curvature radius while the stable light receiving time and the measurement end structure are taken into consideration.

Since the optical system is switched by the movement along the predetermined path on the arrangement surface between the measurement end and the connection end, the structure of the optical system may be simplified. Further, since the connection end, the measurement end, and the measurement unit are separated from the light guiding trestle or the reaction container subjected to the temperature control or the heating control, it is possible to perform highly reliable treatment by excluding a thermal influence on the optical component.

The movement of the connection end with respect to the measurement end includes a continuous or intermittent movement. As a result of the measurement using the real-time PCR, an amplification curve is created, and may be used for various kinds of analysis such as a determination of the initial concentration of DNA.

Further, since the plurality of reaction containers may be measured by one measurement unit by using the stable light receiving time, the number of the measurement units may be decreased. Thus, an increase in the size of the apparatus may be suppressed and the manufacturing cost may be reduced. Further, since the measurement may be performed by the movement between the measurement end and the connection end as the shortest distance along the predetermined path, the measurement may be performed in parallel by a simple mechanism as only the movement mechanism.

Since the opening portion of the reaction container is directly or indirectly linked by the link portion, it is possible to perform a high reliably automatic measurement capable of reliably preventing the cross-contamination and the mixture of light when a reaction and a measurement are performed while the reaction container is closed.

According to the ninth invention, since the measurement unit is not movable with respect to the reaction container and the light guiding trestle linked thereto during the movement with respect to the measurement ends and the connection ends arranged on the connection end array body, it is possible to perform a highly reliable and precise measurement by preventing the deviation of the optical system component or the breakage of the electronic system component without applying a load caused by the inertia due to the acceleration in accordance with the movement to the electronic system component or the optical system component incorporated into the measurement unit body during the measurement. Furthermore, since the measurement unit body is movable with respect to the reaction container in a case other than the measurement, the measurement may be performed while the measurement unit is carried to the vicinity of the reaction container.

According to the tenth invention, since the trestle movement mechanism is provided which moves the light guiding trestle, the link portion may be directly or indirectly linked to the reaction container without a manual operation, and hence the cross-contamination may be prevented. Accordingly, the treatment may be performed with high efficiency.

According to the eleventh or twenty-second invention, since the light emitting materials, the coloring materials, the discoloring materials, or the light changing materials are used in one reaction container, it is possible to perform a multiple real-time PCR or a multiple PCR amplification by using primer labeled by a plurality of light emitting materials for a plurality of kinds of amplification targets, for example, in a case where a plurality of kinds of amplification targets is amplified at the same condition by one reaction container. At that time, since the light of a plurality of kinds of specific wavelengths or specific wavelength bands is selectively received within the stable light receiving time by using a mechanism used for the movement between the plurality of reaction containers, there is no need to separately provide a particular photoelectric conversion mechanism. Thus, the structure of the apparatus is simplified, and hence the manufacturing cost may be simplified. Further, since each specific wavelength measurement unit is configured to receive light of a single specific wavelength or a specific wavelength band, it is possible to perform a highly precise measurement without the influence from the other specific wavelengths or specific wavelength bands. Further, since each specific wavelength measurement unit may be provided as a module so that the module is added or removed, it is possible to perform a most versatile treatment in accordance with the treatment object.

According to twelfth or twenty-third invention, since the hermetic lids arranged in the container group are attached to the link portion or the nozzle, the hermetic lid may be attached to the opening portion of the reaction container by the movement of the dispensing head. Further, since the material stored in the reaction container does not directly contact the link portion of the trestle, the cross-contamination may be effectively prevented. Further, since there is no need to provide a dedicated mechanism for attaching the hermetic lid to the reaction container, the manufacturing cost is reduced without increasing the size of the apparatus.

According to thirteenth invention, since control is performed so that the hermetic lid is heated, it is possible to prevent the condensation during the temperature control of the reaction container sealed by the hermetic lid, and to reliably perform a measurement through the translucent hermetic lid with high precision.

According to fourteenth invention, since the upper wall portion of the reaction container is heated in response to the temperature control of the lower wall portion of the reaction container, the directly or indirect condensation of the link portion may be prevented. In this case, since the upper wall portion of the reaction container is heated instead of directly heating the link portion or the hermetic lid, it is possible to reduce or remove a direct heating influence on the optical system component provided in the link portion. Accordingly, since it is possible to reduce or remove an image distortion caused by degradation or deterioration of the optical system component and to provide various optical system components in the link portion, it is possible to precisely perform the most versatile treatment. Further, since there is no need to provide the heating unit direct above the container, the structure of the apparatus is simplified in accordance with the structure direct above the container. Furthermore, it is possible to reliably perform an optical treatment by further moving the link portion including the optical system component to the container. Furthermore, it is possible to perform a highly reliable measurement by performing temperature control on the lower wall portion in response to the heating of the upper wall portion so that the temperature becomes a uniform temperature using a peltier device capable of performing a cooling operation.

According to the fifteenth invention, since an information item is displayed on the exclusive region and the information item displayed on each exclusive region is read by a camera in accordance with the movement of the crossing nozzle, it is possible to perform a reaction and a measurement with high reliability without increasing the size of the apparatus.

According to the sixteenth or twenty-fourth invention, since the plurality of sample storage portions and at least one ultrasonic vibration unit are moved relatively, it is possible to simplify the structure of the apparatus by decreasing the number of the components of the ultrasonic vibrator and the horn and to reduce the manufacturing cost of the apparatus. Further, since the ultrasonic vibration device applies a vibration to the target through the sample storage portion, there is a low concern for the cross-contamination without any direct contact of the target. Further, when the forward/backward movement mechanism is provided, it is possible to reliably apply an ultrasonic vibration to the sample storage portion by sequentially pressing the sample storage portion using the horn of the ultrasonic vibration unit.

DESCRIPTION OF EMBODIMENTS

Next, embodiments of the invention will be described with reference to the drawings. Furthermore, it should not be understood that the embodiments limit the invention unless otherwise stated. Further, the same reference signs will be given to the same components of the embodiments, and the description thereof will not be repeated.

Figure 1:
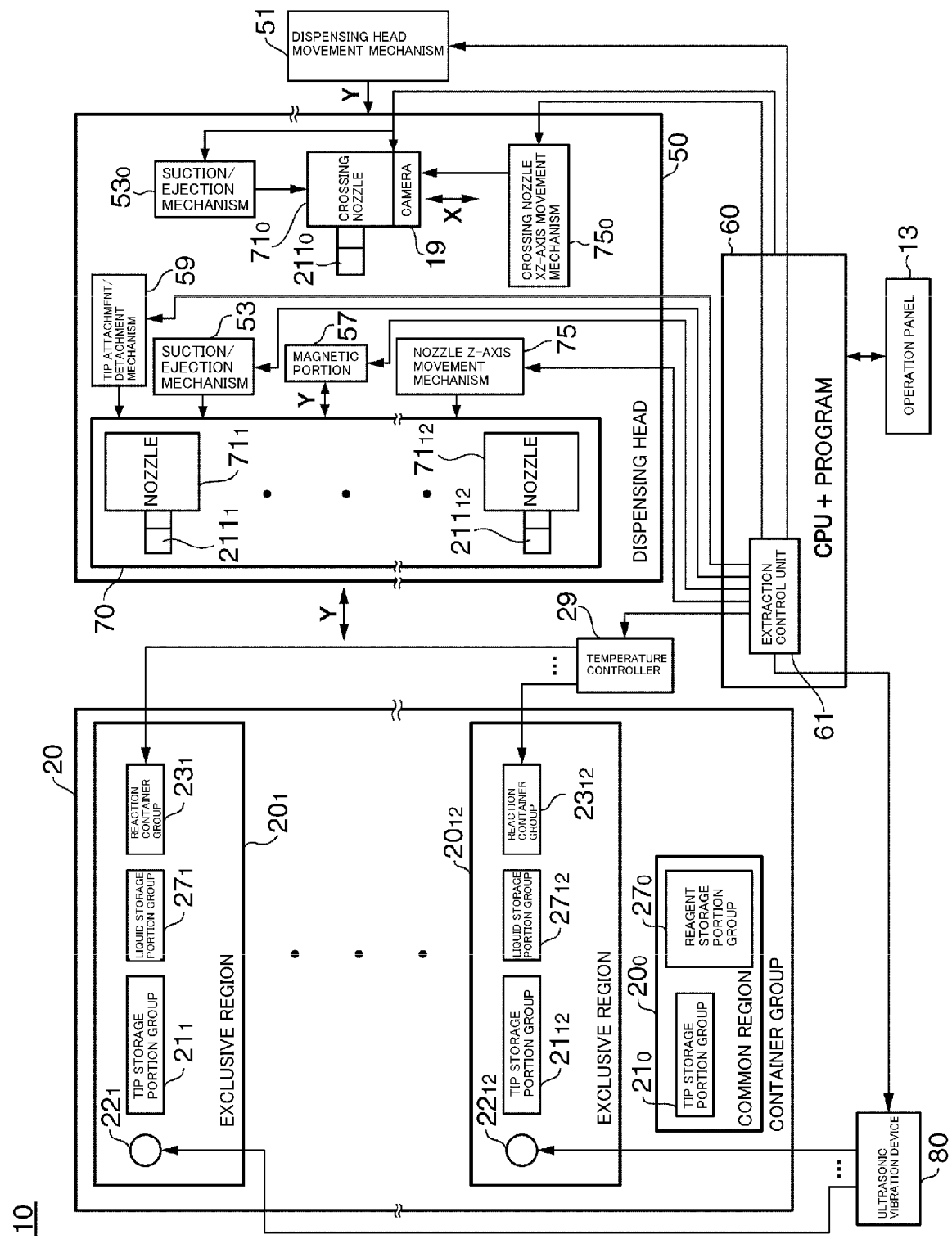
FIG. 1 is an entire block diagram illustrating a linear movement type reaction treatment apparatus according to a first embodiment of the invention.

FIG. 1 is a block diagram illustrating a linear movement type reaction treatment apparatus 10 according to a first embodiment of the invention.

The linear movement type reaction treatment apparatus 10 includes a container group 20 that includes a plurality of (in this example, twelve) exclusive regions $20_i$ (i=1, ..., 12, omitted below) and a common region $20_0$, a dispensing head 50 that includes a nozzle arrangement portion 70 in which a plurality of (in this example, twelve) nozzles $71_i$ respectively and detachably equipped with dispensing tips $211_i$ provided so that the front ends thereof are insertable into reaction containers respectively provided in the exclusive regions $20_i$ and the liquid storage portions thereof and a crossing nozzle $71_0$ which is movable so as to cross the entire exclusive region $20_i$ and is detachably equipped with a dispensing tip $211_0$ provided so that the front end thereof is insertable into the liquid storage portions provided in the exclusive regions $20_i$ and the common region $20_0$, and a magnetic portion 57 that is provided in the dispensing head 50 and gives an influence of a magnetic field to the dispensing tip $211_i$ attached to the nozzle arrangement portion 70. Here, the crossing nozzle $71_0$ corresponds to one example of the "crossing head".

The linear movement type reaction treatment apparatus 10 further includes a dispensing head movement mechanism 51 that serves as a "linear movement mechanism" which moves the dispensing head 50 in the Y-axis direction as a linear arrangement direction, a temperature controller 29 that controls the temperature of the reaction container group $23_i$ in each exclusive region $20_i$, an ultrasonic vibration device 80 that controls an ultrasonic vibrator for applying an ultrasonic vibration to the sample storage portion $22_i$ in each exclusive region $20_i$, a CPU+program 60 that is configured as a CPU, ROM, RAM, and various memories and realizing a communication function via a LAN or the like, and a program stored in the ROM and the like, and an operation panel 13 that is a liquid crystal display including a display unit or an operation unit such as an operation key or a touch key.

The dispensing head 50 further includes a nozzle Z-axis movement mechanism 75 that serves a "vertical movement mechanism" which moves the nozzle arrangement portion 70 in the Z axis with respect to the container group 20, a suction/ejection mechanism 53 that suctions and ejects a solution from and to a main dispensing tip $211_i$ attached to the nozzle $71_i$ by suctioning and ejecting a gas from and to the nozzle $71_i$, a tip attachment/detachment mechanism 59 that is separably equipped with the main dispensing tip $211_i$ detachably attached to the nozzle $71_i$, a suction/ejection mechanism $53_0$ that suctions and ejects a solution from and to the main dispensing tip $211_0$ attached to the nozzle $71_0$ by suctioning and ejecting a gas from and to the crossing nozzle $71_0$, a crossing nozzle XZ-axis movement mechanism 75 that moves the crossing nozzle $71_0$ in the X-axis direction and the Z-axis direction perpendicular to the linear arrangement direction (the Y-axis direction), and a digital camera 19 that is provided in the crossing nozzle $71_0$.

The CPU+program 60 generates an instruction of a series of treatment for an extraction (including ultrasonic fragmentation), an amplification, and a sealing of an amplification solution for nucleic acid or a fragment thereof with respect to the temperature controller 29, the dispensing head movement mechanism 51, the tip attachment/detachment mechanism 59, the suction/ejection mechanism 53, the magnetic portion 57, the nozzle Z-axis movement mechanism 75, the ultrasonic vibration device 80, the crossing nozzle $71_0$, the camera 19, the crossing nozzle XZ-axis movement mechanism $75_0$, and the suction/ejection mechanism $53_0$.

The container group 20 includes the common region $20_0$ and the plurality of (in this example, twelve) exclusive regions $20_i$ that respectively corresponds to the nozzles $70_i$ so that one (in this example, one set corresponds to one) nozzle $70_i$ enters and the other nozzles $70_K$ (k≠i) do not enter. Each exclusive region $20_i$ includes a liquid storage portion group $27_i$ that includes a plurality of storage portions storing or capable of storing a reagent and a tip storage portion group $21_i$ storing a plurality of dispensing tips $211_i$ detachably attached to the nozzles $70_i$ or tips storing a sample. The liquid storage portion group $27_i$ includes one or two or more liquid storage portions that store at least a magnetic particle suspension and two or more liquid storage portions that store nucleic acid or a fragment thereof and a separation/extraction solution used for the extraction thereof. If necessary, the liquid storage portion group further includes two or more liquid storage portions that store an amplification solution used to amplify nucleic acid and a liquid storage portion that stores a sealing solution for sealing the inside of a PCR tube $231_i$ as a reaction container. Further, each exclusive region $20_i$ includes the sample storage portion $22_i$ that serves as a liquid storage portion which directly or indirectly contacts the ultrasonic vibrator controlled by the ultrasonic vibration device 80 so that an ultrasonic vibration is applied thereto.

Meanwhile, the common region $20_0$ is a region that is provided outside the exclusive region $20_i$ and is provided so that the front end of the main dispensing tip $211_0$ detachably attached to the crossing nozzle $70_0$ as the crossing head passes, and includes a reagent storage portion group $27_0$ that is provided so that the front end is inserted thereinto and a tip storage portion group $21_0$ that stores the dispensing tip $211_0$ detachably attached to the crossing nozzle $70_0$. Then, a reagent stored in the reagent storage portion group $27_0$ may be transferred or supplied to each exclusive region $20_i$ by using the crossing nozzle $70_0$. Alternatively, a product or a produced material stored in each exclusive region may be transferred or stored in the reagent storage portion group $27_0$. Further, a solution of DNA or the like stored in the exclusive region $20_i$ may be dispensed or transferred to the other exclusive regions $20_K$ (k≠i).

Hereinafter, a more specific embodiment of the linear movement type reaction treatment apparatus 10 according to the first embodiment of the invention will be described with reference to FIGS. 2 to 5.

Figure 2:
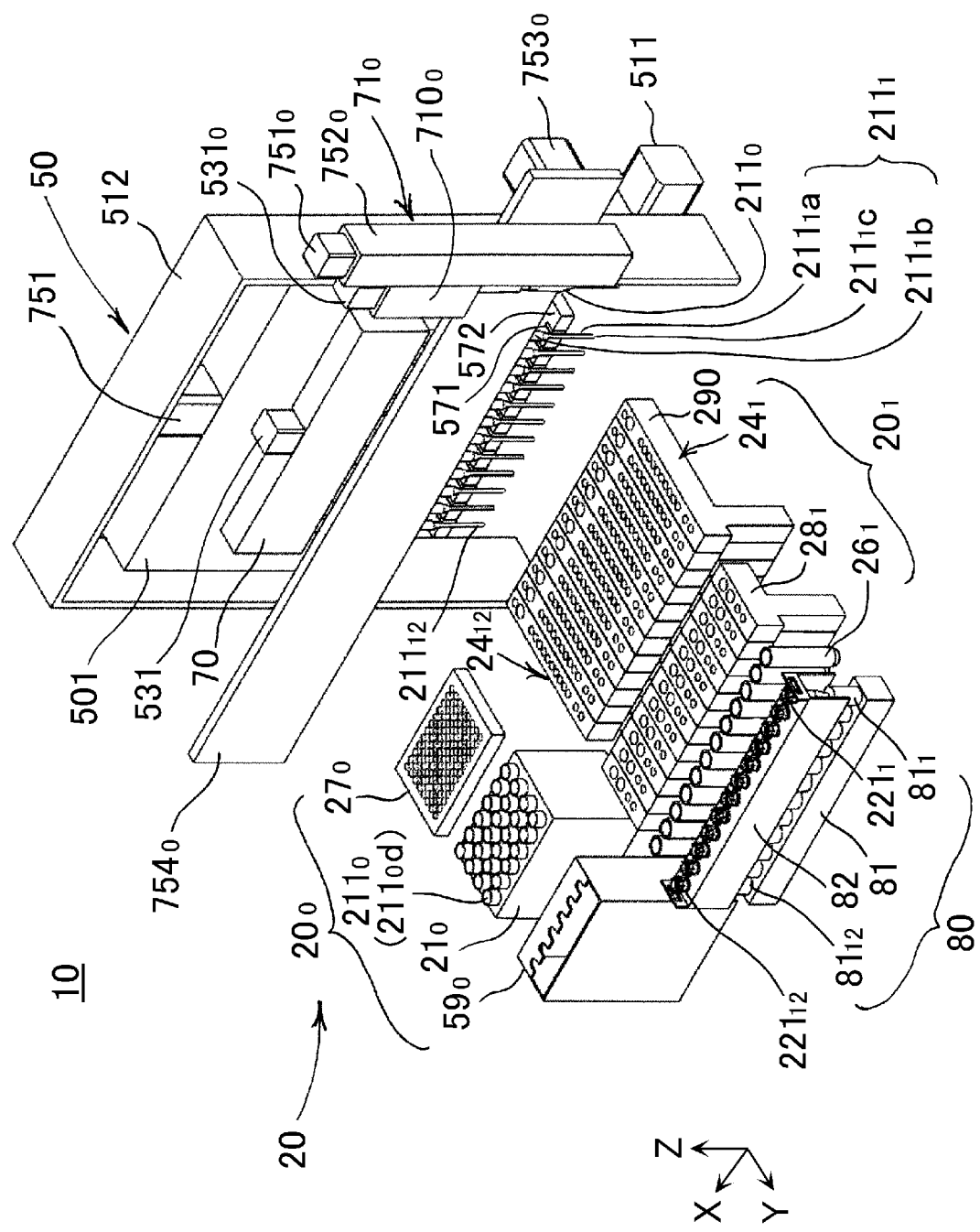
FIG. 2 is an entire perspective view illustrating an example of the linear movement type reaction treatment apparatus according to the first embodiment.

FIG. 2 is an entire perspective view illustrating the linear movement type reaction treatment apparatus 10 according to the embodiment of the invention.

For example, the linear movement type reaction treatment apparatus 10 has a size of about 600 mm in the length direction (the Y-axis direction), the width direction (the X-axis direction), and the height direction (the Z-axis direction). Here, the container group 20, the dispensing head 50 that is movable in the linear arrangement direction (the Y-axis direction) with respect to the container group 20, the dispensing head movement mechanism 51 that moves the dispensing head 50 in the Y-axis direction, the temperature controller 29, and the ultrasonic vibration device 80 are mainly provided on the stage. Furthermore, the operation panel 13 and the CPU+program 60 are provided in a casing (not illustrated) that stores the container group 20 and the dispensing head 50.

The dispensing head 50 includes a base body 501 that is provided so as to be movable in the linear arrangement direction (the Y-axis direction), the nozzle arrangement portion 70 that is provided so that twelve nozzles $71_i$ are arranged at a predetermined pitch (for example, 18 mm) in the X-axis direction so as to be movable in the up and down direction (the Z-axis direction) with respect to the base body 501, twelve dispensing tips $211_i$ that are attached to the nozzles $71_i$, and the crossing nozzle $71_0$ that is equipped with one dispensing tip $211_0$ movable in the crossing direction (the X-axis direction).

The dispensing head movement mechanism 51 includes a Y-axis movement motor 511 and a Y-axis movement frame 512 that is movable in the Y-axis direction by a ball screw or a timing belt driven by the Y-axis movement motor 511.

The base body 501 of the dispensing head 50 supports the nozzle arrangement portion 70 so that the nozzle arrangement portion is movable in the Z-axis direction while being supported by the Y-axis movement frame 512, and is equipped with a Z-axis movement motor 751 that moves the nozzle arrangement portion 70 in the Z-axis direction.

The nozzle arrangement portion 70 includes a cylinder driving plate that drives twelve plungers slidable inside the cylinder communicating with the nozzle and a suction/ejection driving motor 531 that drives the cylinder driving plate. Here, the cylinder driving plate is provided below the nozzle arrangement portion so as to support and arrange the cylinders and the nozzles communicating with the cylinders at the above-described pitch and to suction and eject a gas with respect to the nozzles.

A tip attachment/detachment member is provided below the nozzle arrangement portion 70. Here, the tip attachment/detachment member is horizontally supported to the nozzle arrangement portion 70 by two shafts movable downward while the tip attachment/detachment member is biased upward. Then, the upper end of the shaft is located below the lower limit position of the upward/downward movement range for the normal suction/ejection of the cylinder driving plate although the upper end is located above the upper end of the cylinder. The tip attachment/detachment mechanism 59 is provided which is pressed downward to the vicinity of the upper end of the cylinder so as to move the tip attachment/detachment member downward when the cylinder driving plate moves downward to the vicinity of the upper end of the cylinder beyond the upward/downward movement range. The tip attachment/detachment member includes twelve holes which are provided at the above-described pitch so that the nozzles $71_i$ pass therethrough, and the inner diameter is larger than the outer diameter of the nozzle and is smaller than the attachment portion as the maximum outer diameter of the dispensing tip $211_i$.

The magnetic portion 57 is provided so as to move close to and away from a small-diameter portion $211_i a$ of the dispensing tip $211_i$, and twelve magnets 571 capable of applying or removing a magnetic field to the dispensing tip $211_i$ are provided in a movable body 572 movable in the Y-axis direction.

The crossing nozzle $71_0$ includes a crossing movement body 752 that is attached to the base body 501 or the Y-axis movement frame 512 of the dispensing head 50 and is movable in the X-axis direction by a side plate 754 provided in the X-axis direction, a crossing base body $710_0$ that supports the cylinder and the nozzle, the dispensing tip $211_0$ that is provided in the nozzle provided in the crossing base body $710_0$, a suction/ejection motor $531_0$ that suctions and ejects a gas by driving the plunger of the cylinder provided in the crossing base body $710_0$, a Z-axis driving motor $751_0$ that drives the crossing base body $710_0$ in the up and down direction (the Z-axis direction), and a X-axis driving motor $753_0$ that is provided in the side plate 754. Furthermore, Reference Sign $211_i c$ indicates the front end of the dispensing tip $211_i$, and Reference Sign $211_i b$ indicates a large-diameter portion.

Figure 3:
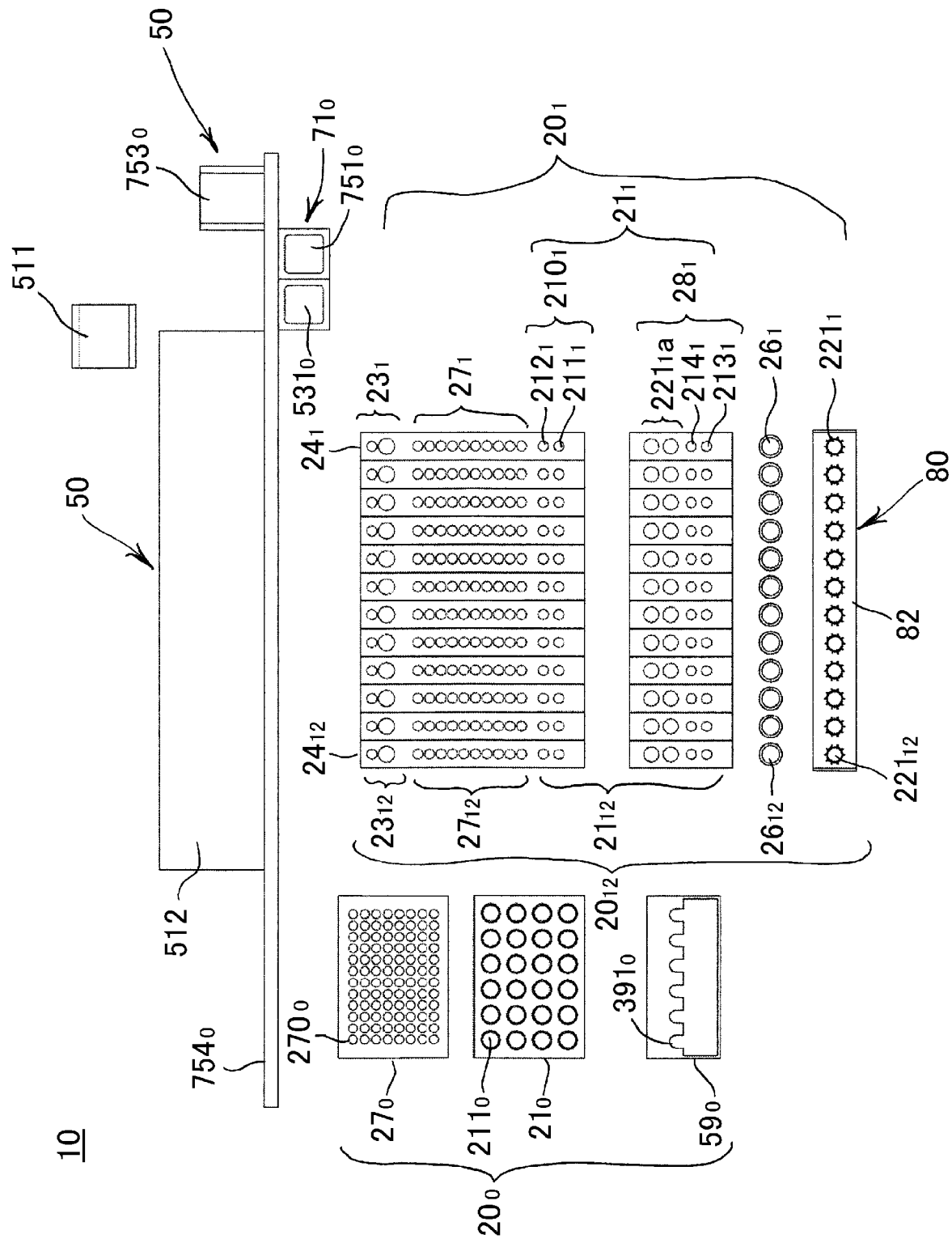
FIG. 3 is a top view illustrating the linear movement type reaction treatment apparatus illustrated in FIG. 2.

As illustrated in FIG. 2 or 3, the common region $20_0$ and the exclusive regions $20_i$ as the container group 20, the ultrasonic vibration device 80, and the temperature controller 29 are provided on the stage other than the dispensing head 50.

The common region $20_0$ includes the reagent storage portion group $27_0$ that is provided as a micro plate with a well $270_0$ of eight rows by twelve columns, a tip storage portion group $21_0$ that stores dispensing tips of four rows by six columns stored so as to be attachable to the crossing nozzle $71_0$, and a dispensing tip attachment/detachment portion $59_0$ that includes a plate provided with a notched portion $591_0$ for attaching or detaching the main dispensing tip $211_0$ attached to the crossing nozzle $71_0$ from the nozzle $71_0$.

In each of twelve exclusive regions $20_i$, a cartridge container $24_i$ in which fourteen reaction containers or various storage portions are arranged in a linear shape, a cartridge container $28_i$ in which four storage portions are arranged in a linear shape, a parent specimen tube $26_i$, and a sample storage portion $221_i$ capable of applying an ultrasonic vibration are arranged in the linear arrangement direction in parallel so that the same storage portions, the reaction containers, and the parent specimen tubes are arranged at the same position in the linear arrangement direction (the Y-axis direction).

Here, the cartridge container $24_i$ includes two reaction container $23_i$ having different capacities, ten prepacked or empty liquid storage portion groups $27_i$, and a tip storage portion group $210_i$ that stores two dispensing tips $211_i$ and $212_i$.

The cartridge container $28_i$ includes a storage portion that stores two scattering prevention lids $221_i a$ and a storage portion that stores punching tips $213_i$ and $214_i$.

Figure 4:
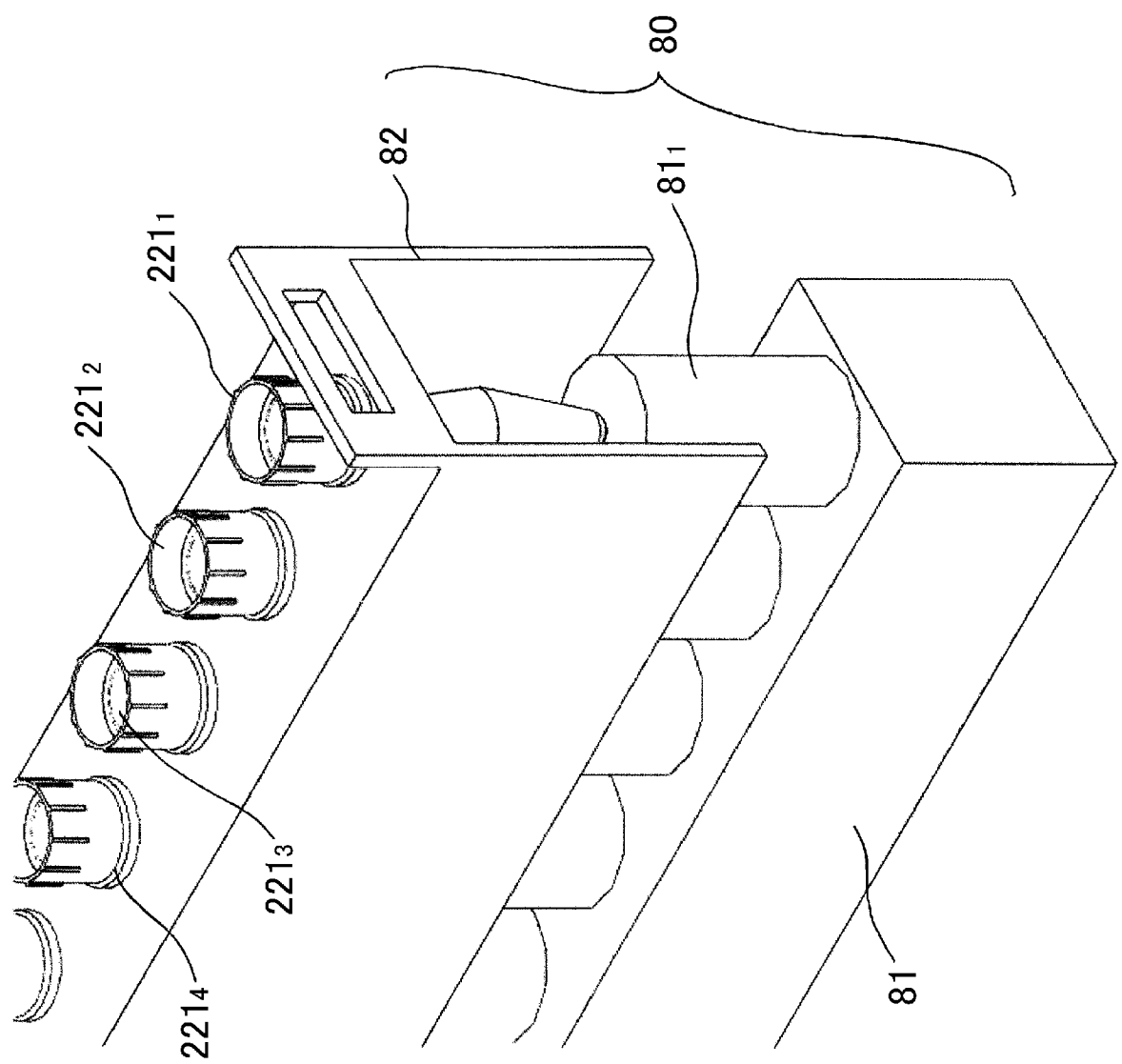
FIG. 4 is an enlarged perspective view illustrating a part of an ultrasonic vibration device illustrated in FIG. 2.
Figure 5:
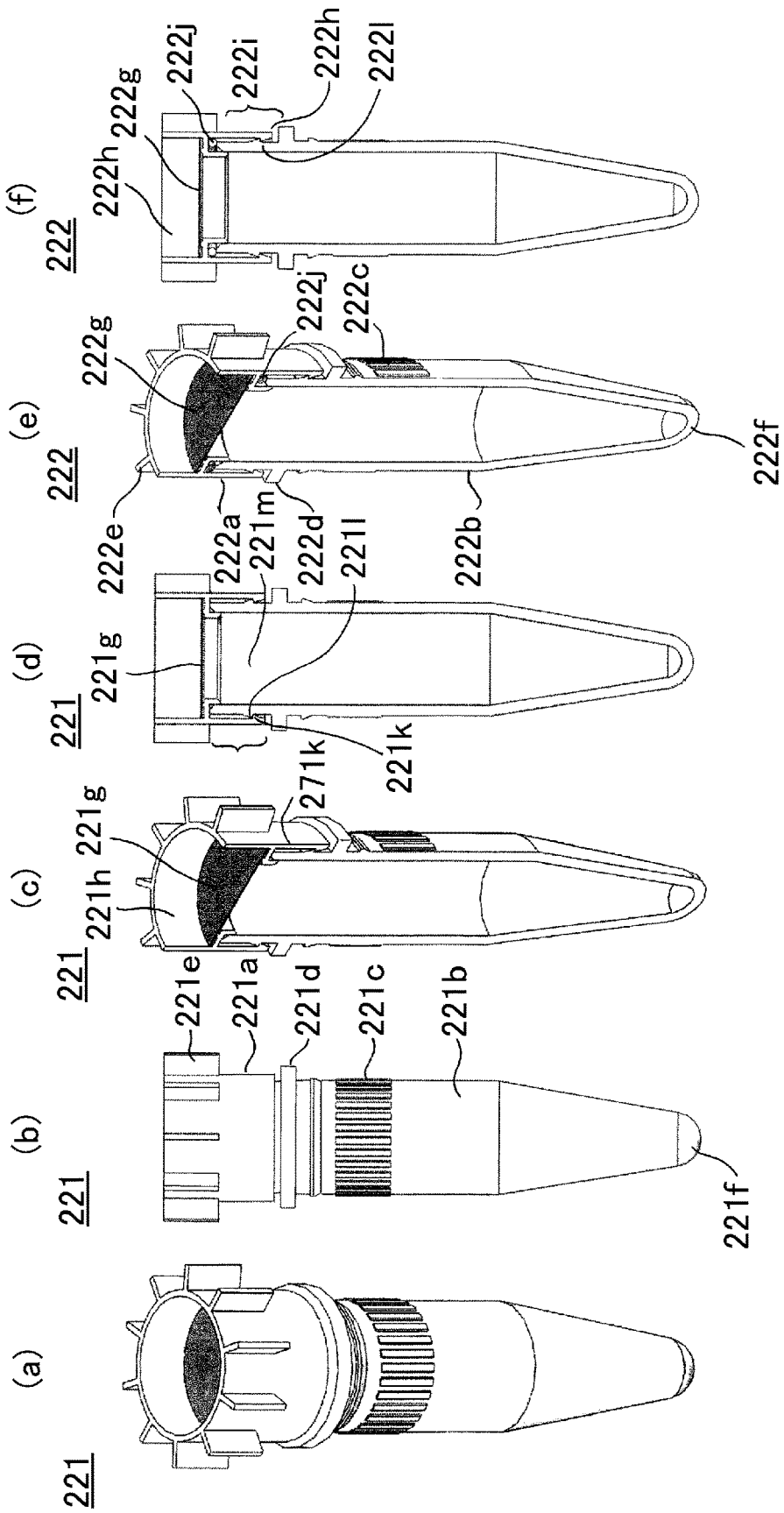
FIGS. 5(a) to 5(f) are enlarged diagrams illustrating a sample storage portion illustrated in FIGS. 2 and 4.
Figure 6:
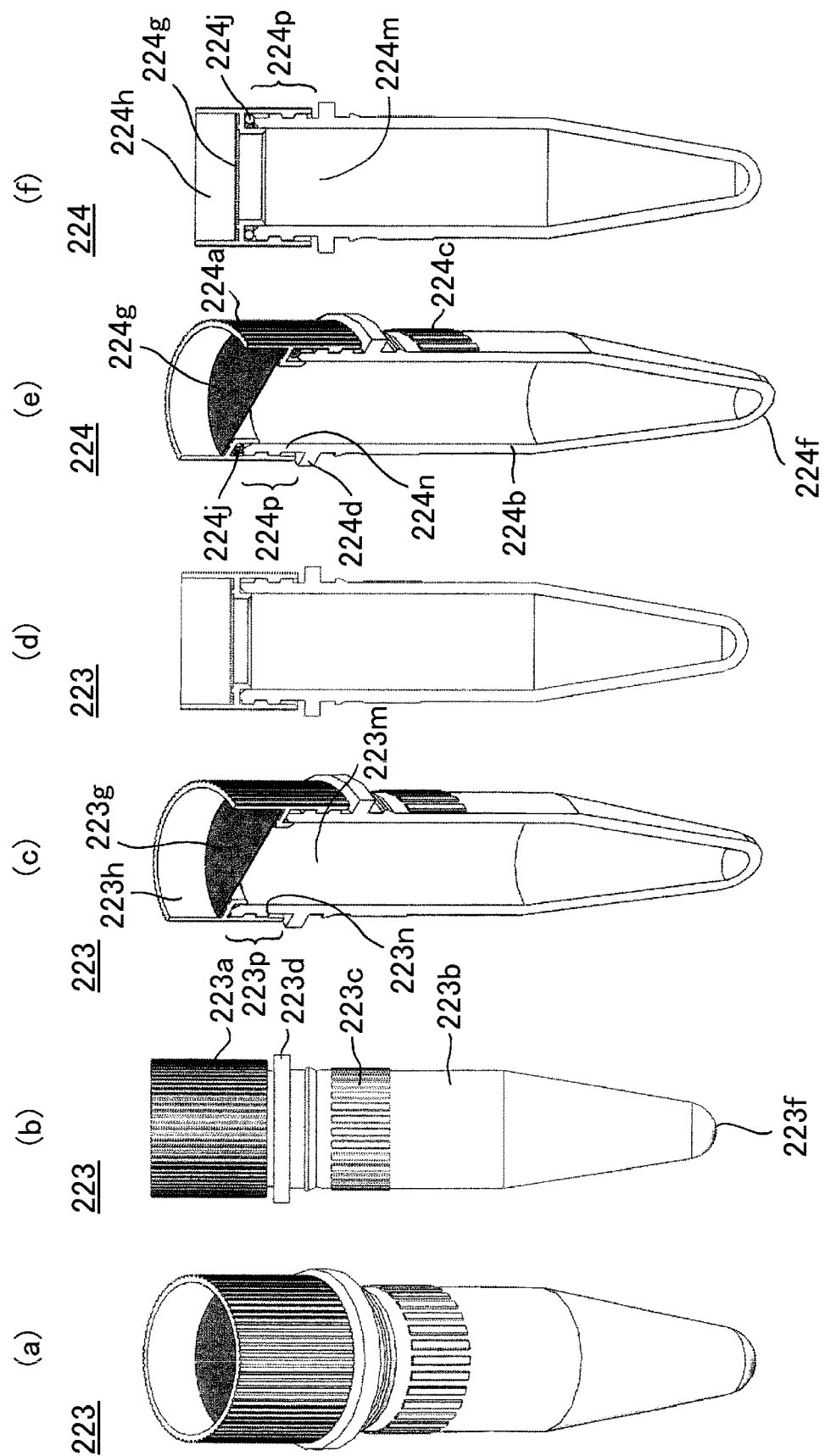
FIGS. 6(a) to 6(f) are diagrams illustrating a sample storage portion according to another embodiment.

FIG. 4 illustrates the ultrasonic vibration device 80 which applies an ultrasonic vibration to the sample storage portion $221_i$ (i=1, 2, . . . , 12) of FIG. 2. The ultrasonic vibration device 80 includes a plurality of (in this example, twelve) horns $81_i$ that is resonated by the vibration of the ultrasonic vibrator and is pressed against the bottom portions of the sample storage portions $221_i$, a vibration source installation portion 81 that includes a plurality of (in this example, twelve) ultrasonic vibrators provided therein, and a sample storage portion support base 82 that includes a plurality of (in this example, twelve) holding holes for holding the sample storage portions $221_i$ and does not directly contact the horns $81_i$ or the ultrasonic vibrators. The vibration source installation portion 81 includes a spring that elastically biases the ultrasonic vibrator and the horn upward in order to press the horn $81_i$ against the bottom portions of the sample storage portions $221_i$. Further, in the sample storage portion support base 82, the sample storage portion $221_i$ is held by the flange $221d$, and for example, a slidable pressing plate (not illustrated) which is detachably attached by the sliding in the horizontal direction is attached to the upper portion of the sample storage portion support base 82 so that the sample storage portion $221_i$ does not protrude upward.

FIGS. 5(a), 5(b), 5(c), and 5(d) specifically illustrate the sample storage portion 221. The sample storage portion 221 includes a main body $221b$ of the storage portion, a slip prevention member $221c$ that is formed on the upper outer surface of the main body, an opening portion $221m$, a scattering prevention lid $221a$ that includes a fitting portion $221h$ fitted to the edge of the opening portion $221m$, a bottom portion $221f$ that contacts the horn $81_i$, the flange $221d$ that holds the sample storage portion 221 in a holding hole punched in the sample storage portion support base 83, and an outer peripheral protrusion $221l$ that is provided in the outer periphery of the vicinity of the opening portion $221m$ of the main body. Further, the scattering prevention lid $221a$ further includes a film $221g$ that is formed so as to define the upper portion of the fitting portion $221h$ and is formed so as to be punchable, an inner peripheral protrusion $221k$ that protrudes inward along the inner periphery of the inner edge of the lid $221a$, a fitting portion $221h$ that is fittable to the nozzle 71 above the film $221g$, and a plurality of (in this example, ten) blade-shaped protrusions $221e$ that is directed outward in the outer peripheral surface and extends in the axial direction, and is used for the detachment from the nozzle 71 by using the tip attachment/detachment mechanism.

FIGS. 5(e) and 5(f) illustrate a sample storage portion 222 according to another embodiment. Here, the main portions respectively corresponding to the portions of the sample storage portion 221 are indicated by the same alphabets, and the description thereof will not be presented. The sample storage portion 222 and the sample storage portion 221 have a different configuration in that an o-ring $222j$ is provided in the scattering prevention lid $222a$ of the sample storage portion 222 so as to improve the sealing property.

When the scattering prevention lids $221a$ and $222a$ are attached once, the outer peripheral protrusion $221l$ and the inner peripheral protrusion $221k$ engage with each other so as not to be separated.

FIGS. 6(a) to 6(f) illustrate sample storage portions 223 and 224 according to another embodiment.

The sample storage portions 223 and 224 are different from the sample storage portions 221 and 222 illustrated in FIGS. 5(a) to 5(f) in that the scattering prevention lids $223a$ and $224a$ are attached by threading instead of fitting. Furthermore, the portions respectively corresponding to the sample storage portions 221 and 222 of FIGS. 5(a) to 5(f) are indicated by the alphabets, and threading portions $223p$ and $224p$ provided with thread ridges $223n$ and $224n$ are provided instead of the fitting portions $221h$ and $222i$ provided with the inner peripheral protrusions $221k$ and $222k$ and the outer peripheral protrusions $221l$ and $222l$.

Next, the operation of the linear movement type reaction treatment apparatus 10 according to the embodiment will be described below.

In step S1, a separation/extraction treatment is started by the operation of a touch panel of the operation panel 13.

Then, in step S2, an extraction control unit 61 that is provided in the CPU+program 60 of the linear movement type reaction treatment apparatus 10 instructs the dispensing head movement mechanism 51 so that the dispensing head 50 and the crossing nozzle 71 provided in the dispensing head are moved in the X-axis direction (perpendicular to the linear arrangement direction within the horizontal plane) and are located above one dispensing tip $211_0$ of the tip storage portion $21_0$ of the common region $20_0$. Then, the nozzle $71_0$ is moved downward so that the dispensing tip $211_0$ is attached to the nozzle. Next, the attached dispensing tip $211_0$ is moved so as to be located on the micro plate of the reagent storage portion group $27_0$, the front end thereof is inserted into the well $270_0$ storing water, various cleaning solutions, and various reagents so as to suction the water, the cleaning solutions, and the reagents, and is moved upward so as to dispense the water, the cleaning solutions, and the reagents to the corresponding storage portions of the exclusive regions $20_i$. Accordingly, various cleaning solutions and various reagents are supplied to a part of the storage portions except for the liquid storage portion prepacked by the reagent. For example, a different amount of water is added to the parent specimen tubes $26_i$ storing the sample suspension of the inspection target and not sufficiently set as a quantitatively equal amount so as to set a quantitatively equal amount.

In step S3, the dispensing head 50 is moved in the Y-axis direction (the linear arrangement direction), is located above the punching tip $213_i$ stored in the tip storage portion $21_i$ of the cartridge container $28_i$, and is moved downward so as to attach the punching tip $213_i$ thereto. Then, the punching tip $213_i$ attached to the nozzle $71_i$ is located above the original liquid storage portion of the liquid storage portion group $27_i$ of the container group 20, and the nozzle $71_i$ is moved downward by the nozzle Z-axis movement mechanism 75 so as to punch the film coating the opening portion of the liquid storage portion. In the same way, the dispensing head 50 is moved in the Y-axis direction so as to sequentially punch the reaction container group $23_i$ and the other liquid storage portions of the liquid storage portion group $27_i$.

In step S4, the dispensing head is moved to the cartridge container $28_i$, and the punching tip $213_i$ is detached inside the original storage portion. Each nozzle $71_i$ is moved to the tip storage portion $210_i$ of the cartridge container $24_i$ in the Y-axis direction, and is moved downward by the nozzle Z-axis movement mechanism 75 so as to attach the dispensing tip $211_i$ thereto. Next, the nozzle is moved upward by the nozzle Z-axis movement mechanism 75. Then, the dispensing tip $211_i$ is moved in the Y axis along with the dispensing head 50 by the dispensing head movement mechanism 51, and is moved toward the eighth liquid storage portion of the liquid storage portion group $27_i$ so as to suction a predetermined amount of isopropanol from the liquid storage portion. Subsequently, the dispensing tip is moved again in the Y axis so as to dispense a predetermined amount of isopropanol to each of the solution components (solution of NaCl and SDS) stored in the third liquid storage portion and the fifth liquid storage portion and the distilled water stored in the sixth liquid storage portion. Accordingly, 500 µL of a combination buffer solution (NaCl, SDS, and isopropanol), 700 µL of a first cleaning solution (NaCl, SDS, and isopropanol), and 700 µL of a second cleaning solution (water of 50% and isopropanol of 50%) are respectively prepared in the third, fifth, and sixth liquid storage portions as the separation/extraction solution.

In step S5, the dispensing head is moved to the parent specimen tube $26_i$ storing a parent specimen, and the front end of the small-diameter portion $211_i$a of the dispensing tip $211_i$ is moved downward by using the nozzle Z-axis movement mechanism 75 so as to be inserted thereinto. Then, the driving plate of the suction/ejection mechanism 53 is moved upward and downward so as to repeat the suction/ejection with respect to the sample suspension stored in the parent specimen tube $26_i$. In this way, the sample is suspended in the solution, and the sample suspension is suctioned into the dispensing tip $211_i$. Then, the dispensing tip having the sample suspension suctioned thereto moves in the Y axis by the dispensing head movement mechanism 51, and the front end thereof is inserted into the sample storage portion $221_i$ so as to eject the sample suspension thereto. Subsequently, the dispensing tip $211_i$ is detached in the tip storage portion $210_i$ by the tip attachment/detachment portion. Then, the dispensing head moves to the cartridge container $28_i$ storing the scattering prevention lid $221_i$a so as to attach the scattering prevention lid $221_i$a to the front end of the nozzle. Subsequently, the dispensing head moves to the upside of the sample storage portion $221_i$ and moves downward so as to fit the scattering prevention lid $221_i$a to the opening portion of $221_i$m of the sample storage portion $221_i$. Then, the scattering prevention lid $221_i$a is detached from the nozzle by using the tip attachment/detachment mechanism so as to seal the sample storage portion $221_i$, and the sample storage portion $221_i$ is vibrated by the ultrasonic vibration device 80 so as to extract a sample, for example, a target material inside bacteria by crushing the bacteria in the solution.

Next, the nozzle is moved to the cartridge container $28_i$ again, is moved to the upside of the punching tip $213_i$, and is downward. Then, when the nozzle having the punching tip 213 attached thereto moves to the upside of the sample storage portion $221_i$, the nozzle moves downward so as to punch the scattering prevention lid $221_i$a. The punching tip is detached in the predetermined storage portion of the cartridge container 28, and the dispensing tip $211_i$ is attached to the nozzle so as to suction the sample suspension. Then, the dispensing head is moved to the first liquid storage portion of the liquid storage portion group $27_i$ storing Lysis1 (enzyme) as a separation/extraction solution, the small-diameter portion $211_i$a of the dispensing tip $211_i$ is inserted through the punched hole of the film. Then, the suction/ejection is repeated in order to mix the sample suspension and the Lysis1.

In step S6, the total amount of the mixed solution is suctioned by the dispensing tip $211_i$, and is incubated while being stored in the reaction container $23_i$ as the reaction tube held by the holding hole set to 55° C. by a constant temperature controller 290. Accordingly, the protein contained in the sample is broken into low molecules. After a predetermined time elapses, the dispensing tip $211_i$ is moved to the second liquid storage portion of the liquid storage portion group $27_i$ by the dispensing head movement mechanism 51 while the reaction solution is left in the reaction tube. Then, the total amount of the solution stored in the second liquid storage portion is suctioned by the nozzle Z-axis movement mechanism 75 and the suction/ejection mechanism 53 and is transferred by using the dispensing tip $211_i$ and the dispensing head movement mechanism 51. Subsequently, the small-diameter portion is inserted into the third liquid storage portion through the hole of the film so as to eject the reaction solution thereto.

In step S7, the reaction solution is mixed with the combination buffer solution as the separation/extraction solution stored in the third liquid storage portion so that the solubilized protein is dewatered and nucleic acid or a fragment thereof is dispersed in the solution.

In step S8, the small-diameter portion of the dispensing tip $211_i$ is inserted into the third liquid storage portion through the hole of the film so as to suction the total amount thereof. Then, the dispensing tip $211_i$ is moved upward by the nozzle Z-axis movement mechanism 75 so that the reaction solution is transferred to the fourth liquid storage portion and the reaction solution is mixed with the magnetic particle suspension stored in the fourth liquid storage portion. A cation structure is formed so that Na+ is combined with a hydroxyl group formed on the surfaces of the magnetic particles contained in the magnetic particle suspension. For that reason, DNA charged negatively is captured by the magnetic particles.

In step S9, the magnet 571 of the magnetic portion 57 moves close to the small-diameter portion $211_i$a of the dispensing tip $211_i$ so that the magnetic particles are adsorbed to the inner wall of the small-diameter portion $211_i$a of the dispensing tip $211_i$. In a state where the magnetic particles are adsorbed to the inner wall of the small-diameter portion $211_i$a of the dispensing tip $211_i$, the nozzle is moved upward by the nozzle Z-axis movement mechanism 75. Then, the dispensing tip $211_i$ is moved from the fourth liquid storage portion to the fifth liquid storage portion by using the dispensing head movement mechanism 51, and is inserted into the small-diameter portion $211_i$a through the hole of the film.

In a state where the magnetic field inside the small-diameter portion $211_i$a is removed when the magnet 571 of the magnetic portion 57 is separated from the small-diameter portion $211_i$a of the dispensing tip $211_i$, the first cleaning solution (NaCl, SDS, and isopropanol) stored in the fifth liquid storage portion is repeatedly suctioned and ejected so that the magnetic particles are separated from the inner wall and the protein is cleaned by the mixing in the first cleaning solution. Subsequently, in a state where the magnetic particles are adsorbed to the inner wall of the small-diameter portion $211_i$a when the magnet 571 of the magnetic portion 57 is moved close to the small-diameter portion $211_i$a of the dispensing tip $211_i$ again, the dispensing tip $211_i$ is moved from the fifth liquid storage portion to the sixth liquid storage portion by the nozzle Z-axis movement mechanism 75 and the dispensing head movement mechanism 51.

In step S10, the small-diameter portion $211_i$a of the dispensing tip $211_i$ is inserted through the hole of the film by using the nozzle Z-axis movement mechanism 75. In a state where the magnetic field inside the small-diameter portion $211_i$a is removed when the magnet 571 of the magnetic portion 57 is separated from the small-diameter portion $211_i$a of the dispensing tip $211_i$, the second cleaning solution (isopropanol) stored in the sixth liquid storage portion is repeated suctioned and ejected, the magnetic particles are mixed in the solution, NaCl and SDS are removed, and the protein is cleaned. Subsequently, in a state where the magnetic particles are adsorbed to the inner wall of the small-diameter portion $211_i$a when the magnet 571 of the magnetic portion 57 is moved close to the small-diameter portion $211_i$a of the dispensing tip $211_i$ again, the dispensing tip $211_i$ is moved upward by the nozzle Z-axis movement mechanism 75, and is moved from the sixth liquid storage portion to the seventh liquid storage portion storing the distilled water by the dispensing head movement mechanism 51.

In step S11, the small-diameter portion $211_i$a of the dispensing tip $211_i$ is moved downward through the hole by the nozzle Z-axis movement mechanism 75, and the distilled water is repeatedly suctioned and ejected at a slow flow rate while the magnetic force is applied to the small-diameter portion $211_i$a of the dispensing tip $211_i$, so that the second cleaning solution (isopropanol) is removed while being replaced with water. Subsequently, in a state where the magnetic force is removed when the magnet 571 of the magnetic portion 57 is separated from the small-diameter portion $211_i$a of the dispensing tip $211_i$, the magnetic particles are mixed while being repeated suctioned and ejected in the distilled water as the dissociated solution, and nucleic acid held by the magnetic particles or a fragment thereof is dissociated (eluted) from the magnetic particles into the solution. Subsequently, the magnet 571 is moved close to the small-diameter portion $211_i$a of the dispensing tip $211_i$ so as to apply a magnetic field into the small-diameter portion, so that the magnetic particles are adsorbed to the inner wall and a solution containing the extracted nucleic acid is left inside the eighth liquid storage portion. The dispensing tip $211_i$ is moved to the storage portion that stores the dispensing tip $211_i$ of the tip storage portion group $21_i$ by the dispensing head movement mechanism 51, and the dispensing tip $211_i$ is detached from the nozzle $71_i$ along with the magnetic particles inside the storage portion while adsorbing the magnetic particles through a detachment member 591 of the tip attachment/detachment mechanism 59.

In the linear movement type reaction treatment apparatus 10 according to the embodiment, a shell of bacteria as a sample in a sample suspension is extracted by applying an ultrasonic vibration thereto, a target material therein is extracted in the solution, and a protein is solubilized while being mixed with a separation/extraction solution. Accordingly, the nucleic acid as a target material may be separated and extracted certainly with high reliability and efficiency.

Figure 7:
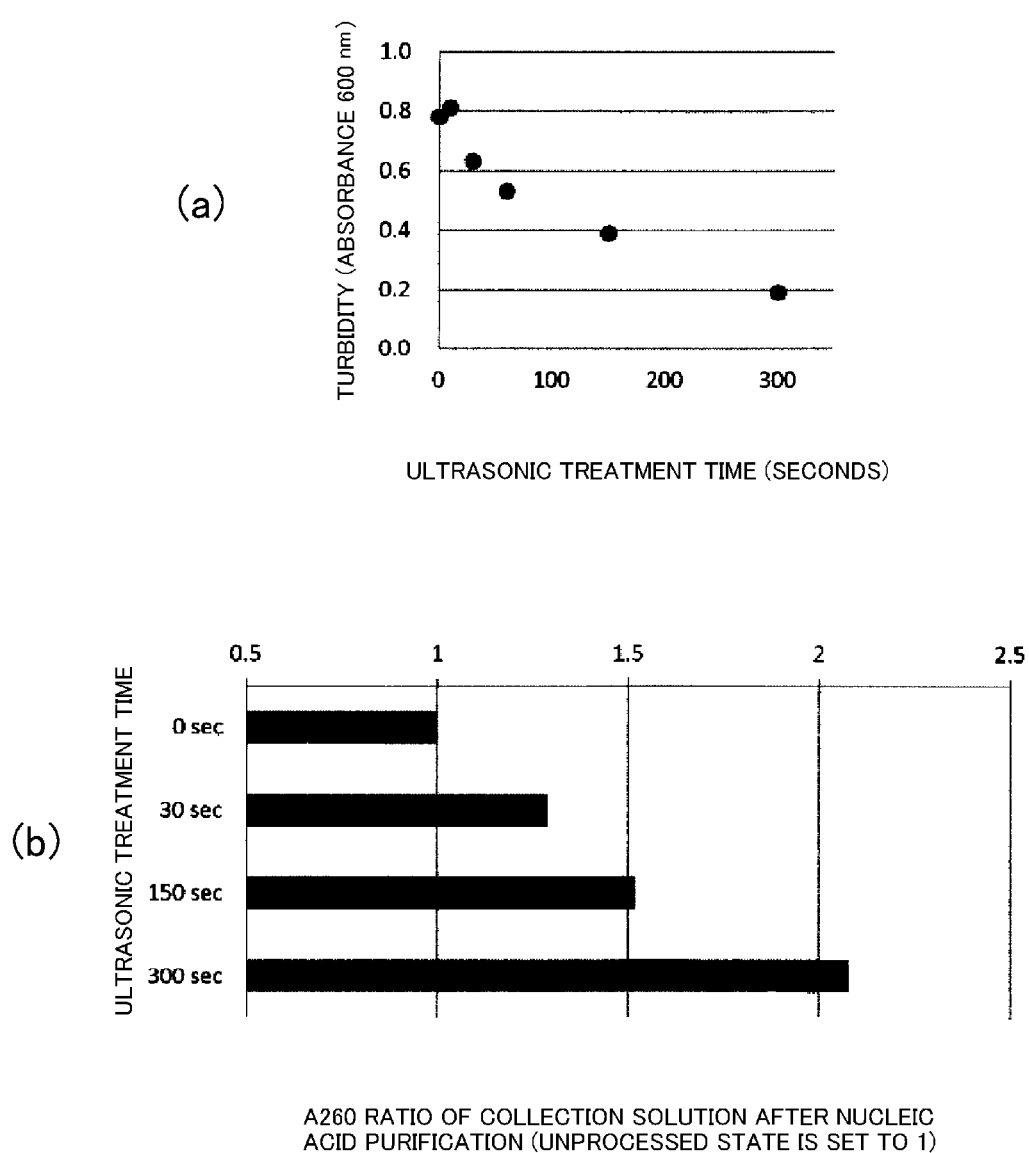
FIGS. 7(a) and 7(b) are graphs illustrating a test result of ultrasonic vibration treatment that uses the linear movement type reaction treatment apparatus illustrated in FIG. 2.

FIGS. 7(a) and 7(b) are two graphs illustrating a test result for evaluating a correlation of a bacteria crushing state and a bacteria DNA collection amount by ultrasonic vibration treatment using an apparatus corresponding to the linear movement type reaction treatment apparatus according to the embodiment.

FIG. 7(a) is a graph illustrating a test result of an ultrasonic vibration treatment time and a crushing degree for a colon bacillus. In this test, 300 μL of a colon bacillus nutrient medium (E. coli JM109, nutrient medium: LB medium) was dispensed to each of 1.5 mL of six sample storage portions and the sample storage portions were subjected to a centrifugal separation (in a condition of 1000 g, 5 minutes, and a room temperature). After the centrifugal separation, a supernatant was removed, and a pellet was suspended by 300 μL of a normal saline solution. By using an ultrasonic vibration device, ultrasonic vibration treatment was performed at the output of 200 W. In a case of treatment of 30 seconds or more, a condition was set so that the output was continued for 30 seconds and was stopped for 30 seconds as a repeated cycle. Further, six sample storage portions were prepared in total by using 1.5 μL of a dummy enclosed by 300 μL of a normal saline solution. The treatment time (the total output time) was set to 10, 30, 60, 150, and 300 seconds. After the ultrasonic treatment, the turbidity (absorbance of a wavelength of 600 nm) for the solutions subjected and not subjected to the treatment was measured by NanoDrop.

FIG. 7(b) is a graph illustrating the collection efficiency for a colon bacillus DNA using ultrasonic vibration treatment. Here, 200 μL was sampled from the solutions (samples subjected to the treatment for 30 seconds, 150 seconds, and 300 seconds) subjected and not subjected to the vibration treatment, and a DNA purification operation was performed by using this apparatus. The obtained collection solution was measured by NanoDrop, and the absorbance of a wavelength of 260 nm as an index representing the absorbance originated from nucleic acid was measured.

From the above-described result, as illustrated in FIG. 7(a), it was proved that the transparency was improved when the turbidity decreased in accordance with the length of the ultrasonic vibration treatment time based on the transparency of the actually obtained solution.

In FIG. 7(b), the absorbance of a wavelength of 260 nm originated from DNA obtained from a sample not subjected to the ultrasonic treatment is 1.493 (a value which is converted into the length of 1 cm since NanoDrop has an optical path length of 1 mm) in terms of DNA purification treatment, and the absorbance ratio of the collection solutions is illustrated by setting the value as 1. The absorbance increased in response to the length of the ultrasonic vibration treatment time, and the absorbance values of 1.5 times and 2 times or more were obtained by the treatment time of 150 seconds and 300 seconds. From this result, the ultrasonic vibration treatment has an effect of crushing the cell membrane of the colon bacillus, and hence the DNA extraction efficiency is improved by extracting or releasing the DNA to the outside of the cell.

Figure 8:
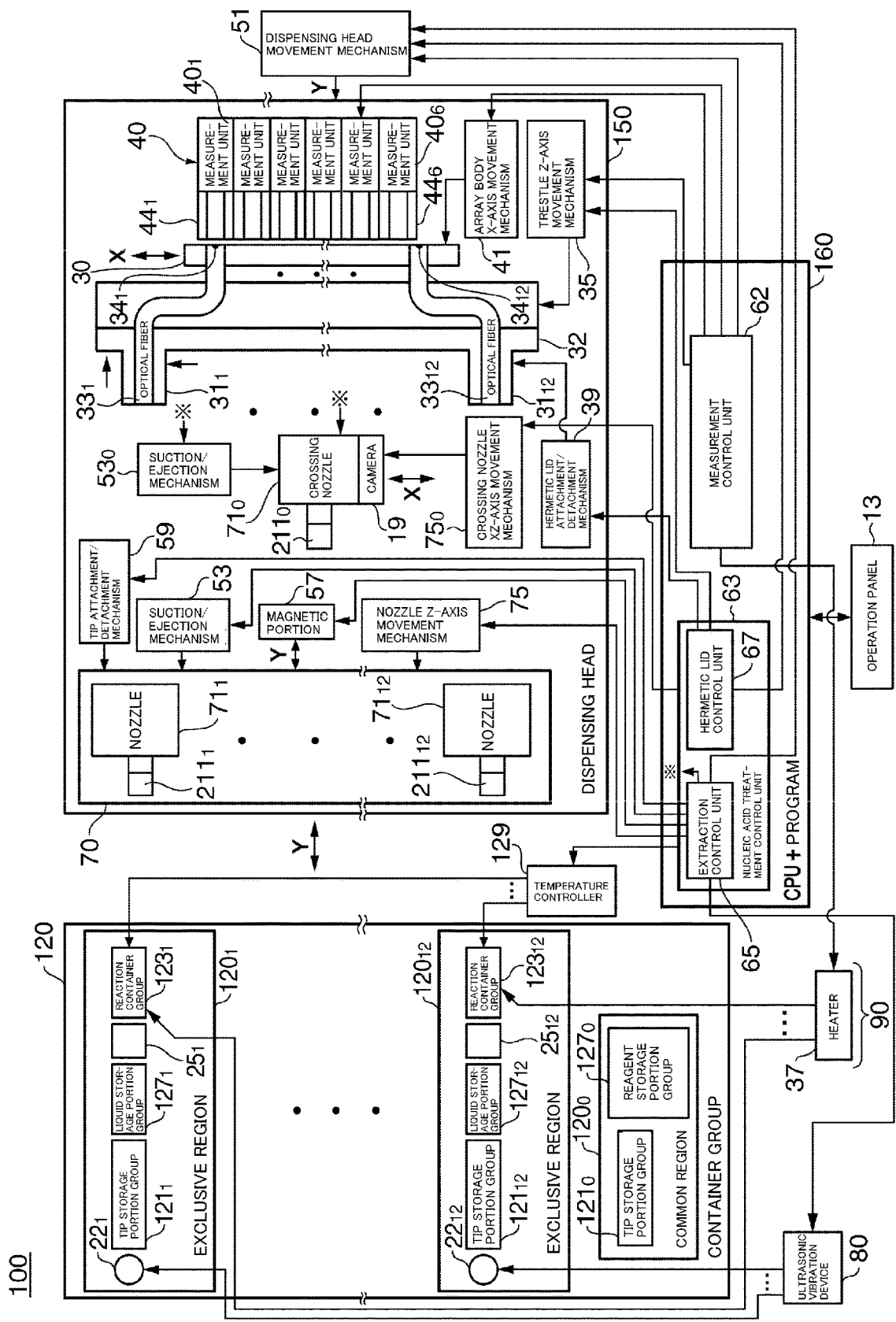
FIG. 8 is an entire block diagram illustrating a linear movement type reaction treatment apparatus according to a second embodiment of the invention.

FIG. 8 is a block diagram illustrating a linear movement type reaction treatment apparatus 100 according to a second embodiment. Furthermore, since the same reference sign as the reference sign used in the linear movement type reaction treatment apparatus 10 according to the first embodiment indicates the same or similar component (only having a different size), the description will not be repeated.

The linear movement type reaction treatment apparatus 100 includes a container group 120 that includes a common region $120_0$ and a plurality of (in this example, twelve) exclusive regions $120_i$ (i=1, . . . , 12, omitted below), a dispensing head 150 that includes a nozzle arrangement portion 70 in which a plurality of (in this example, twelve) nozzles $71_i$ respectively and detachably equipped with dispensing tips $211_i$ provided so that the front ends thereof are insertable into reaction containers respectively provided in the exclusive regions $120_i$ and the liquid storage portions thereof and a crossing nozzle $71_0$ which is movable so as to cross the entire exclusive region $120_i$ and is detachably equipped with a dispensing tip $211_0$ provided so that the front end thereof is insertable into the liquid storage portions provided in the exclusive regions $120_i$ and the common region $120_0$, and a magnetic portion 57 that is provided in the dispensing head 150 and gives an influence of a magnetic field to the dispensing tip $211_i$ attached to the nozzle arrangement portion 70. The crossing nozzle 71 corresponds to the "crossing head".

The linear movement type reaction treatment apparatus 10 further includes a dispensing head movement mechanism 51 that serves as a "linear movement mechanism" which moves the dispensing head 150 in the Y-axis direction as the linear arrangement direction, a temperature controller 129 which controls the temperature of the reaction container group $123_i$ in each exclusive region $120_i$, an ultrasonic vibration device 80 that controls an ultrasonic vibrator for applying an ultrasonic vibration to the sample storage portion 22 in each exclusive region $120_i$, a heater 37 that serves as a heating unit for heating the reaction container, a CPU+program 160 that is configured as a CPU, ROM, RAM, and various memories and realizing a communication function via a LAN or the like, and a program stored in the ROM and the like, and an operation panel 13 that is a liquid crystal display including a display unit or an operation unit such as an operation key or a touch key.

In the embodiment, the dispensing head 150 further includes a light guiding trestle 32 that includes a plurality of (in this example, twelve) link portions $31_i$ directly or indirectly linked to the opening portions of the reaction containers and provided with the front ends of two or more flexible light guiding portions optically connected to the inside of the linked reaction containers and a measurement unit 40 that is fixed to the dispensing head 150.

The dispensing head 150 includes a trestle Z-axis movement mechanism 35 that corresponds to the "vertical movement mechanism" of the light guiding trestle 32 and moves the light guiding trestle 32 in the Z-axis direction with respect to the container group 120 independently from the nozzle arrangement portion 70. The trestle movement mechanism corresponds to the dispensing head movement mechanism and the trestle Z-axis movement mechanism 35.

The dispensing head 150 further includes a connection end array body 30 that integrally arranges and supports a plurality of (in this example, twelve) connection ends $34_i$ provided to correspond to the link portions $31_i$ and provided with the rear ends of the optical fibers (bundle) 33 serving as the light guiding portions and having the front ends provided in the link portions $31_i$ at a gap narrower than the gap between the link portions $31_i$ in a predetermined path (in this example, a linear path provided in the X-axis direction) provided on a vertical plane as an arrangement surface. Further, the connection end array body 30 is provided at a position distant from the light guiding trestle 32 or the reaction container group $23_i$.

The measurement unit 40 includes six kinds of specific wavelength measurement units $40_j$ (j=1, . . . , 6, omitted below) that respectively receive light of specific wavelengths or specific wavelength bands of six kinds of fluorescence and emit excitation light of six kinds of specific wavelengths or specific wavelength bands for the emission of light of fluorescence.

Figure 10:
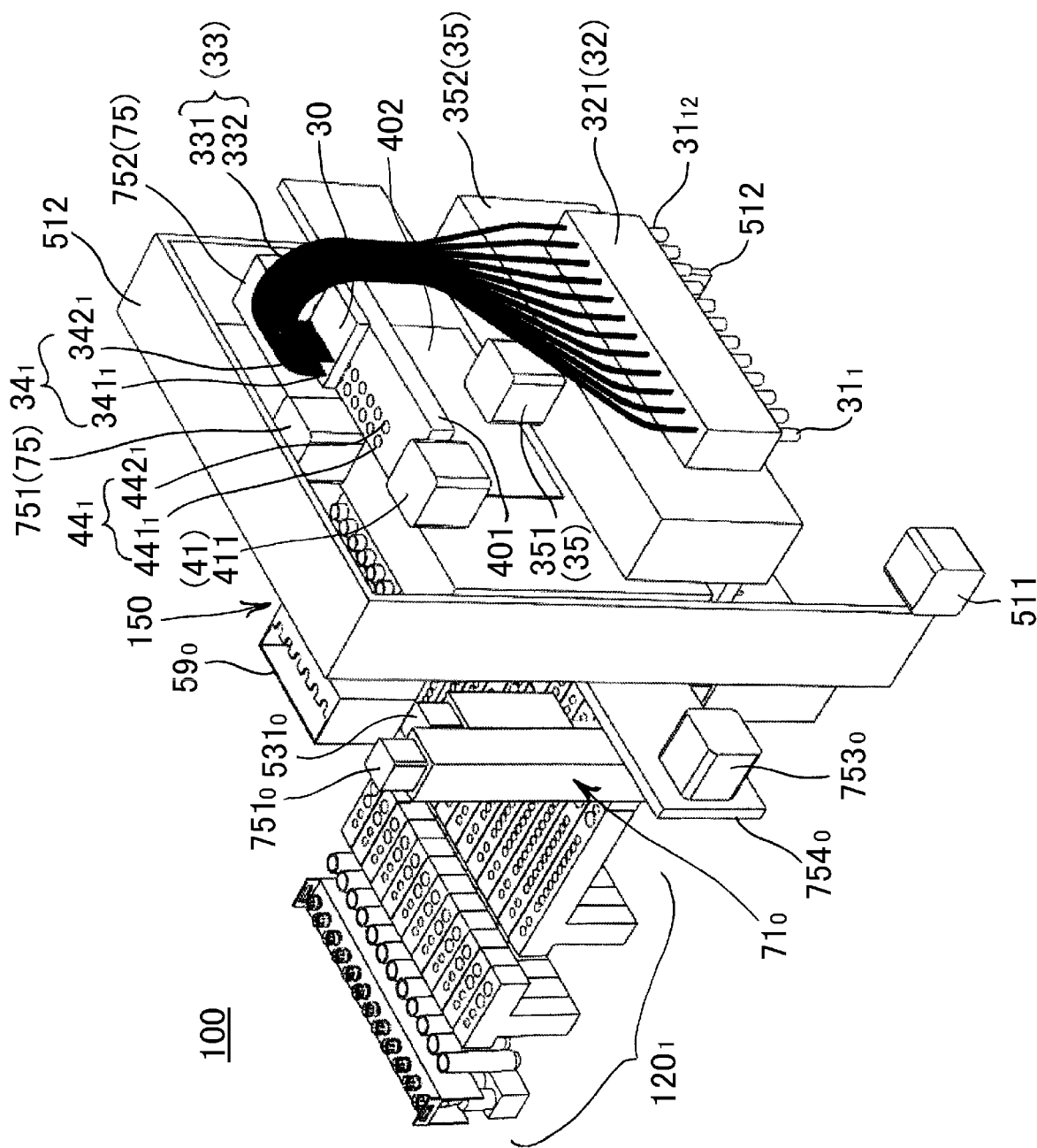
FIG. 10 is an entire perspective view illustrating the linear movement type reaction treatment apparatus of FIG. 9 when viewed from the rear side thereof.

Each specific wavelength measurement unit $40_i$ includes a measurement end $44_j$ that is provided so as to be adjacent to the arrangement surface or to contact the arrangement surface and sequentially connects each connection end $34_i$ to the predetermined path (the linear path formed in the X-axis direction). In the embodiment of FIG. 10 to be described later, each connection end $34_i$ includes a first connection end $341_i$ (which guides the light received from the link portion to the light receiving portion) and a second connection end $342_i$ (which guides the light from the light emitting source to the link portion), and each measurement end $44_j$ includes a first measurement end $441_j$ and a second measurement end $442_j$ which are optically connected to the connection ends $341_i$ and $342_i$ while being arranged in the Y-axis direction (the linear arrangement direction). The first measurement end $441_j$ is optically connected to a photoelectric element such as a photomultiplier tube as a light receiving portion provided in each specific wavelength measurement unit $40_j$ and the second measurement end $442_j$ is optically connected to the light emitting source provided in the specific wavelength measurement unit $40_j$.

Further, the dispensing head 150 includes an array body X-axis movement mechanism 41 that serves as a light guiding-converting mechanism which moves the connection end array body 30 on the dispensing head 150 in the X-axis direction (the crossing direction) so as to sequentially connect each of the connection ends $34_i$ arranged in the connection end array body 30 and each of the measurement ends $44_j$.

The container group 120 includes a plurality of (in this example, twelve) exclusive regions $120_i$ that respectively corresponds the nozzles so that one (in this example, one set corresponds to one) nozzle enters and the nozzles do not enter. Each exclusive region $120_i$ includes a liquid storage portion group $127_i$ that includes a plurality of storage portions storing or capable of storing a reagent solution, a hermetic lid storage portion $25_i$ that stores or is capable of storing one or two or more translucent hermetic lids $251_i$ detachably attached to the link portion $31_i$, and a tip storage portion group $121_i$ that stores a sample or a plurality of dispensing tips $211_i$ detachably attached to the nozzles. The liquid storage portion group $127_i$ includes one or two or more liquid storage portions that store at least a magnetic particle suspension and two or more liquid storage portions that store a separation/extraction solution used to separate and extract nucleic acid and a fragment thereof. Further, the liquid storage portion group includes two or more liquid storage portions that store an amplification solution used to amplify nucleic acid and a liquid storage portion that stores a sealing solution for sealing the amplification solution stored in the PCR tube $231_i$ as the reaction container in the PCR tube $231_i$. Here, these components are arranged in a linear shape in the Y-axis direction (the linear arrangement direction) as the length direction thereof.

Furthermore, it is desirable to display barcodes as a sample information item and an inspection information item for identifying the exclusive regions $120_i$ in the exclusive regions $120_i$. Further, the dispensing head 150 includes one crossing nozzle $71_0$ capable of transferring or dispensing a solution while crossing the exclusive region $120_i$ (moving in the X-axis direction), and a suction/ejection is performed by a crossing nozzle suction/ejection mechanism $53_0$ different from the suction/ejection mechanism 53. Accordingly, a solution of DNA or the like stored in the exclusive region $120_i$ may be dispensed or transferred to the other exclusive regions $120_K$ ($k \neq i$).

The CPU+program 160 includes at least a nucleic acid treatment control unit 63 that generates an instruction of a series of treatment for an extraction, an amplification, and a sealing of an amplification solution for nucleic acid or a fragment thereof with respect to the temperature controller 129, the dispensing head movement mechanism 51, the tip attachment/detachment mechanism 59, the suction/ejection mechanisms 53 and $53_0$, the magnetic portion 57, the nozzle Z-axis movement mechanism 75, the hermetic lid attachment/detachment mechanism 39, and the crossing nozzle XZ-axis movement mechanism $75_0$, and also includes a measurement control unit 62 that instructs a measurement using the measurement unit $40_j$ by controlling the array body Y-axis movement mechanism 41 so that the optical fibers (bundle) $33_i$ as the light guiding portions of the link portions $31_i$ are optically connected to the first measurement end $441_j$ and the second measurement end $442_j$ of the measurement end $44_j$ of the measurement unit $40_j$ after the dispensing head movement mechanism 51 and the trestle Z-axis movement mechanism 35 are controlled so that the link portions $31_i$ are indirectly or directly linked to the opening portions a plurality of (in this example, twelve) PCR tubes $231_i$.

Further, the nucleic acid treatment control unit 63 includes an extraction control unit 65 and a hermetic lid control unit 67, and the extraction control unit 65 includes the extraction control unit 65 that generates an instruction of a series of treatment for an extraction of nucleic acid or a fragment thereof with respect to the tip attachment/detachment mechanism 59, the suction/ejection mechanism 53, the magnetic portion 57, the nozzle Z-axis movement mechanism 75, the dispensing head movement mechanism 51, and the trestle Z-axis movement mechanism 35 and the hermetic lid control unit 67 that generates an instruction for a sealing treatment using the hermetic lid with respect to the trestle Z-axis movement mechanism 35 and the dispensing head movement mechanism 51. The reaction container $23_i$, the temperature controller 129, and the heater 37 correspond to a reaction container control system 90.

FIGS. 9 to 12 illustrate a more specific embodiment of the linear movement type reaction treatment apparatus 100 according to the second embodiment.

Figure 9:
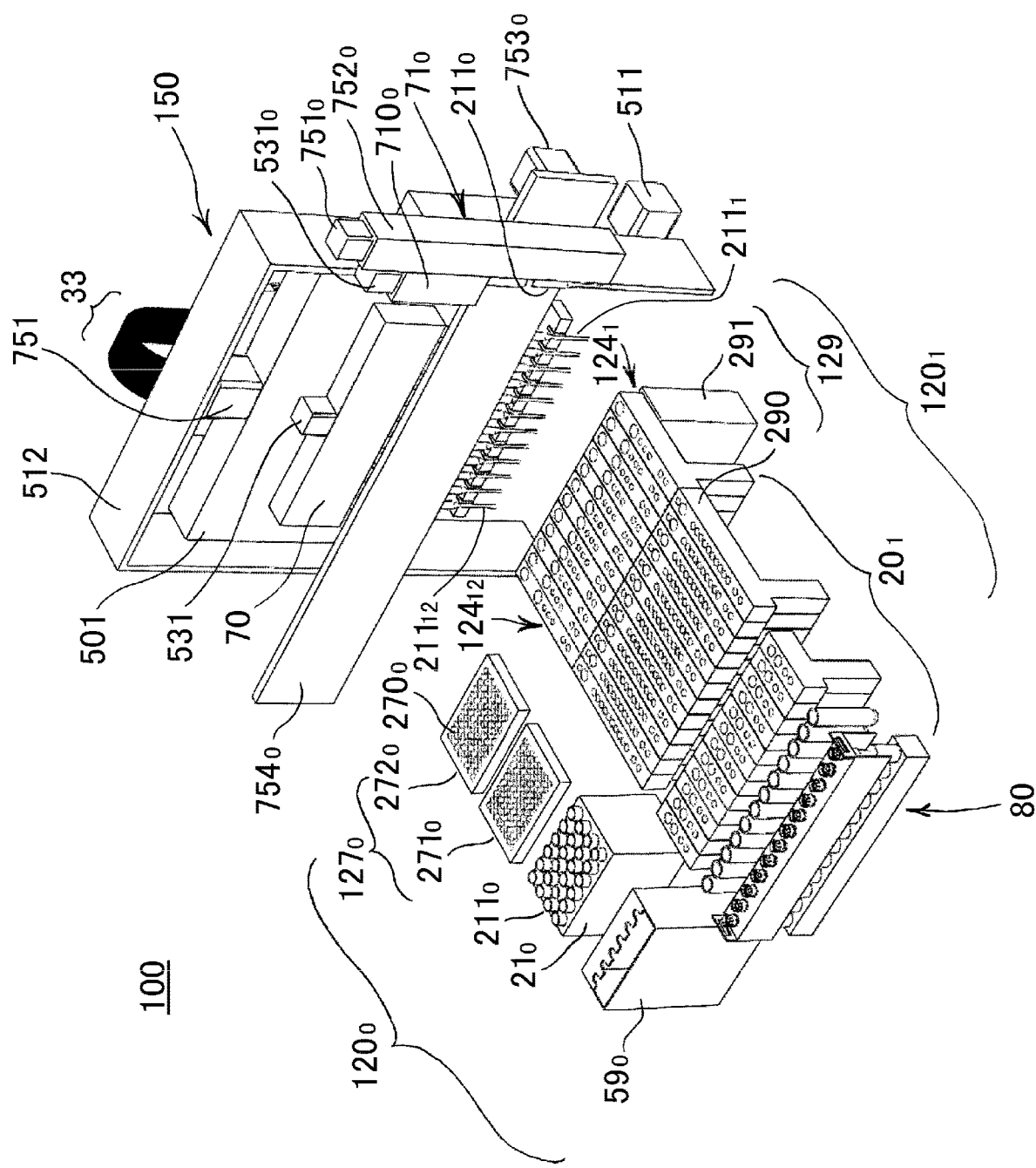
FIG. 9 is an entire perspective view illustrating an example of the linear movement type reaction treatment apparatus according to the second embodiment.

FIG. 9 is a schematic perspective view of the linear movement type reaction treatment apparatus 100 according to the embodiment of the invention.

The linear movement type reaction treatment apparatus according to the embodiment is mainly different from the linear movement type reaction treatment apparatus 10 according to the first embodiment illustrated in FIG. 2 in that a light guiding trestle 321 (32), the measurement unit 40, and the container group 120 provided in the dispensing head 150 are different.

Figure 11:
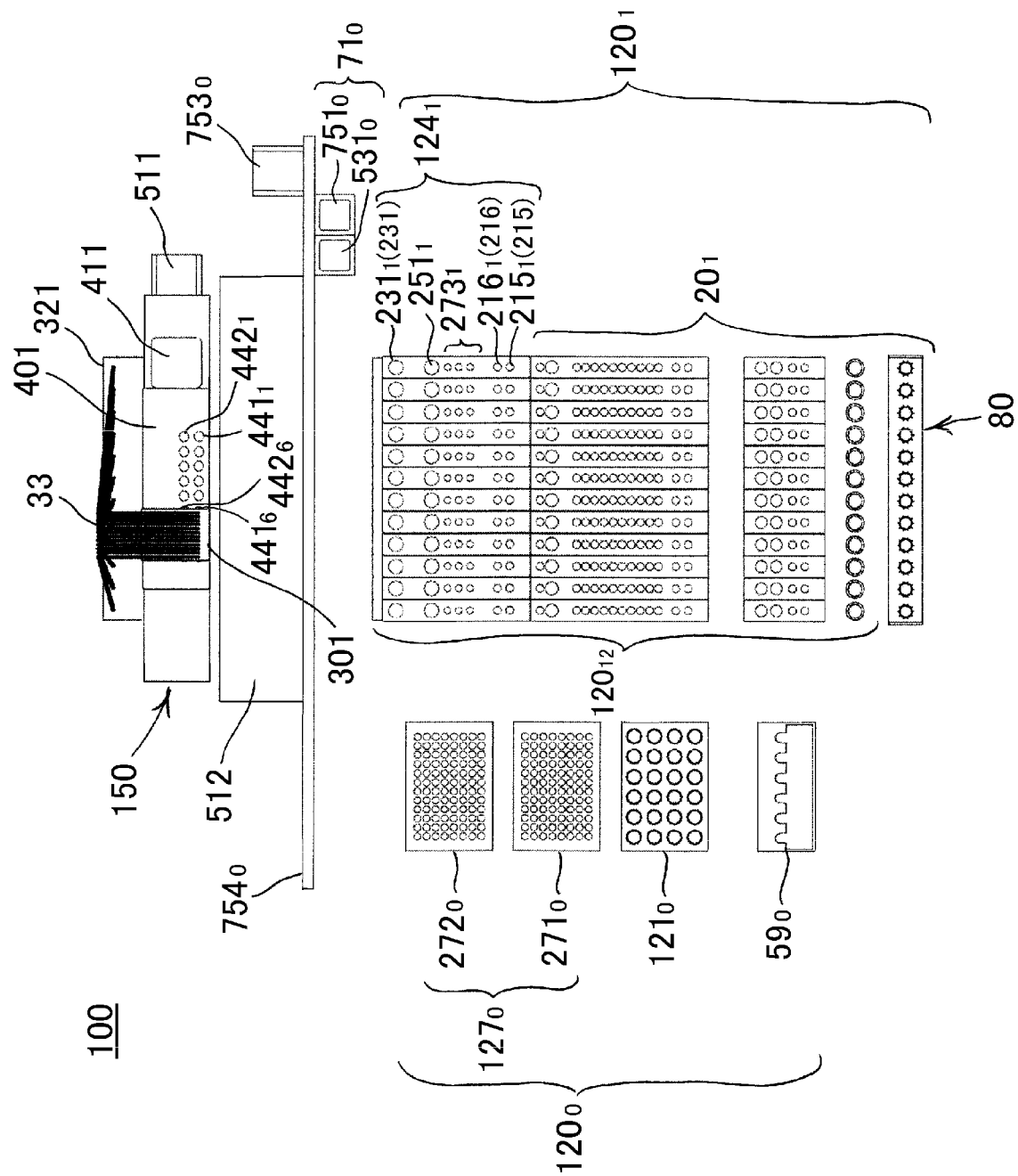
FIG. 11 is a top view illustrating the linear movement type reaction treatment apparatus illustrated in FIG. 9.

As illustrated in FIGS. 9 and 11, the common region $120_O$, the exclusive regions $120_i$, the ultrasonic vibration device 80, and the temperature controller 129 are provided on the stage other than the dispensing head 150.

The common region $120_O$ includes a reagent storage portion group $127_O$ that includes two micro plates $271_O$ and $272_O$ with a well $270_O$ of eight rows by twelve columns, a tip storage portion group $21_O$ that stores the dispensing tip $211_O$ of four rows by six columns attachable to the crossing nozzle $71_O$, and a dispensing tip attachment/detachment portion $59_O$ that includes a plate provided with a notched portion $591_O$ for detaching the main dispensing tip $211_O$ attached to the crossing nozzle $71_O$ from the nozzle $71_O$.

Each of twelve exclusive regions $120_i$ further includes a liquid storage portion $273_i$ that stores a reagent used to amplify nucleic acid, a storage portion 231 that stores a PCR tube $231_i$ as a reaction container, a storage portion $25_i$ that seals the PCR reaction container by the hermetic lid $251_i$, and a PCR amplification cartridge container $124_i$ that includes PCR dispensing tip storage portions 215 and 216 in addition to the storage portions of the exclusive region $20_i$ described in the first embodiment. Here, these components are provided in the linear arrangement direction along with the nucleic acid extraction cartridge container $24_i$ and the like.

These storage portions are arranged in parallel to the Y-axis direction, for example, at the pitch of 18 mm. The PCR tubes $231_i$ are detachably linked to twelve link portions $31_i$ provided in the light guiding trestle 321 to be described later through one hermetic lid $251_i$ which is more translucent. Further, the liquid storage portion $273_i$ stores a buffer solution necessary for a PCR reaction. The PCR tip storage portions 215 and 216 store a punching tip $216_i$ for punching a film coating the PCR tube $231_i$ and the liquid storage portion 273 and a dispensing tip $215_i$, and are provided with barcodes for displaying the sample information item and the inspection information item on the amplification cartridge container $124_i$.

Further, as illustrated in FIG. 9, the dispensing head 150 of the linear movement type reaction treatment apparatus 100 according to the second embodiment has the same configuration as the dispensing head 50 illustrated in FIG. 2 except for the existence of the optical fiber (bundle) 33.

However, in fact, as illustrated in FIG. 10, the dispensing head 150 independently includes the light guiding trestle 321, the array body X-axis movement mechanism 41, the trestle Z-axis movement mechanism 35, the measurement unit 40, the connection end array body 30, and the optical fiber (bundle) 33 in addition to the nozzle Z-axis movement mechanism 75, the crossing nozzle suction/ejection mechanism 53, and the magnetic portion 57 described in FIG. 2.

The light guiding trestle 32 includes twelve link portions 31, and the dispensing head 150 includes the optical fiber (bundle) 33 that serves as a flexible light guiding portion extending backward from the link portion 3, the connection end array body 30, the array body Y-axis movement mechanism 41, and the measurement unit 40 including the measurement end 44.

The light guiding trestle 321 is formed in a block shape extending in the X-axis direction. Here, twelve columnar link portions 31 which are directly or indirectly linkable to the opening portions of the PCR tubes $231_i$ and include the front ends of the optical fibers (bundle) 33 optically connected to the inside of the PCR tubes $231_i$ are provided so as to protrude downward from the trestle 321, and are arranged in the X-axis direction. Since the trestle 321 is supported by the base body 501 of the dispensing head 150 so as to be movable in the Z-axis direction by the trestle Z-axis movement mechanism 35, the trestle is movable in the Y-axis direction and the Z-axis direction. The trestle Z-axis movement mechanism 35 includes a Z-axis driving motor 351 and a trestle Z-axis movement support body 352.

The link portion 31 is provided with the front ends of the optical fibers (bundle) 33. Here, the connection end array body 30 is provided in which the connection end $34_i$ branched into two ends of the first connection end $341_i$ and the second connection end $342_i$ and having the rear end corresponding to each link portion $31_i$ while penetrating the light guiding trestle 321 is disposed in the arrangement surface at a gap narrower than the gap between the link portions $31_i$ in a path along two lines of the X-axis direction as a predetermined path, and an optical system incorporated body 401 and a circuit board 402 are provided as a measurement unit. The measurement unit is provided so as to be adjacent to or contact the arrangement surface, and includes the measurement end $44_j$ that is branched into two ends of the first measurement end $441_j$ and the second measurement end $442_j$ provided at six positions so as to be optically and serially connected along the two lines where the first connection end $341_i$ and the second connection end $342_i$ as the connection end $34_i$ are arranged. Further, the measurement unit may receive the light of fluorescence as the optical state inside the PCR tube $231_i$ and emit the excitation light by the optical connection of the first and second connection ends and the first and second measurement ends in this order.

Here, the first connection end $341_i$ is used to receive the fluorescence as the optical state inside the PCR tube $231_i$ from the link portion $31_i$, and is connectable to the first measurement end $441_j$ optically connected to the light receiving portion, and the second connection end $342_i$ is used to emit excitation light into the PCR tube $231_i$ through the link portion $31_i$ and is connectable to the second measurement end $442_j$ optically connected to the light emitting source irradiating the excitation light.

Further, the light guiding trestle 321 is provided with a cylindrical body that protrudes upward from the horizontal plate 32a just above the link portion $31_i$ and holds the optical fiber (bundle) $33_i$ extending backward from the link portion $31_i$ so as to cause the optical fiber to pass therethrough in order to prevent the bending thereof. Similarly, the connection end array body 30 is also provided with a cylindrical body which is provided near the connection end $34_i$ and causes the optical fiber (bundle) $33_i$ extending from the connection end $34_i$ to pass therethrough in order to prevent the bending thereof.

The measurement unit 40 corresponds to the measurement of fluorescence, and includes six kinds of specific wavelength measurement units $40_j$ which are arranged along the line of the X-axis direction as the predetermined path so as to respectively measure six kinds of fluorescence. For example, the measurement unit is fixed to the base body 501, the Y-axis movement frame 512, or the support member of the dispensing head 150. Accordingly, the measurement unit 40 does not move by the nozzle Z-axis movement mechanism 75, the trestle Z-axis movement mechanism 35, or the array body Z-axis movement mechanism 41.

In the optical system incorporated body 401, the measurement ends $44_j$ of the plurality of kinds of (in this example, six kinds of) specific wavelength measurement units $40_j$ (j=1, 2, 3, 4, 5, 6) are provided at the upper position. Inside the optical system incorporated body, the optical system portions of the specific wavelength measurement units $40_j$ are arranged in a linear shape, and are fixed to the base body 501 of the dispensing head. Here, the first measurement end $441_j$ and the second measurement end $442_j$ which are branched as two measurement ends $44_j$ of the specific wavelength measurement unit $40_j$ are arranged along a linear path of the X-axis direction as a predetermined path so as to be sequentially and optically connected to the first connection end $341_i$ and the second connection end $341_i$ as two connection ends $34_i$.

For example, when the pitch of the link portions $31_i$ is set to 18 mm, the pitch between the connection ends $34_i$ is 9 mm as a half of the pitch of the link portions. Then, the pitch between the measurement ends $44_j$ is, for example, 9 mm or less.

There is a case where the first measurement end $441_j$ and the second measurement end $442_j$ of the measurement end $40_j$ connected to the specific wavelength measurement units $40_j$ are laterally arranged along one line of the X-axis direction following the predetermined path or are arranged along two lines arranged in the length direction (the Y-axis direction).

In the former case, the emission of the excitation light is not stopped, and the measurement units sequentially receive the light at the light receiving timing set based on the speed of the connection end array body, the pitch between the connection ends, the distance between the first measurement end and the second measurement end of the measurement end, and the pitch between the measurement ends.

Meanwhile, in the latter case, as illustrated in FIG. 10, the first connection end $341_i$ is connected to only the first measurement end $441_j$, the second measurement end $442_j$ is connected to only the second connection end $342_i$, the predetermined path corresponds to two paths, and the optical fiber (bundle) $33_i$ includes a light receiving optical fiber (bundle) $331_i$ with a first connection end and an emission optical fiber (bundle) $332_i$ with a second connection end. In this case, since the light emitting source and the light receiving portion are connected to the link portion by an exclusive optical fiber compared to the former case, the control is easily performed. Further, since the optical fibers are used so as to be respectively suitable for the light emitting operation and the light receiving portion, the reliability is high.

The speed of the connection end array body 30 with respect to the measurement end $44_j$ is set in consideration of the stable light receiving time, the lifetime of fluorescence for the emission of the excited light, the number of connection ends, and the pitch between the connection ends (the distance of the predetermined path). For example, in the case of the measurement of the real-time PCR, the speed is controlled at 100 to 500 mm/s. In the embodiment, since the arrangement surface needs to slide on the measurement end $44_j$, it is possible to prevent unnecessary light from being incident to the measurement end $44_j$. Further, the connection end array body 30 moves continuously with respect to the measurement end or intermittently so as to be instantly stopped whenever the connection end array body moves between the connection ends or by one pitch between the measurement ends.

Figure 12:
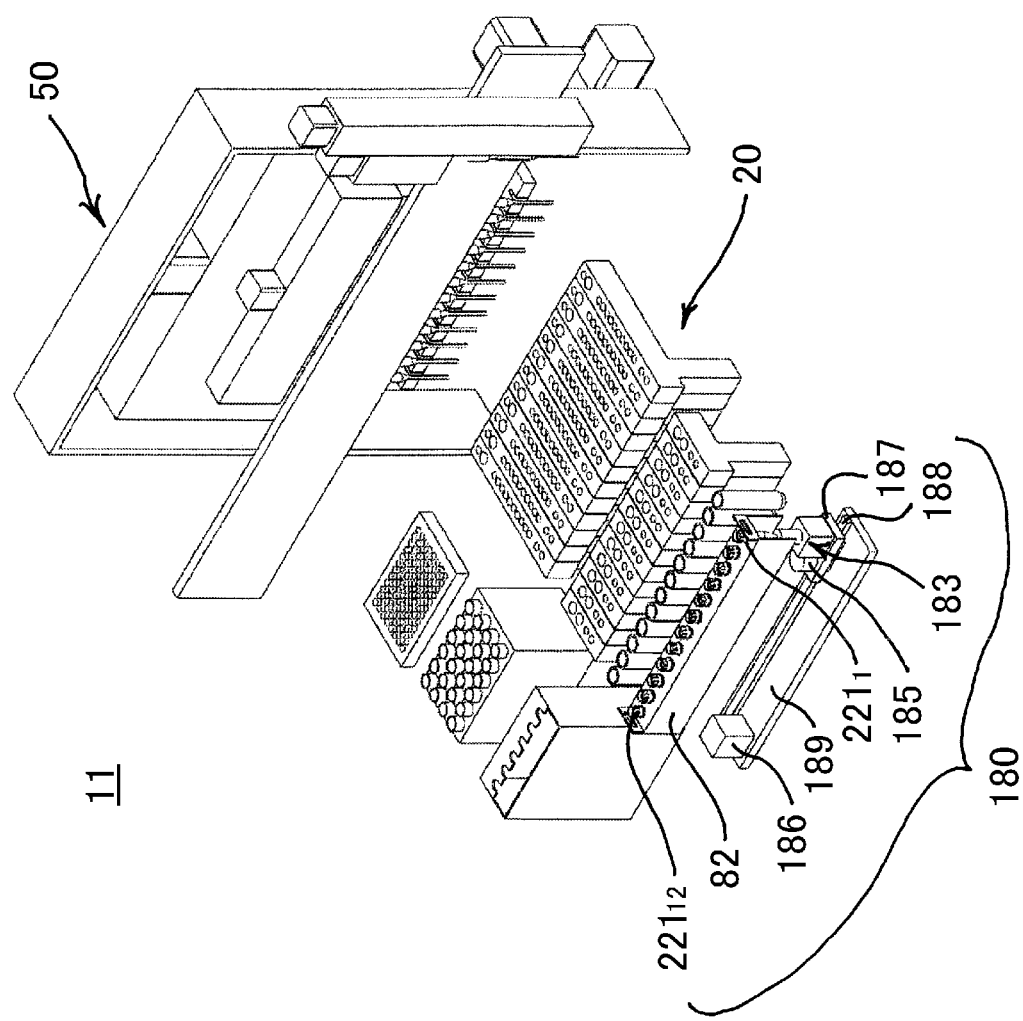
FIG. 12 is an enlarged cross-sectional view illustrating a measurement end of the linear movement type reaction treatment apparatus illustrated in FIG. 9.

FIG. 12 illustrates a state where a reaction container control system 90 is provided and the link portion $31_i$ (here, for example i=1) protruding downward from the light guiding trestle 321 in the opening portion of the reaction container group provided with the PCR tube $231_i$ as a plurality of (in this example, twelve) reaction containers as the reaction container control system 90 is indirectly linked to the PCR tube $231_i$ through the translucent hermetic lid $251_i$ attached to the opening portion of the PCR tube $231_i$ in the exclusive region $120_i$. Here, the link portion $31_i$ is linked to the PCR tube $231_i$ while being fitted into the link recess $253_i$ of the hermetic lid $251_i$.

As illustrated in FIG. 12, the link portion $31_1$ is indirectly linked to the PCR tube $231_i$ through the hermetic lid $251_i$, and includes a link cylinder $31a_i$ which substantially has a cylindrical shape and protrudes downward from the light guiding trestle 321. Here, a circular hole $31b_i$ having an opening of a size corresponding to a liquid surface of a liquid stored in the narrow opening tube is punched in the center portion of the bottom plate of the link cylinder $31a_i$, and an annular edge $31d_i$ which protruded downward is provided in the peripheral edge of the bottom plate. Accordingly, the close contact between the link portion and the hermetic lid is prevented. A spherical ball lens $381_i$ which has a diameter corresponding to the inner diameter of the link cylinder is loosely inserted into the link cylinder $31a_i$ and is placed on the circular hole $31b_i$. In an area of a predetermined distance above the ball lens $381_i$, an optical fiber $33_i$ which is coated by a resinous ferrule $31c_i$ and of which the front end reaches the outside while penetrating the light guiding trestle 321 is provided. The rear end of the optical fiber $33_i$ is formed by a light receiving optical fiber $331_i$ connected to the first connection end $341_i$ and an emission optical fiber $332_i$ connected to the second connection end $342_i$. The link cylinder $31a_i$, the circular hole $31b_i$, the ball lens $381_i$, and the bundle of the optical fiber $33_i$ are coaxially disposed inside the link cylinder $31a_i$.

As illustrated in FIG. 12, the reaction container control system 90 includes a PCR tube $231_i$ that serves as a reaction container which performs an amplification reaction or the like while storing a target solution of DNA having a target base sequence, a heater 37, and a PCR temperature controller $291_i$. The heater 37 is formed by stacking a heating block 37c as an aluminum plate having high thermal conductivity, a sheet heater 37a, and a heat insulating material 37b. Twelve penetration holes $37d_i$ which store and hold the plurality of (in this example, twelve) PCR tubes $231_i$ are punched in the same heater 37, and the wide opening tube $235_i$ is supported by the heating block 37c.

The PCR temperature controller 291 includes a temperature control block $292_i$, a peltier device $293_i$, and a heat sink $294_i$ which are stored in the narrow opening tube $233_i$ of the PCR tube $231_i$ as the reaction container.

The narrow opening tube $233_i$ of the PCR tube $231_i$ includes a lower wall portion $233a_i$ of a portion contacting the temperature control block $292_i$, and also includes an upper wall portion $235a_i$ corresponding to the wall portion of the wide opening tube $235_i$ contacting the heating block 137c of the heater while being provided above the lower wall portion $233a_i$ with a gap therebetween.

According to the embodiment, the hermetic lid control unit 67 (the CPU+program 160) first instructs the dispensing head movement mechanism 51 so that the link portion $31_i$ of the light guiding trestle 321 moves to the hermetic lid storage portion $25_i$ and instructs the trestle Z-axis movement mechanism 35 so that the hermetic lid $251_i$ is attached to the link portion $31_i$ by fitting. Next, the link portion $31_i$ is linked to the PCR tube $231_i$ at the same time when the opening portion of the predetermined PCR tube $231_i$ is fitted by the hermetic lid $251_i$.

Next, in the case of PCR, the heater 137 is controlled so that the upper wall portion $235a_i$ is heated at a uniform temperature (for example, 100° C.) higher than the predetermined maximum temperature (for example, 94° C.) by some degrees, that is, 5° C. in response to the temperature control of the temperature controller 129 in accordance with the instruction of the measurement control unit 62. Accordingly, the hermetic lid $251_i$ fitted to the wide opening tube $235_i$ of the PCR tube $231_i$ is heated, so that the condensation of the hermetic lid may be prevented. At that time, the upper wall portion $235a_i$ is separated from the lower wall portion $233a_i$ subjected to the temperature control by a predetermined gap, and is heated while a heating source contacts or is adjacent to the upper wall portion $235a_i$ having a surface area smaller than the lower wall portion. Accordingly, the lower surface of the hermetic lid $251_i$ provided at a position close to the upper wall portion $235a_i$ is heated due to the heating of the upper wall portion $235a_i$, and hence the condensation thereof may be prevented.

Meanwhile, since the link portion $31_i$ merely contacts the upper portion of the hermetic lid $251_i$ through the annular edge $31d_i$, there is no influence of the heating performed at a position facing the hermetic lid $251_i$. Similarly, the lower wall portion $233a_i$ is controlled at a predetermined temperature by a peltier device having a heating/cooling function, and is measured at the same time. After the measurement ends, the hermetic lid is moved close to the link portion $31_i$ by the detachment member 391 in accordance with the instruction of the hermetic lid control unit 67, and the light guiding trestle 321 is moved upward by the trestle Z-axis movement mechanism 35. Accordingly, the hermetic lid $251_i$ is detached from the link portion, and the linking state is released by moving the link portion left in the PCR tube $231_i$.

Subsequently, the operation of the linear movement type reaction treatment apparatus 100 according to the second embodiment will be described below.

Since step S1 for the process of separating and extracting nucleic acid as a target material from the sample to step S11 are substantially the same as the operation of the linear movement type reaction treatment apparatus 10 according to the first embodiment except that control is performed by the extraction control unit 65 of the nucleic acid treatment control unit 63 of the CPU+program 160 of the linear movement type reaction treatment apparatus 100, the description thereof will not be repeated. Then, a description will be made from step S12 for the process of amplifying and measuring the nucleic acid to step S16.

In step S12, a new dispensing tip $211_i$ is attached to the nozzle $71_i$. Then, a solution containing nucleic acid stored in the eighth liquid storage portion is suctioned, is ejected while being transferred to the PCR tube $231_i$ storing the amplification solution $234_i$ in advance, and is introduced into the container. The dispensing head 50 is moved by the dispensing head movement mechanism 51 so that the nozzle $71_i$ thereof is moved to a position above the hermetic lid storage portion $25_i$ storing the hermetic lid $251_i$ of the container group 120. The hermetic lid is moved downward by the nozzle Z-axis movement mechanism 75 so that the link recess $253_i$ above the hermetic lid 251 is attached to the lower end of the nozzle $71_i$ by fitting.

Then, the hermetic lid is moved upward by the nozzle Z-axis movement mechanism 75 so that the hermetic lid 251 is located above the PCR tube 231$_i$ by the dispensing head movement mechanism 51. Subsequently, the hermetic lid 251$_i$ is moved downward by the nozzle Z-axis movement mechanism 75 so that the hermetic lid is fitted to the opening portion of the wide opening tube 235$_i$ of the PCR tube 231$_i$ in order to seal the inner space.

In step S13, the measurement control unit 62 instructs the dispensing head movement mechanism 51 so that the dispensing head 50 is moved in the Y axis and the link portion 31$_i$ of the light guiding trestle 321 is located above the PCR tube 231$_i$ equipped with the hermetic lid 251$_i$. Then, the light guiding trestle 32 is moved downward by the trestle Z-axis movement mechanism 35 so that the link portion 31$_i$ is inserted into the recess of the hermetic lid 251$_i$ and the lower end thereof contacts or closely contacts the bottom surface of the recess.

In step S14, the nucleic acid treatment control unit 63 instructs that the temperature controller 129 repeats a cycle of temperature control using a real-time PCR, for example, a cycle of heating the PCR tube 231$_i$ at 96° C. for 5 seconds and heating the PCR tube at 60° C. for 15 seconds, for example, 49 times.

In step S15, the measurement control unit 62 determines whether to start an elongation process in each cycle when the temperature control is started by the nucleic acid treatment control unit 63 in each cycle, and causes the connection end array body 30 to move continuously or intermittently with respect to each measurement end 44$_j$ of the measurement unit 40. The movement speed is set to a speed which is calculated based on the stable light receiving time, the fluorescence lifetime, and the number (in this example, twelve) of the exclusive regions 120$_i$. Accordingly, the light is completely received from twelve PCR tubes 231$_i$ within the stable light receiving time.

In step S16, the measurement control unit 62 instructs the light receiving operation in the measurement unit 40 by determining the moment of the optical connection of, for example, the optical fiber (bundle) 33$_i$ of the link portion 31$_i$ with respect to the first measurement end and the second measurement end of the measurement end 44$_j$.

The measurement is performed in an exponential amplification cycle, and an amplification curve may be obtained based on the measurement. Then, various kinds of analyses are performed based on the amplification curve. Furthermore, the measurement control unit 62 heats the heater 37 incorporated in the light guiding trestle 321 in order to prevent the condensation of the hermetic lid 251. Accordingly, the measurement may be performed clearly.

Further, in the linear movement type reaction treatment apparatus 100 according to the embodiment, a target material is extracted by crushing a shell of bacteria as a sample in a sample suspension through an ultrasonic vibration and is mixed with a separation/extraction solution so as to solubilize protein. Accordingly, it is possible to reliably and efficiently separate and extract nucleic acid as a target material. Thus, the amplification of nucleic acid is drastically improved, and the optical measurement is performed with high precision.

Furthermore, as one embodiment, a heater as a heating unit may be provided at the base of each link portion 31$_i$ of the light guiding trestle 32 so as to heat the hermetic lid 251$_i$ at, for example, 105° C. instead of the heating unit provided in the PCR tube 231$_i$.

Figure 13:
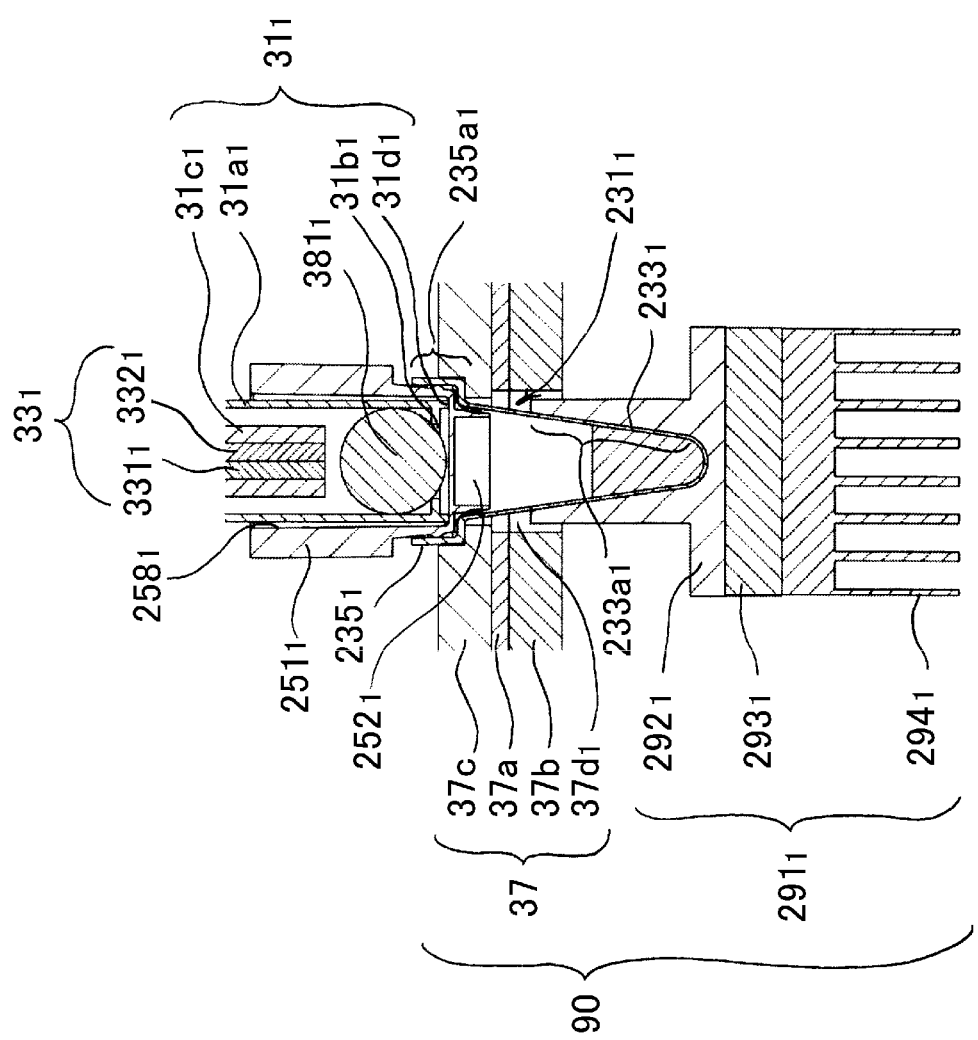
FIG. 13 is an entire perspective view illustrating a linear movement type reaction treatment apparatus according to a third embodiment of the invention.

FIG. 13 illustrates a linear movement type reaction treatment apparatus 11 according to a third embodiment. Here, an ultrasonic vibration device 180 according to another embodiment is assembled to the linear movement type reaction treatment apparatus 10 according to the first embodiment illustrated in FIG. 2 instead of the ultrasonic vibration device 80.

The ultrasonic vibration device 180 includes an ultrasonic vibration unit 183 that includes an ultrasonic vibrator and a horn resonated by the vibration and elastically biased, a vibration unit movement mechanism (186, 187, 188, 189) that moves the ultrasonic vibration unit 183 with respect to the sample storage portions 221$_1$ to 221$_{12}$, and a forward/backward movement motor 185 (corresponding to the forward/backward movement mechanism) that moves the horn and the ultrasonic vibrator in the up and down direction in a telescopic manner and moves the horn from the ultrasonic vibration unit close to the sample storage portions 221$_1$ to 221$_{12}$ so as to be pressed against the sample storage portions 221$_1$ to 221$_{12}$.

The vibration unit movement mechanism (186, 187, 188, 189) includes a guide metal bar 188 that is disposed in the X axis on a plate 189, a carrier 187 that is equipped with a slider having a sliding surface guided by the guide metal bar 188, and a motor 186 that is provided in the plate 189 that drives a timing belt (not illustrated) suspended on rotors provided on a side surface of a rectangular columnar casing of the ultrasonic vibration unit 183. The carrier 187 is provided with the forward/backward movement motor 185 and the ultrasonic vibration unit 183.

Figure 14:
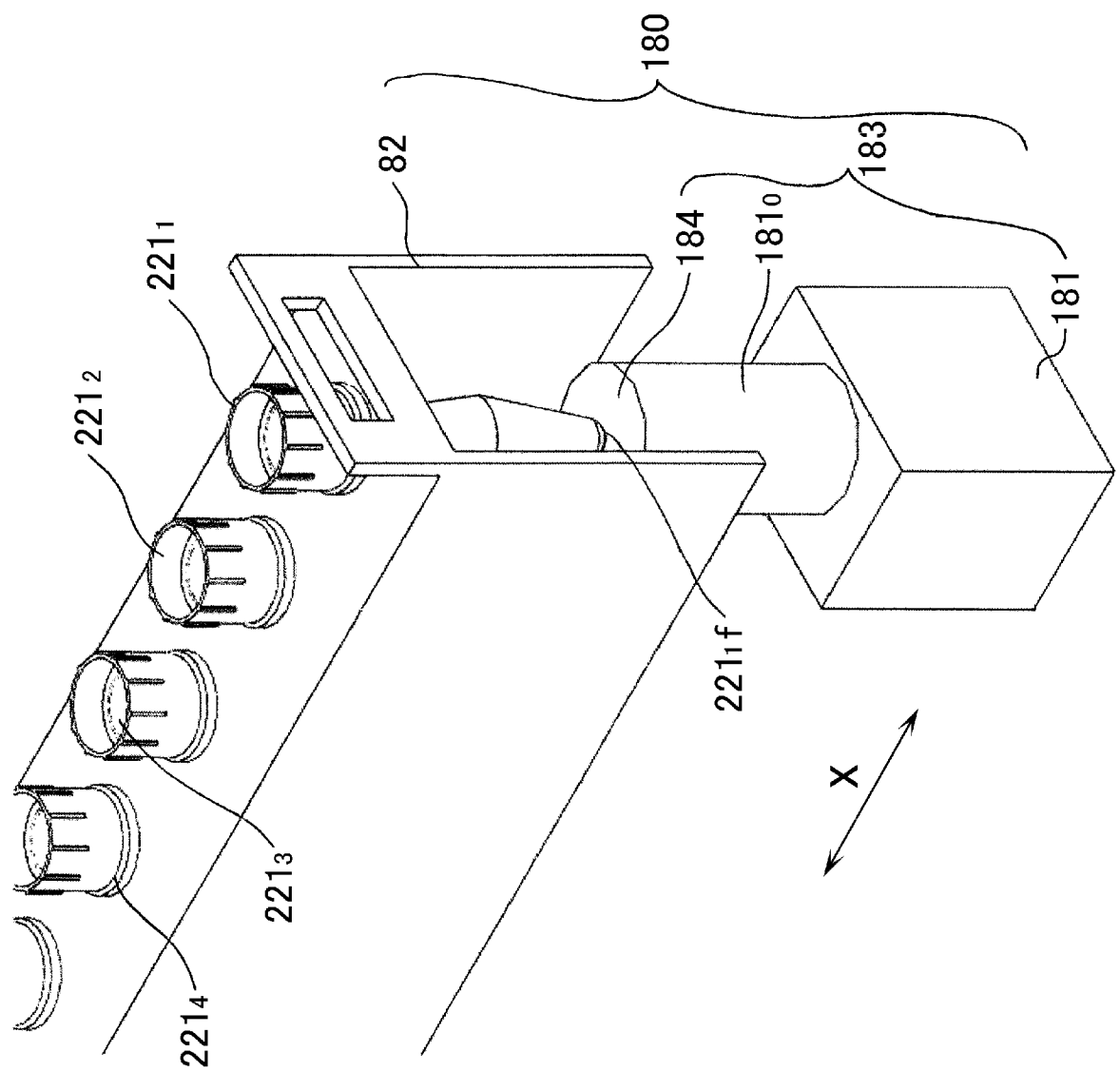
FIG. 14 is an enlarged perspective view illustrating a part of an ultrasonic vibration device illustrated in FIG. 13.

As specifically illustrated in FIG. 14, the ultrasonic vibration unit 183 is located at a lower position in the vicinity of the bottom portion 221$_1$f of the sample storage portion 221$_1$ as the vibration target by the movement in the X-axis direction of the carrier 187 of the vibration unit movement mechanism (186, 187, 188, 189) while a horn 181$_0$ is moved backward and downward by the forward/backward movement motor 185. The horn 181$_0$ (and the ultrasonic vibrator) is moved forward and upward by the forward/backward movement motor 185 provided in the carrier 187 so that the front end 184 of the horn 181$_0$ is pressed against the center bottom portion 221$_1$f. The center portion of the front end 184 is depressed, and is held while being guided to the bottom portion 221$_1$f of the sample storage portion 221$_1$. Since the sample storage portion 221$_1$ is fixed to the sample storage portion support base 82 in the up and down direction, the sample storage portion 221$_1$ does not protrude. Furthermore, the sample storage portion is provided with a certain allowance in the horizontal direction.

According to the embodiment, since the ultrasonic vibration unit 183 is provided so as to be movable between the sample storage portions 211$_i$, there is no need to provide the ultrasonic vibrator and the horn in each sample storage portion 211$_i$. Since the ultrasonic vibration is applied while the sample storage portion is pressed against the horn by using one ultrasonic vibration unit 183, it is possible to simplify the structure of the apparatus and decrease the manufacturing cost without degrading the quality even when a plurality of sample storage portions is used.

Figure 15:
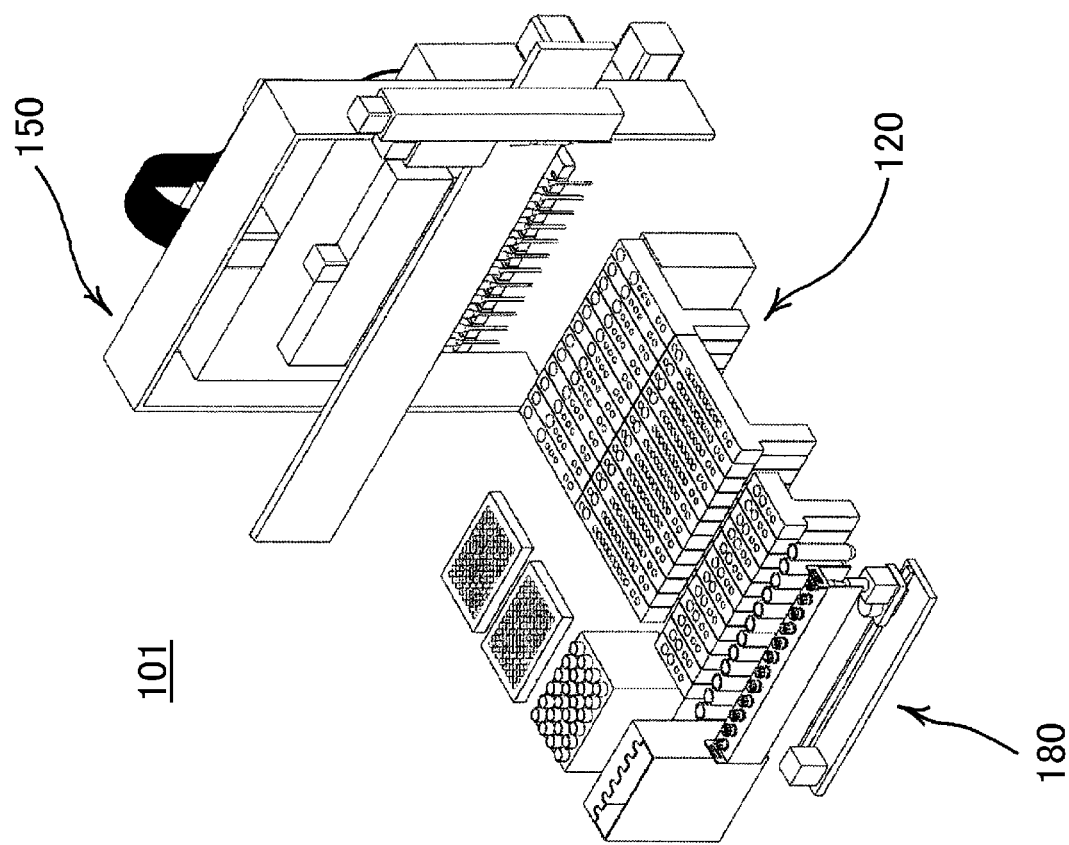
FIG. 15 is an entire perspective view illustrating a linear movement type reaction treatment apparatus according to a fourth embodiment of the invention.

FIG. 15 illustrates a linear movement type reaction treatment apparatus 101 according to a fourth embodiment. Here, an ultrasonic vibration device 180 according to another embodiment is assembled to the linear movement type reaction treatment apparatus 100 according to the first embodiment illustrated in FIG. 9 instead of the ultrasonic vibration device 80.

Since the same reference signs will be given to the same components, the description thereof will not be repeated.

The above-described embodiments have been specifically described in order to help the comprehension of the invention, and do not limit the other embodiments. Accordingly, a modification may be made without departing from the spirit of the invention. For example, the configuration, the shape, the material, the arrangement, the amount, and the number of the nozzle, the dispensing tip, the punching tip, the container group, the exclusive region, the common region, the storage portion, the measurement end, the measurement unit, the specific wavelength measurement unit, the suction/ejection mechanism, the movement mechanism, the tip attachment/detachment mechanism, the magnetic portion, the heating unit, the reaction container, the hermetic lid, the scattering prevention lid, the ultrasonic vibration device, the light guiding trestle, the link portion, the light guiding portion, the connection end, the connection end array body, the link portion array body, the dispensing head, the temperature controller, the hermetic lid attachment/detachment mechanism, the ultrasonic vibration unit, and the like and the reagent and the sample used therein are not limited to the embodiments. Further, the dispensing head is moved with respect to the container group, but the container group may be moved with respect to the dispensing head.

Further, in the description above, the amplification solution is sealed by the hermetic lid in order to seal the PCR reaction container. However, the PCR reaction container may be sealed by using a sealing solution such as mineral oil instead of or together with the hermetic lid. Further, a punching pin which is driven by the suction/ejection mechanism may be used instead of performing the punching operation by attaching the punching tip to the nozzle. Further, in the description above, the real-time PCR measurement has been described, but the invention may be also applied to various kinds of measurement having temperature control instead of this measurement. Further, in the description above, a case has been described in which the measurement unit is provided in the dispensing device, but the invention is not limited thereto. The optical system using the optical fiber provided inside the measurement unit has been described, but an optical system using a lens system may be employed.

Further, the apparatuses described in the embodiments of the invention and the components constituting these apparatuses or the parts constituting the components may be appropriately selected, modified, and combined. Furthermore, the spatial marks for the "upside", the "downside", the "inside", the "outside", the "X axis", the "Y axis", and the "Z axis" in the specification are used to help the comprehension of the drawings. That is, the invention does not limit the specific spatial direction or arrangement of the structure.

INDUSTRIAL APPLICABILITY

The invention relates to, for example, a field for the treatment, the inspection, and the analysis of nucleic acid mainly containing DNA, RNA, mRNA, rRNA, and tRNA. Further, the invention relates to, for example, an industrial field, an agricultural field such as food processing, agricultural processing, and seafood processing, a chemicals field, a pharmaceutical field, a medical field such as sanitation, insurance, disease, and inheritance, and a science field such as biochemistry or biology. Particularly, the invention may be used to treat or analyze various kinds of nucleic acid such as PCR and real-time PCR.

REFERENCE SIGNS LIST 10, 11, 100, 101: linear movement type reaction treatment apparatus
20, 120: container group
$20_i$, $120_i$ (i=1, . . . , 12): exclusive region
$20_0$, $120_0$: common region
$211_i$, $212_i$ (i=1, . . . , 12): dispensing tip
$231_i$ (i=1, . . . , 12): PCR tube (reaction container)
29, 129: temperature controller
30: connection end array body
$31_i$ (i=1, . . . , 12): link portion
32 (321): light guiding trestle
$33_i$: optical fiber (light guiding portion)
40 (401, 402): measurement unit
$40_j$ (j=1, . . . , 6): specific wavelength measurement unit
$44_j$: measurement end
50, 150: dispensing head
53: suction/ejection mechanism
59: tip attachment/detachment mechanism
60, 160: CPU program
61, 65: extraction control unit
70: nozzle arrangement portion
$71_i$ (i=1, . . . , 12): nozzle
$71_0$: crossing nozzle
80, 180: ultrasonic vibration device
82: sample storage portion support base
183: ultrasonic vibration unit
185: forward/backward movement motor

The invention claimed is:

1. A linear movement type reaction treatment apparatus comprising:

a container group including first and second reaction containers and first, second, third, and fourth liquid storage portions having opening portions, the first reaction container and the first and second liquid storage portions being arranged in a first linear shape, and the second reaction container and the third and fourth liquid storage portions being arranged in a second linear shape, one of the first and second liquid storage portions arranged in the first linear shape receiving a first solution, and one of the third and fourth liquid storage portions arranged in the second linear shape receiving a second solution;

a dispensing head to which first and second dispensing tips are detachably attachable, the first dispensing tip including a first front end insertable into the first reaction container and the first and second liquid storage portions arranged in the first linear shape to suction and eject liquids, and the second dispensing tip including a second front end insertable into the second reaction container and the third and fourth liquid storage portions arranged in the second linear shape to suction and eject liquids, wherein the dispensing head is relatively movable in a linear arrangement direction along the container group, wherein the first and second dispensing tips correspond to the first and second linear shapes, respectively, so that the first and second dispensing tips are capable of entering respective ones of the first and second linear shapes while not entering others of the first and second linear shapes;

a magnetic portion provided in the dispensing head and capable of separating magnetic particles contained in first and second solutions inside each of the first and second dispensing tips, respectively, by applying a magnetic field to each of the first and second dispensing tips so that the magnetic particles are adsorbed to respective inner walls of the first and second dispensing tips, and separating the adsorbed magnetic particles by removing the magnetic field therefrom so that the magnetic particles are resuspended in the first and second solutions;

an ultrasonic vibration device capable of applying ultrasonic vibration to one of the first and second liquid storage portions receiving the first solution and to one of the third and fourth liquid storage portion receiving the second solution, the ultrasonic vibration device comprising an ultrasonic vibration unit that includes an ultrasonic vibrator, a horn adapted to be resonated by the ultrasonic vibration, a forward/backward movement mechanism adapted to move the horn so as to press one of the first and second liquid storage portions receiving the first solution and one of the third and fourth liquid storage portion receiving the second solution, and a vibration unit movement mechanism adapted to move the ultrasonic vibration unit in a direction perpendicular to the linear arrangement direction so as to cross the first and second linear shapes; and a control unit configured to control at least the dispensing head and the ultrasonic vibration device, wherein the first solution comprises a first suspension of magnetic particles stored in the first linear shape, and the second solution comprises a second suspension of magnetic particles stored in the second linear shape;

wherein, in the first linear shape, a first scattering prevention lid is attachable to the opening portion of one of the first and second liquid storage portions receiving the first solution and, in the second linear shape, a second scattering prevention lid is attachable to the opening portion of one of the third and fourth liquid storage portions receiving the second solution; wherein an upper portion of each of the first and second scattering prevention lids is formed so as to be detachably attachable to the dispensing head, wherein the opening portions are adapted to be closed with the respective first and second scattering prevention lids by using the dispensing head, the first and second scattering prevention lids being attachable to the opening portions and detachable from the dispensing head to close the opening portions;

wherein the first and second scattering prevention lids are equipped with films that are punchable by downward movement of one or more punching tips, the one or more punching tips being detachably attachable to the dispensing head;

wherein the control unit controls the dispensing head and the ultrasonic vibration device so that, after the opening portions are closed with the first and second scattering prevention lids and the first and second scattering prevention lids are detached from the dispensing head, the ultrasonic vibration device sequentially applies the ultrasonic vibration to one of the first and second liquid storage portions receiving the first solution and to one of the third and fourth liquid storage portions receiving the second solution using the ultrasonic vibration unit; and wherein the control unit controls the dispensing head and the ultrasonic vibration device so that, after the ultrasonic vibration is applied to one of the first and second liquid storage portions receiving the first solution and to one of the third and fourth liquid storage portions receiving the second solution, the films of the respective first and second scattering prevention lids are punched by the one or more punching tips attached to the dispensing head so that the first suspension of magnetic particles and the second suspension of magnetic particles may be removed from the first solution and the second solution.

2. The linear movement type reaction treatment apparatus according to claim 1,
wherein the dispensing head is equipped with a crossing head to which one or more other dispensing tips are detachably attachable, the crossing head being relatively movable with respect to the first and second linear shapes so as to cross the first and second linear shapes, and the one or more other dispensing tips each including a front end insertable into the first reaction container and the first and second liquid storage portions arranged in the first linear shape to suction and eject a liquid, or insertable into the second reaction container and the third and fourth liquid storage portion arranged in the second linear shape to suction and eject a liquid, and wherein the container group includes a common region which is provided outside the first and second linear shapes so that the one or more other dispensing tips attached to the crossing head are insertable therein, the common region including at least one solution storage portion into which each front end of the one or more other dispensing tips is insertable.

3. The linear movement type reaction treatment apparatus according to claim 2,
wherein a sample information item used to identify or manage a sample and an inspection information item used to represent an inspection content are visually displayed in each of the first and second linear shapes, and wherein the crossing head is equipped with a digital camera which obtains an image data by capturing a content displayed in each of the first and second linear shapes including the sample information item and the inspection information item.

4. The linear movement type reaction treatment apparatus according to claim 1,
wherein the apparatus includes the one or more punching tips that punch the films, the one or more punching tips storable in one or more tip storage portions and the one or more punching tips are attachable to the dispensing head.

5. The linear movement type reaction treatment apparatus according to claim 1, wherein the ultrasonic vibration device includes a support base that supports the first, second, third and fourth liquid storage portions in a vibratile manner.

6. The linear movement type reaction treatment apparatus according to claim 1, wherein the dispensing head includes:
a light guiding trestle that includes first and second link portions which are directly or indirectly respectively linked to the first and second reaction containers and are each equipped with a flexible light guiding portions optically connected to the inside of the respectively linked first and second reaction containers, a connection end array body that includes an arrangement surface which supports and arranges, along a predetermined path, first and second connection ends each equipped with a rear end of the respective flexible light guiding portions along a predetermined path, wherein a front end of the respective flexible light guiding portions are provided to each of the first and second link portions, a measurement unit that includes a first measurement end and a second measurement end that are provided so as to be adjacent to or contact the arrangement surface, the first measurement end being optically connectable to the first connection end and the second measurement end being optically connectable to the second connection end along the predetermined path, and the measurement unit being able to receive light based on optical states inside the first and second reaction containers via the sequential optical connection of the first and second connection ends with the first measurement end and the second measurement end, and
- a light guiding-converting mechanism that relatively moves the connection end array body with respect to the measurement unit so as to sequentially, respectively and optically connect the first and second connection ends arranged in the connection end array body to at least the first measurement end and the second measurement end.

7. The linear movement type reaction treatment apparatus according to claim 6, wherein the measurement unit is provided so that the inside of the measurement unit excluding the first and second measurement ends is not movable with respect to at least the first and second reaction containers and the light guiding trestle including the first and second link portions connected thereto when light is received by the measurement unit.

8. The linear movement type reaction treatment apparatus according to claim 6, further comprising:
- a trestle movement mechanism that moves the light guiding trestle with respect to the container group so that the first and second link portions are simultaneously directly or indirectly linked to the first and second reaction containers.

9. The linear movement type reaction treatment apparatus according to claim 6, further comprising:
- a measurement end array portion that arranges the first measurement end and the second measurement end so that the first measurement end and the second measurement end are sequentially and optically connectable to the first and second connection ends along the predetermined path; and
- wherein the measurement unit includes a plurality of specific wavelength measurement units receiving light of a specific wavelength or a specific wavelength band.

10. The linear movement type reaction treatment apparatus according to claim 6,
- wherein a translucent hermetic lid is attached to the opening portion of at least one of the first and second reaction containers and seals the at least one of the first and second reaction containers,
- wherein an upper portion of the hermetic lid is formed so as to be detachably attachable to the dispensing head, and
- wherein the hermetic lid is attachable to the opening portion of the at least one of the first and second reaction containers by the detachment of the hermetic lid from the dispensing head.

11. The linear movement type reaction treatment apparatus according to claim 10, further comprising
a heating unit capable of heating the hermetic lid.

12. The linear movement type reaction treatment apparatus according to claim 6, further comprising:
- a temperature controller that includes a temperature source provided so as to contact or be adjacent to a lower wall portion of at least one of the first and second reaction containers, the temperature source being operable to increase or decrease a temperature inside the at least one of the first and second reaction containers; and
- a heating unit that is provided so as to contact or be adjacent to an upper wall portion of the at least one of the first and second reaction containers located above the lower wall portion of the at least one of the first and second reaction containers, the heating unit including a heating source operable to heat the upper wall portion.

13. A linear movement type reaction treatment method comprising:
arranging first and second reaction containers and first, second, third, and fourth liquid storage portions together as a container group, the first reaction container and the first and second liquid storage portions being arranged in a first linear shape, and the second reaction container and the third and fourth liquid storage portions being arranged in a second linear shape, one of the first and second liquid storage portions arranged in the first linear shape receiving a first sample suspension, and one of the third and fourth liquid storage portions arranged in the second linear shape receiving a second sample suspension;
detachably attaching first and second dispensing tips to a dispensing head;
moving the dispensing head in a linear arrangement direction with respect to the container group;
storing the first sample suspension in one of the first or second liquid storage portions using the first or second dispensing tips, and storing the second sample suspension in one of the third or fourth liquid storage portions;
applying ultrasonic vibration to one of the first and second liquid storage portions in which the first sample suspension is stored and
applying ultrasonic vibration to one of the third and fourth liquid storage portions in which the second sample suspension is stored;
transferring the first sample suspension in the linear arrangement direction to another one of the first and second liquid storage portions or the first reaction container arranged in the first linear shape using the first dispensing tip; and
transferring the second sample suspension in the linear arrangement direction to another one of the third and fourth liquid storage portions or the second reaction container arranged in the second linear shape using the second dispensing tip;
wherein the first linear shape corresponds to the first dispensing tip so that the first dispensing tip enters the first linear shape and does not enter the second linear shapes;
wherein the second linear shape corresponds to the second dispensing tip so that the second dispensing tip enters the second linear shape and does not enter the first linear shape;
wherein the first reaction container, the first and second liquid storage portions, and a first tip storage portion in which the first dispensing tip is storable in an attachable manner are arranged in the first linear shape;
wherein the second reaction container, the third and fourth liquid storage portions, and a second tip storage portion in which the second dispensing tip is storable in an attachable manner are arranged in the second linear shape;
wherein the step of moving the dispensing head comprises a step of relatively moving the dispensing head with respect to the container group in the linear arrangement direction and inside each of the first and second linear shapes simultaneously;

wherein the step of applying ultrasonic vibration comprises:
transferring first and second scattering prevention lids in the linear arrangement direction while the first and second scattering prevention lids are attached to the dispensing head;
attaching the first scattering prevention lid to a first opening portion of one of the first and second liquid storage portions storing the first sample suspension and attaching the second scattering prevention lid to a second opening portion of one of the third and fourth liquid storage portions storing the second sample suspension so as to close the first and second opening portions by detaching the first and second scattering prevention lids from the dispensing head;
sequentially applying ultrasonic vibration to the first and second sample suspensions with an ultrasonic vibration unit that includes an ultrasonic vibrator and a horn resonated by the vibration of the ultrasonic vibrator after detaching the first and second scattering prevention lids from the dispensing head; and
punching films of the first and second scattering prevention lids by downward movement of one or more punching tips that are detachably attached to the dispensing head after the ultrasonic vibration is sequentially applied to the respective first and second sample suspensions with the ultrasonic vibration unit so that the first and second sample suspensions can be taken out by the first and second dispensing tips attached to the dispensing head; and
wherein the step of sequentially applying ultrasonic vibration comprises moving the ultrasonic vibration unit in a direction perpendicular to the linear arrangement direction so as to cross the first and second linear shapes, and moving the horn of the ultrasonic vibration unit so as to press the first or second liquid storage portion receiving the first sample suspension in the first linear shape and
moving the horn of the ultrasonic vibration unit so as to press the third or fourth liquid storage portion receiving the second sample suspension in the second linear shape.

14. The linear movement type reaction treatment method according to claim 13, further comprising:
providing a common region including at least one other liquid storage portion in the container group outside the first and second linear shapes;
causing a crossing head to enter the first and second linear shapes and the common region, the crossing head being provided in the dispensing head and movable with respect to the at least one other liquid storage portion of the common region and the first and second reaction containers, or the first, second, third, and fourth liquid storage portions in the first and second linear shapes; and
inserting a front end of one or more other dispensing tips into the first and/or second reaction containers, the first, second, third, and/or fourth liquid storage portions in the first and second linear shapes, or the at least one other liquid storage portion of the common region using the crossing head so as to suction or eject a solution through the front end.

15. The linear movement type reaction treatment method according to claim 13, further comprising:
extracting target materials from the first and second sample suspensions to which the ultrasonic vibration is applied;
moving the target materials in the linear arrangement direction and storing the target materials in the first and second reaction containers provided in the container group;
moving a light guiding trestle relative to the first and second reaction containers, the light guiding trestle including first and second link portions each equipped with a flexible light guiding portions;
simultaneously directly or indirectly, and respectively linking the first and second reaction containers to the first and second link portions so as to optically connect the inside of the respectively linked first and second reaction containers to the light guiding portions;
performing temperature control inside the first and second reaction containers; and
guiding light from the first and second reaction containers to a connection end array body including an arrangement surface supporting and arranging first and second connection ends along a predetermined path, the first and second connection ends each being equipped with a rear ends of the respective light guiding portion, wherein a front end of the respective light guiding portion is provided to each of the first and second link portions;
and sequentially, respectively and optically connecting the first connection end to a first measurement end provided in a measurement unit so as to be adjacent to or contact the arrangement surface and the second connection end to a second measurement end provided in a measurement unit so as to be adjacent to or contact the arrangement surface along the predetermined path via relative movement between the connection end array body and the first and second measurement ends, so that light based on optical states inside the first and second reaction containers is received by the measurement unit.

16. The linear movement type reaction treatment method according to claim 15,
wherein the first measurement end and the second measurement end, are arranged by a measurement end array portion so that the first measurement end and the second measurement end are sequentially and optically connectable to the first and second connection ends along the predetermined path, and
wherein the measurement unit includes a plurality of specific wavelength measurement units, each of the specific wavelength measurement units receiving light of a specific wavelength or a specific wavelength band based on the optical states inside the first and second reaction containers.

17. A linear movement type reaction treatment method comprising:
detachably attaching first and second dispensing tips to a dispensing head;
moving the dispensing head in a linear arrangement direction with respect to a container group including first and second reaction containers and first and second liquid storage portions, the first reaction container and the first liquid storage portion being arranged in a first linear shape corresponding to the first dispensing tip so that the first dispensing tip is capable of entering the first linear shape while not entering a second linear shape, and the second reaction container and the second liquid storage portion being arranged in the second linear shape corresponding to the second dispensing tip so that the second dispensing tip is capable of entering the second linear shape while not entering the first linear shape, the first liquid storage portion arranged in the first linear shape receiving a first sample suspension, and the second liquid storage portion arranged in the second linear shape receiving a second sample suspension;

applying ultrasonic vibration to the first and second sample suspensions;

separating a first target material from the first sample suspension using a first magnetic particle suspension having magnetic particles suspended to capture the first target material;

separating a second target material from the second sample suspension using a second magnetic particle suspension having magnetic particles suspended to capture the second target material;

introducing the separated first target material and a first reaction solution used for a reaction into the first reaction container located in the first linear shape and introducing the separated second target material and a second reaction solution used for a reaction into the second reaction container located in the second linear shape;

moving a light guiding trestle provided in the dispensing head with respect to the first and second reaction containers and along with the dispensing head, the light guiding trestle including first and second link portions each equipped with a light guiding portion;

simultaneously directly or indirectly, and respectively linking the first and second reaction containers to the first and second link portions so as to optically connect the inside of the linked first and second reaction containers to the light guiding portions;

performing temperature control inside the first and second reaction containers; and guiding light from the first and second reaction containers to a connection end array body supporting and arranging, along a predetermined path, first and second connection ends each equipped with a rear end of the respective guiding portions, wherein a front end of the respective light guiding portions are provided to each of the first and second link portions, and sequentially, respectively and optically connecting the first connection end to a first measurement end provided in a measurement unit so as to be adjacent to or contact the first connection end and the second connection end to a second measurement end provided in a measurement unit so as to be adjacent to or contact the second connection end along the predetermined path via relative movement between the connection end array body and the first and second measurement ends, so that light based on optical states inside the first and second reaction containers is received by the measurement unit, wherein the step of applying the ultrasonic vibration to the first and second sample suspensions comprises:

attaching a first scattering prevention lid to the dispensing head so as to transfer the first scattering prevention lid in the linear arrangement direction while the first scattering prevention lid is attached to the dispensing head after storing the first sample suspension in the first liquid storage portion and attaching a second scattering prevention lid to the dispensing head so as to transfer the second scattering prevention lid in the linear arrangement direction while the second scattering prevention lid is attached to the dispensing head after storing the second sample suspension in the second liquid storage portion;

attaching the first scattering prevention lid to a first opening portion of the first liquid storage portion receiving the first sample suspension so as to close the first opening portion by detaching the first scattering prevention lid from the dispensing head and attaching the second scattering prevention lid to a second opening portion of the second liquid storage portion receiving the second sample suspension so as to close the second opening portion by detaching the second scattering prevention lid from the dispensing head;

sequentially applying ultrasonic vibration to the first and second sample suspensions with an ultrasonic vibration unit that includes an ultrasonic vibrator and a horn resonated by the vibration of the ultrasonic vibrator after detaching the first and second scattering prevention lids from the dispensing head; and punching films of the first and second scattering prevention lids by downward movement of punching tips that are detachably attached to the dispensing head after the ultrasonic vibration is sequentially applied to the respective first and second sample suspensions with the ultrasonic vibration unit so that the first sample suspension can be taken out by the first dispensing tip attached to the dispensing head and the second sample suspension can be taken out by the second dispensing tip attached to the dispensing head, wherein the step of sequentially applying ultrasonic vibration comprises moving the ultrasonic vibration unit in a direction perpendicular to the linear arrangement direction so as to cross the first and second linear shapes, and moving the horn of the ultrasonic vibration unit so as to press the first liquid storage portion receiving the first sample suspension in the first linear shape and moving the horn of the ultrasonic vibration unit so as to press the second liquid storage portion receiving the second sample suspension in the second linear shape, and wherein at least part of a trestle movement mechanism is provided to the dispensing head so that at least part of the light guiding trestle moves together with the dispensing head in the linear arrangement direction.

* * * * *

UNITED STATES PATENT AND TRADEMARK OFFICE
CERTIFICATE OF CORRECTION

PATENT NO. : 10,775,397 B2
APPLICATION NO. : 14/443256
DATED : September 15, 2020
INVENTOR(S) : Hideji Tajima It is certified that error appears in the above-identified patent and that said Letters Patent is hereby corrected as shown below:

In the Claims

Column 50, Line 51-56 of Claim 6:
"...a light guiding trestle that includes first and second link portions which are directly or indirectly respectively linked to the first and second reaction containers and are each equipped with a flexible light guiding portions optically connected to the inside of the respectively linked first and second reaction containers..."
Should instead read:
--...a light guiding trestle that includes first and second link portions which are directly or indirectly respectively linked to the first and second reaction containers and are each equipped with a flexible light guiding portion optically connected to the inside of the respectively linked first and second reaction containers...--

Column 52, Lines 45-48 of Claim 13:
"...wherein the first linear shape corresponds to the first dispensing tip so that the first dispensing tip enters the first linear shape and does not enter the second linear shapes..."
Should instead read:
--...wherein the first linear shape corresponds to the first dispensing tip so that the first dispensing tip enters the first linear shape and does not enter the second linear shape...--

Column 54, Lines 5-8 of Claim 15:
"...moving a light guiding trestle relative to the first and second reaction containers, the light guiding trestle including first and second link portions each equipped with a flexible light guiding portions..."
Should instead read:
--...moving a light guiding trestle relative to the first and second reaction containers, the light guiding trestle including first and second link portions each equipped with a flexible light guiding portion...--

Column 54, Lines 16-21 of Claim 15:
"......guiding light from the first and second reaction containers to a connection end array body including an arrangement surface supporting and arranging first and second connection ends along a Signed and Sealed this
Twenty-fourth Day of November, 2020

Andrei Iancu
*Director of the United States Patent and Trademark Office* predetermined path, the first and second connection ends each being equipped with a rear ends of the respective light guiding portion..."
Should instead read:
--...guiding light from the first and second reaction containers to a connection end array body including an arrangement surface supporting and arranging first and second connection ends along a predetermined path, the first and second connection ends each being equipped with a rear end of the respective light guiding portion...--